US009598395B2

(12) United States Patent
Gatti et al.

(10) Patent No.: US 9,598,395 B2
(45) Date of Patent: Mar. 21, 2017

(54) PREMATURE-TERMINATION-CODONS READTHROUGH COMPOUNDS

(71) Applicant: The Regents of the University of California, Oakland, CA (US)

(72) Inventors: Richard A. Gatti, Sherman Oaks, CA (US); Liutao Du, West Hills, CA (US); Hailiang Hu, Los Angeles, CA (US); Robert Damoiseaux, Beverly Hills, CA (US); Michael E. Jung, Los Angeles, CA (US); Jin-Mo Ku, Gunpo-si (KR); Gladys Completo, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/387,212

(22) PCT Filed: Mar. 15, 2013

(86) PCT No.: PCT/US2013/032209
§ 371 (c)(1),
(2) Date: Jan. 12, 2015

(87) PCT Pub. No.: WO2013/142346
PCT Pub. Date: Sep. 26, 2013

(65) Prior Publication Data
US 2015/0051251 A1    Feb. 19, 2015

Related U.S. Application Data

(60) Provisional application No. 61/615,173, filed on Mar. 23, 2012, provisional application No. 61/657,544, filed on Jun. 8, 2012.

(51) Int. Cl.
*C07D 401/04* (2006.01)
*C07D 401/14* (2006.01)

(52) U.S. Cl.
CPC ......... *C07D 401/04* (2013.01); *C07D 401/14* (2013.01)

(58) Field of Classification Search
CPC .................................................. C07D 401/04
USPC ....................................... 546/272.4; 514/340
See application file for complete search history.

(56) References Cited

U.S. PATENT DOCUMENTS

| 3,637,734 | A | 1/1972 | Harnisch et al. |
| 3,906,010 | A | 9/1975 | Pelosi, Jr. et al. |
| 5,554,767 | A | 9/1996 | Wang et al. |
| 6,727,267 | B2 | 4/2004 | Jaen et al. |
| 8,426,540 | B2 | 4/2013 | Sirol |
| 2004/0204461 | A1 | 10/2004 | Karp et al. |
| 2004/0214872 | A1 | 10/2004 | Suto et al. |
| 2005/0154039 | A1 | 7/2005 | Glacera Contour et al. |
| 2005/0209287 | A1 | 9/2005 | Olson |
| 2005/0288347 | A1 | 12/2005 | Hodge et al. |
| 2006/0025461 | A1 | 2/2006 | Tobe et al. |
| 2007/0037752 | A1 | 2/2007 | Ansorge et al. |
| 2007/0203194 | A1 | 8/2007 | Zelle et al. |
| 2009/0163545 | A1 | 6/2009 | Goldfarb |
| 2010/0056464 | A1 | 3/2010 | Gunic et al. |
| 2011/0257211 | A1 | 10/2011 | Chand et al. |
| 2013/0274283 | A1 | 10/2013 | Gatti et al. |
| 2014/0242135 | A1 | 8/2014 | Zwiebel |

FOREIGN PATENT DOCUMENTS

| GB | 2387172 A | 10/2003 |
| JP | 11-302280 | 11/2011 |
| WO | WO 00/10573 A1 | 3/2000 |
| WO | WO 00/32598 A1 | 6/2000 |
| WO | WO 2004/089367 A1 | 10/2004 |
| WO | WO 2009/030996 A1 | 3/2009 |
| WO | WO 2011/063602 A1 | 6/2011 |

OTHER PUBLICATIONS

Goldfarb CA 2009:846114.*
Goldfarb CA 2009:846104.*
International Search Report and Written Opinion in PCT/US2013/032209, mailed Jun. 4, 2013, 17 pages.
Ambinter Stock Screening Collection (2013) *Database Chemcats Chemical Abstracts Service*, Columbus, Ohio, XP002696929, 5 pages.
CAS Registry No. 1223469-97-3, May 14, 2010.
CAS Registry No. 1227733-71-2, Jun. 15, 2010.
CAS Registry No. 29095-25-8, Nov. 16, 1984.
CAS Registry No. 312925-94-3, Jan. 5, 2001.
CAS Registry No. 312926-79-7, Jan. 5, 2001.
CAS Registry No. 333393-11-6, Apr. 30, 2001.
CAS Registry No. 333393-23-0, Apr. 30, 2001.
CAS Registry No. 370081-35-9, Nov. 15, 2001.
CAS Registry No. 401640-08-2, Mar. 18, 2002.
CAS Registry No. 471918-99-7, Nov. 8, 2002.
CAS Registry No. 471919-11-6, Nov. 8, 2002.
CAS Registry No. 73855-59-1, Nov. 16, 1984.
CAS Registry No. 892100-22-0, Jul. 11, 2006.
CAS Registry No. 925397-33-7, Mar. 7, 2007.
Ceasar et al., Orbital Interaction in 2a,8b-Dihydrocyclopent[cd]Azulene (1968) *Tetrahedron Letters* 20:1721-1724.
De La Rosa et al., Tri-substituted triazoles as potent non-nucleoside inhibitors of the HIV-1 reverse transcriptase (2006) *Bioorganic & Medicinal Chemistry Letters* 16:4444-4449.
Du et al., Nonaminoglycoside compounds induce readthrough of nonsense mutations (2009) *Journal of Experimental Medicine* 206:2285-2297.
Du et al., Rapid screen for truncating ATM mutations by PTT-ELISA (2008) *Mutation Research* 640:139-144.

(Continued)

*Primary Examiner* — Patricia L Morris
(74) *Attorney, Agent, or Firm* — Foley Hoag LLP; David P. Halstead

(57) ABSTRACT

Premature termination codons readthrough compounds, composition thereof, and methods of making and using the same are provided.

10 Claims, 33 Drawing Sheets

(56) References Cited

OTHER PUBLICATIONS

Felise et al., An Inhibitor of Gram-Negative Bacterial Virulence Protein Secretion (2008) *Cell Host & Microbe* 4:325-336.
Gränacher et al., Über die Verwendung des Rhodanins zu organischen Synthesen IV. Indol- und Furyl-Brenztraubensäure (1924) *Helvetica Chimica Acta* 7:575-578.
Hallgas et al., Comparison of measured and calculated lipophilicity of substituted aurones and related compounds (2004) *Journal of Chromatography B* 801:229-235.
Jung et al., Synthesis and evaluation of compounds that induce readthrough of premature termination codons (2011) *Bioorganic & Medicinal Chemistry Letters* 21:5842-5848.
Kloc et al., Reactions at the nitrogen atoms in azafluorene systems (1979) *Canadian Journal of Chemistry* 57:1506-1510.
Lai et al., Correction of ATM gene function by aminoglycoside-induced read-through of premature termination codons (2004) *Proc. Nat'l. Acad. Sci. USA* 101:15676-15681.
Law, H.B., Electrolytic Oxidation (1906) *Journal of the Chemical Society, Transactions* 89:1437-1453.
Libermann et al., La Thiazolidione, point de départ d'une synthèse des acides thiopyruviques et thioglyoxyliques substiués (1948) *Bulletin de la Société Chimique de France* 1120-1124.
Midituru et al., High-Throughput Kinase Profiling: A More Efficient Approach toward the Discovery of New Kinase Inhibitors (2011) *Chemistry & Biology* 18:868-879.
Mure et al., Model Studies of Topaquinone-Dependent Amine Oxidases. 1. Oxidation of Benzylamine by Topaquinone Analogs (1995) *Journal of the American Chemical Society* 1117:8698-8706.
Pinson et al., Thiazolidinedione-Based PI3Kα Inhibitors: An Analysis of Biochemical and Virtual Screening Methods (2011) *ChemMedChem* 6:514-522.
Pope, F.G., Colour and constitution of azomethine compounds. Part 1. (1908) *Proceedings of the Chemical Society*, London 24:24.
Richardson et al., Discovery of a potent CDK2 inhibitor with a novel binding mode, using virtual screening and initial, structure-guided lead scoping (2007) *Bioorganic & Medicinal Chemistry Letters* 17:3880-3885.
Stevens et al., Physostigmine Subsitutes (1941) *Journal of the American Chemical Society* 63:308-311.
Wheeler et al., On some aldehyde condensation producs of arylpseudothiohydantoins (1903) *Journal of the American Chemical Society* 25:366-371.
Zelenin et al., Synthesis and Structure of Thioacylhydrazones, translated from Russian *Journal of Organic Chemistry of the USSR* (1984) 20:152-167.
Fernández, et al. "A new type of five-membered heterocyclic inhibitors of basic metallocarboxypeptidases," *European Journal of Medicinal Chemistry*, 2009, vol. 44, pp. 3266-3271 (available online Apr. 2009).
Kirschberg, et al. "Triazole derivatives as non-nucleoside inhibitors of HIV-1 reverse transcriptase—Structure—activity relationships and crystallographic analysis," *Bioorganic & Medicinal Chemistry Letters*, 2008 (available online Dec. 5, 2007), vol. 18, pp. 1131-1134.
Communication issued by the EPO in EP Appl. No. 13714784.9, Dec. 1, 2015, 9 pages.

* cited by examiner

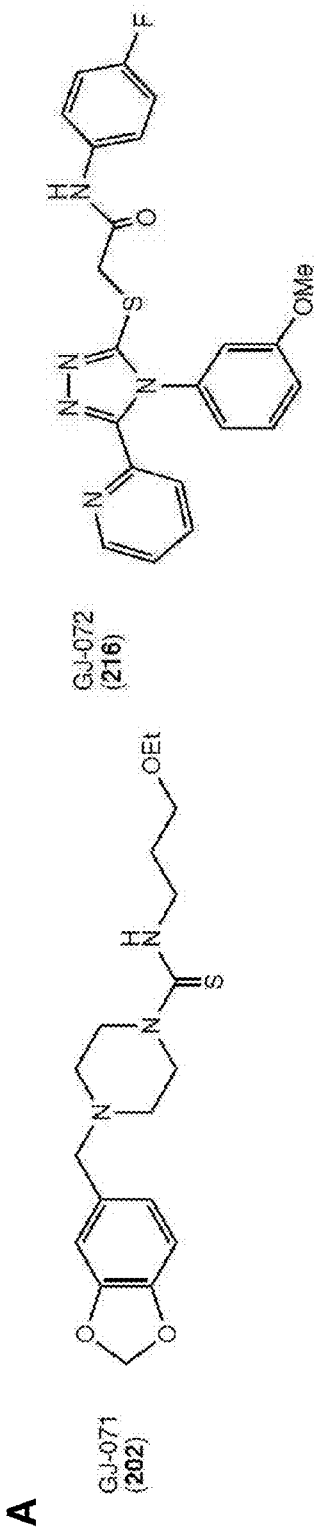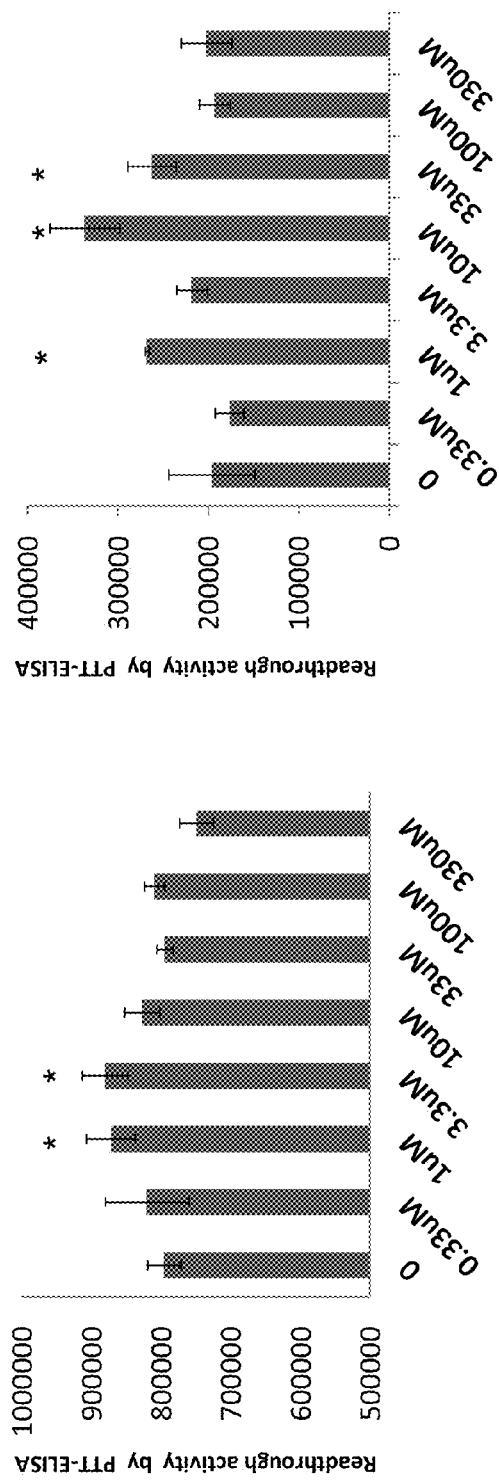
Fig.1

Fig.2 Effects on TGA and TAG

Fig. 3 ATMs1981 IRIF in A-T cells with TAA.

Figure 5. Synthesized GJ-072 Analogs

Fig.6. Analogs on TGA by FCATM

Fig.7. Analogs data on TAG by IRIF/FCATM

Fig. 8. Analogs activity on TAA by FCATM

Figure 9. comparison with 13-14 and PTC124

Two more potential readthrough compounds: 204 and 219
A
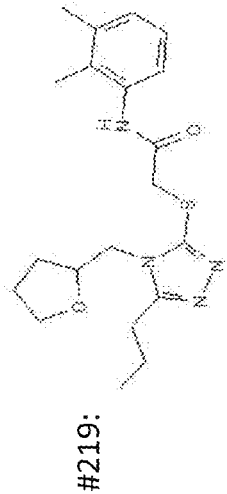
204:
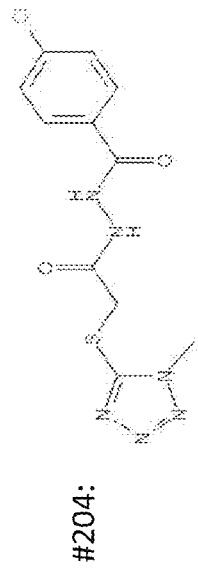
219:
B
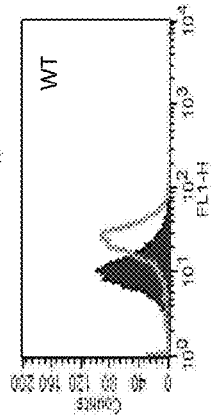 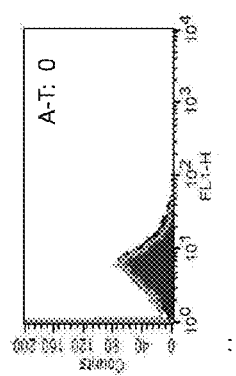
204:
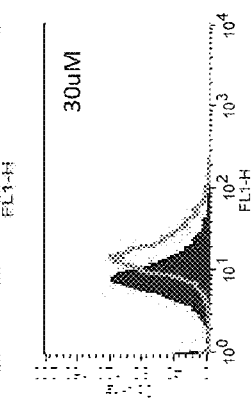 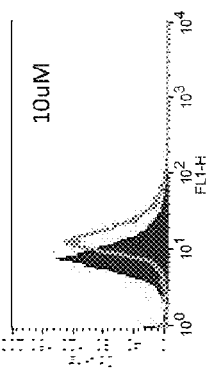
219:
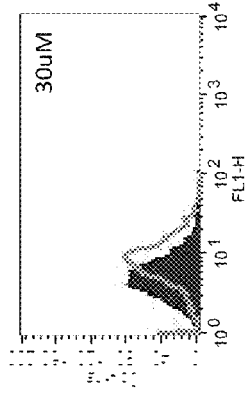 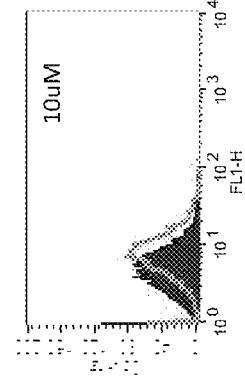
Fig. 29

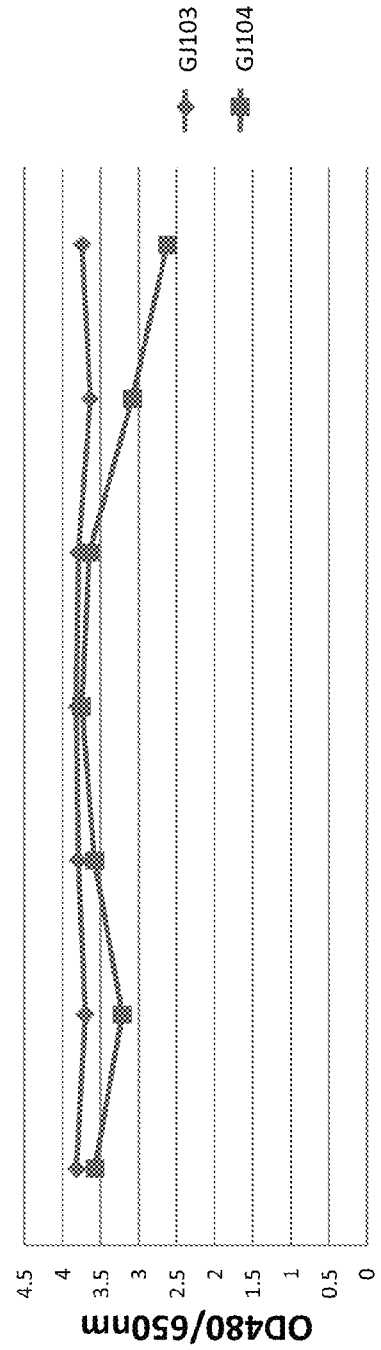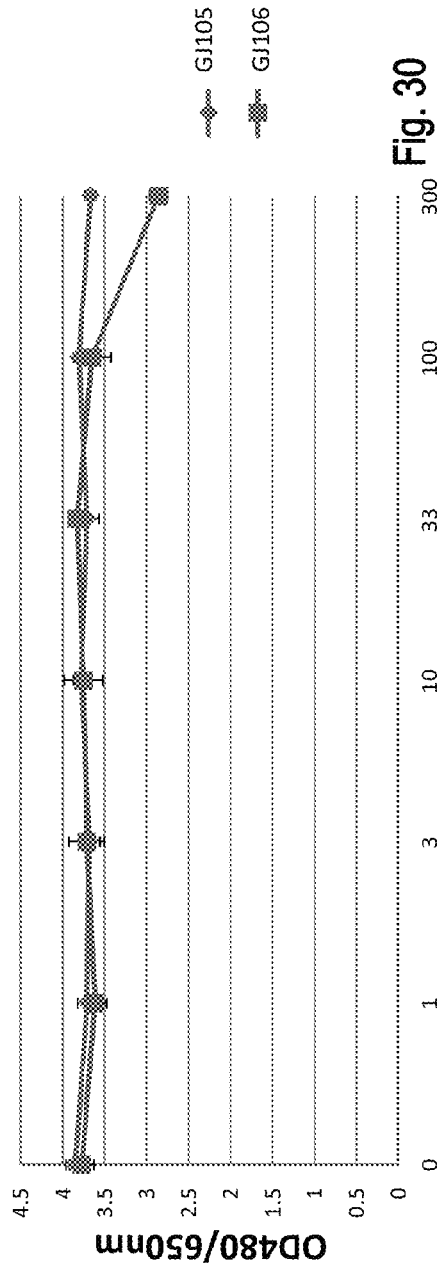
Fig. 30

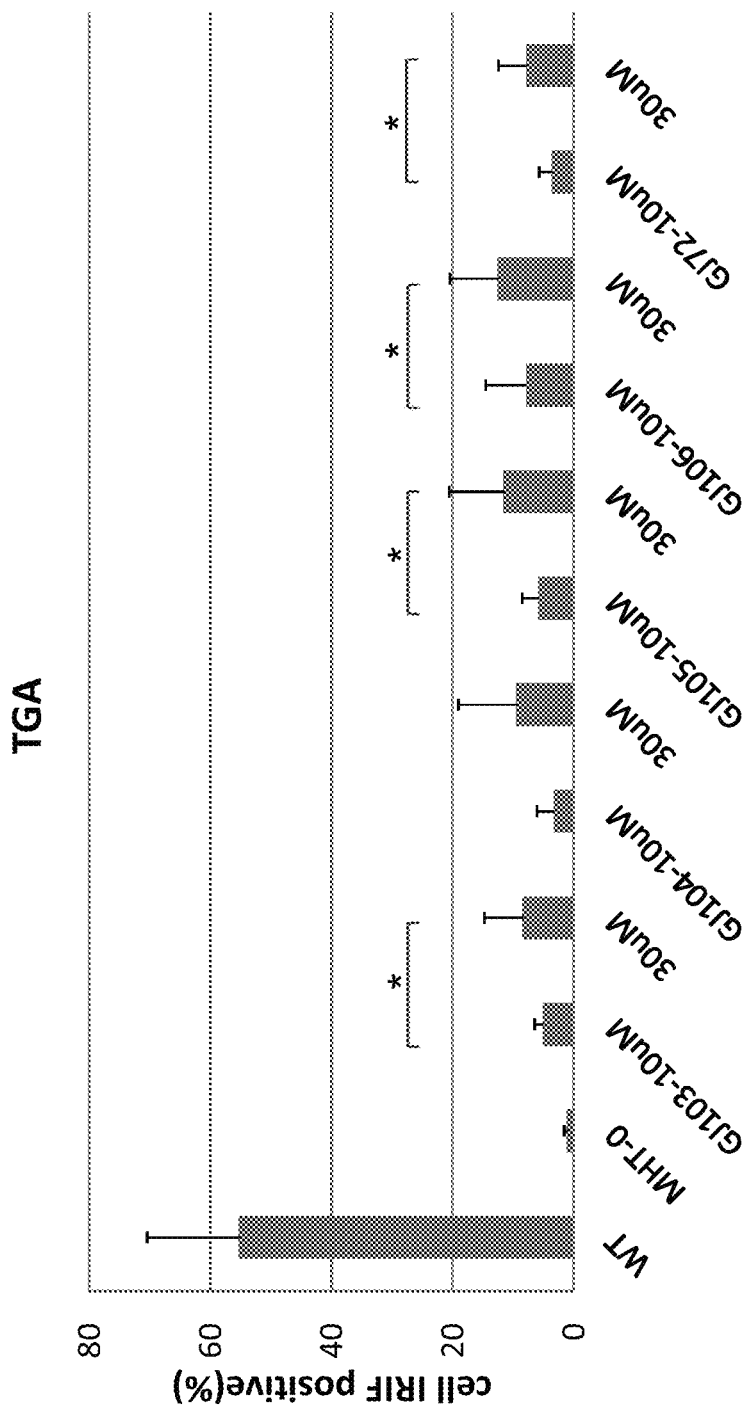
Fig. 31. Analogs on TGA by IRIF

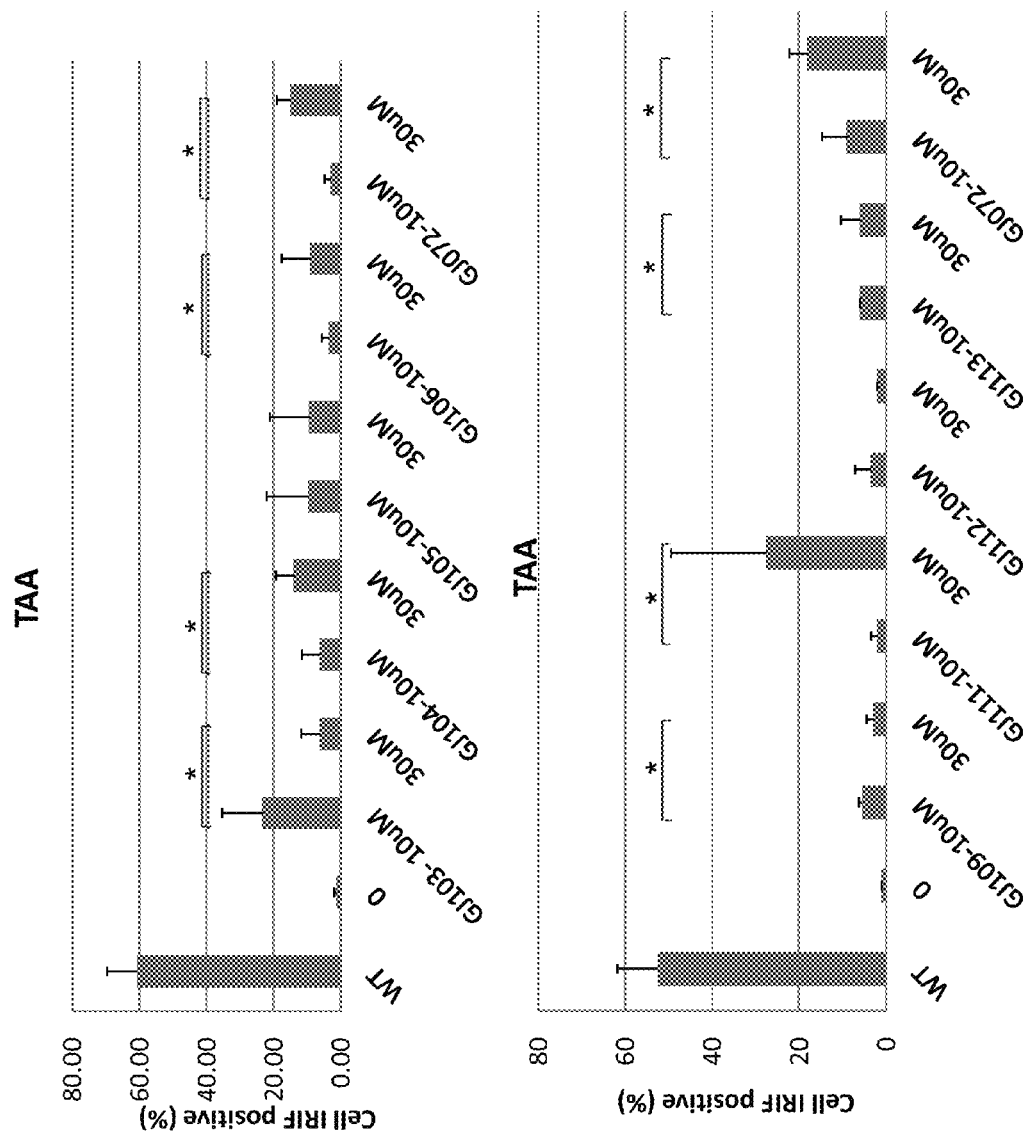
Fig. 32. Analogs activity by IRIF on TAA

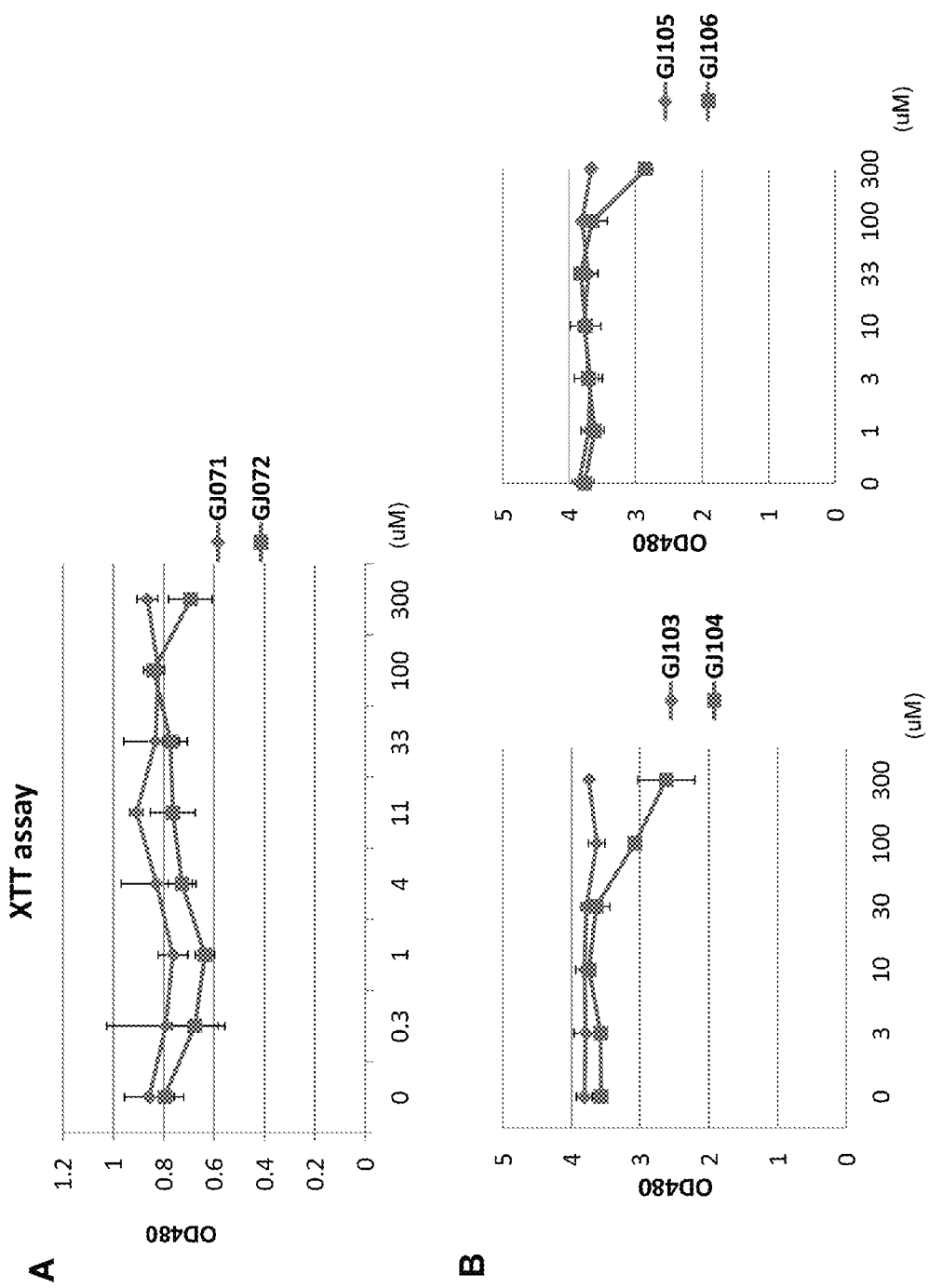
Fig. 33. Cytotoxicity of RTCs

PREMATURE-TERMINATION-CODONS READTHROUGH COMPOUNDS

CROSS-REFERENCE TO RELATED APPLICATIONS

This application is the National Stage of International Patent Application No. PCT/US2013/032209, filed Mar. 15, 2013, which claims the benefit of U.S. Provisional Patent Application Nos. 61/615,173 and 61/657,544, filed Mar. 23, 2012 and Jun. 8, 2012, respectively, the teaching of each of which are incorporated herein by reference in their entireties.

STATEMENT AS TO RIGHTS TO INVENTIONS MADE UNDER FEDERALLY SPONSORED RESEARCH AND DEVELOPMENT

This invention was made with Government support of Grant No. NS052528, awarded by the National Institutes of Health. The Government has certain rights in this invention.

FIELD

Provided herein are premature-termination-codon (PTC) readthrough-inducing compounds and methods of making and using the same.

BACKGROUND

Read-through compounds have received much attention recently. Certain compounds such as gentamicin and PTC124 have been demonstrated with ability to induce readthrough of PTCs, which allows translation of full-length protein. In many cases, the readthrough induced full-length protein is at least partially functional, even when it contains a mis-incorporated amino acid. Therefore, chemical-induced readthrough of PTCs might be exploited as a potential treatment strategy for genetic disorders caused by nonsense mutations.

Large numbers of genetic disorders are caused by nonsense mutations for which compound-induced readthrough of premature termination codons (PTCs) might be exploited as a potential treatment strategy. We have successfully developed a sensitive and quantitative high-throughput screening (HTS) assay, protein transcription/translation (PTT)-enzyme-linked immunosorbent assay (ELISA), for identifying novel PTC-readthrough compounds using ataxia-telangiectasia (A-T) as a genetic disease model (Du et al, 2009). This HTS PTT-ELISA assay is based on a coupled PTT that uses plasmid templates containing prototypic A-T mutated (ATM) mutations for HTS. The assay is luciferase independent. We screened about 34,000 compounds and identified 12 low-molecular-mass nonaminoglycosides with potential PTC-readthrough activity. From these, two leading compounds consistently induced functional ATM protein in ATM-deficient cells containing disease-causing nonsense mutations, as demonstrated by direct measurement of ATM protein, restored ATM kinase activity, and colony survival assays for cellular radiosensitivity. The two compounds also demonstrated readthrough activity in mdx mouse myotube cells carrying a natural nonsense mutation and induced significant amounts of dystrophin protein.

Translation termination is signaled by three stop codons: UAA, UAG, and UGA. This mechanism is highly conserved, although each stop codon has a different efficiency for terminating translation. UGA is considered to be a "leaky" stop codon with the highest intrinsic readthrough potential. UAA shows high fidelity and little intrinsic readthrough potential, whereas UAG has intermediate fidelity (see, e.g., Weiner and Weber, 1973, J. Mol. Biol. 80:837-855). Nonsense mutations create primary premature termination codons (PTCs) and result in either no formation of the target protein or truncated protein with impaired stability.

Certain compounds influence the fidelity of stop codon recognition and induce readthrough of primary PTCs, which allows translation of some full-length protein. In many cases, the readthrough-induced protein is functional, even when it contains a wrongly incorporated amino acid (Keeling and Bedwell, 2005, Current Pharmacogenomics. 3:259-269; Zingman et al., 2007, Clin. Pharmacol. Ther. 81:99-103).

It is estimated that 30% of human disease-causing alleles are nonsense mutations (Mendell and Dietz, 2001; Du et al., 2009, JEM, 206 (10): 2285). Other types of mutation, such as frameshift and splicing mutations, lead to secondary PTCs; however, these are not therapeutic targets for readthrough compounds (RTCs). Considering that >1,800 distinct genetic disorders are caused by nonsense mutations, the readthrough of primary PTCs has treatment potential for large numbers of patients.

To date, there is no efficient treatment for a majority of genetic disorders, such as ataxia telangiectasia (A-T) and Duchenne Muscular Dystrophy (DMD). It has been demonstrated that certain compounds could induce readthrough of premature termination codons (PTCs), which allows translation of full-length protein. In many cases, the readthrough-induced protein is at least partially functional, even when it contains an inaccurate incorporated amino acid (Lai et al., 2004; Du et al., 2009; Keeling and Bedwell, 2005; Zingman et al., 2007). Therefore, chemical-induced readthrough of PTCs might be exploited as a potential treatment strategy. Notably, this readthrough strategy could be especially useful for diseases like A-T and cystic fibrosis (CF), because a small amount of protein restored by readthrough compounds (RTCs), even as little as 1-10%, may still be able to significantly reduce the severity or eliminate the principal manifestations of these disease (Gilad S, 1998; Kerem, 2004; Ramalho et al., 2002, Chun et al., 2004; Du et al., 2009; Kayali et al., 2012).

To date, most reported PTC-RTCs that are active in mammalian cells have belonged to the aminoglycoside antibiotics class (e.g., gentamicin, paromomycin, G418 and its derivatives NB74 and NB84) (Keeling and Bedwell, 2005; Zingman et al., 2007). Certain types of aminoglycosides can induce ribosomes to read through PTC mutations via insertion of a random amino acid by near-cognate transfer RNA. The therapeutic potential of aminoglycosides has been evaluated in the laboratory for different genetic models, such as cystic fibrosis (see, e.g., Du et al., 2002, J. Mol. Med. 80:595-604; Howard et al., 1996; Bedwell et al., 1997), muscular dystrophy (see, e.g., Loufrani et al., 2004, Arterioscler. Thromb. Vasc. Biol. 24:671-676; Howard et al., 2000; Loufrani et al., 2004), Hurler syndrome (Keeling et al., 2001, Hum. Mol. Genet. 10:291-299), cystinosis (Helip-Wooley et al., 2002, Mol. Genet. Metab. 75:128-133), spinal muscular atrophy (Sossi et al., 2001, Eur. J. Hum. Genet. 9:113-120), ataxia-telangiectasia (Lai et al., 2004, Proc. Natl. Acad. Sci. USA. 101:15676-15681), and type 1 Usher syndrome (Rebibo-Sabbah et al., 2007, Hum. Genet. 122: 373-381) and such models could be used to evaluate the compounds described herein. Clinical trials also indicate that aminoglycosides can induce some functional protein production; however, the therapeutic benefits remain uncertain (see, e.g., Politano et al., 2003, *Acta Myol.* 22:15-21; Wilschanski et al., 2000; Clancy et al., 2001). Furthermore, the systemic toxicity of most commercial aminoglycosides in mammals has greatly diminished their potential for successful readthrough therapy (Mingeot-Leclercq and Tulkens, 1999, *Antimicrob. Agents Chemother.* 43:1003-1012; Guan et al., 2000, *Hum. Mol. Genet.* 9:1787-1793). Therefore, efforts are underway to develop better aminoglycoside derivatives with reduced toxicity and enhanced activity (Nudelman et al., 2006, *Bioorg. Med. Chem. Lett.* 16:6310-6315; Rebibo-Sabbah et al., 2007, *Hum. Genet.* 122:373-381).

Nonaminoglycosides (e.g. PTC124, RTC13, RTC14 and tylosin) have been described as well. The macrolide Tylosin has RT activitiy in prokaryotes and is being further evaluated in patients with somatic mutations in colon cancer (Zilberberg et al 2010). Recently, PTC Therapeutics (South Plainfield, N.J.) described a nonaminoglycoside RTC, PTC124, which was developed synthetically by screening >800,000 chemicals and analogues using a luciferase-based HTS assay (see, e.g., Welch et al., 2007, *Nature.* 447:87-91; Du M et al., 2008). A phase-I clinical study in cystic fibrosis showed that PTC124 is generally well tolerated and appears to have more efficient readthrough activity than aminoglycosides (Hirawat et al., 2007, *J. Clin. Pharmacol.* 47:430-444). Moreover, PTC124 does not induce ribosomal readthrough of normal stop codons. However, PTC124 is not equally effective with all three stop codons, working best on the TGA stop codon (Welch et al., 2007). This selective activity limits the number of patients who could be treated with PTC124. Further, PTC124's recent phase 2b clinical study in DMD patients failed with participants not showing a significant improvement in the six-minute walk distance or dystrophin expression (Guglieri M and Bushby K, 2010). In addition, a recent study indicates that the initial discovery of PTC124 by HTS may have been biased due to its direct interaction with the FLuc (firefly luciferase) reporter used (Auld et al., 2009, *Proc. Natl. Acad. Sci. USA.* 106:3585-3590 Peltz et al. 2009; Auld et al. 2010), indicating the importance of a luciferase-independent HTS assay for future drug screening. Lastly, PTC124 does not effectively cross the blood-brain barrier, a critical factor for treating neurological disorders like A-T, Alzheimer diseases and the CNS effects encountered in Hurler patients.

Therefore, successfully developing new RTCs with optimized efficacy and low toxicity could benefit numerous genetic diseases which are caused by nonsense mutations and currently have no cure. Notably, the potential therapeutic benefit of a small molecular RTC may also extend to cancer for individuals carrying nonsense mutations in genes such as BRAC1, BRAC2 and CHEK2. The RTCs described herein are useful for targeting nonsense mutations that cause numerous disorders and diseases. Therefore, the discovery of these new RTCs is a very important finding in this field.

SUMMARY OF THE INVENTION

In one aspect, it is provided a compound having the ability to read through PTCs in RNA, a pharmaceutically acceptable salt thereof or a prodrug thereof, the compound comprising a structure of formula:

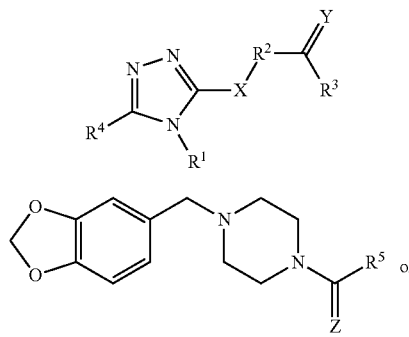

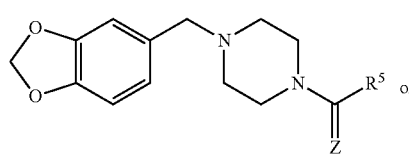

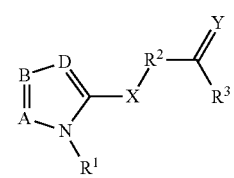

wherein:
A is either nitrogen or carbon, with the carbon being substituted with any aryl or heteroaryl group, any alkyl or substituted alkyl, any arylalkyl or heteroarylalkyl, any functionalized alkyl or aryl (or heteroaryl) group;
B is either nitrogen or carbon, with the carbon being either unsubstituted or substituted with halo, pseudohalo, alkyl, alkoxy, or thioalkoxy groups;
D is either nitrogen or carbon, with the carbon being either unsubstituted or substituted with halo, pseudohalo, alkyl, alkoxy, or thioalkoxy groups;
$R^1$ is any aryl or heteroaryl group, any alkyl or substituted alkyl, any arylalkyl or heteroarylalkyl, any functionalized alkyl or aryl (or heteroaryl) group;
$R^2$ is a methylene unit $(CH_2)_n$ where n is 1, 2, or 3; or the carbon atom or atoms of a ring, either carbocyclic or heterocyclic, of from 3-10 atoms;
$R^3$ is any aryl or heteroaryl group, any alkyl or substituted alkyl, any arylalkyl or heteroarylalkyl, any functionalized alkyl or aryl (or heteroaryl) group, hydroxy, alkoxy, or —$NR^6R^{6a}$;
$R^4$ is any aryl or heteroaryl group, any alkyl or substituted alkyl, any arylalkyl or heteroarylalkyl, any functionalized alkyl or aryl (or heteroaryl) group;
$R^5$ is any aryl or heteroaryl group, any alkyl or substituted alkyl, any arylalkyl or heteroarylalkyl, any functionalized alkyl or aryl (or heteroaryl) group, or —$NR^{5a}R^{5b}$;
$R^{5a}$ is hydrogen or alkyl;
$R^{5b}$ is alkyl, alkoxyalkyl, alkenyl, aryl, arylalkyl, heteroaryl, or heteroarylalkyl, where the aryl and heteroaryl, either alone or as part of arylalkyl and heteroarylalkyl, are optionally substituted with 1, 2, or 3 groups independently selected from alkyl, halo, haloalkyl, hydroxy, and alkoxy;
$R^6$ is hydrogen or alkyl;
$R^{6a}$ is —NHC(O)(arylalkyl), alkyl, hydroxyalkyl, cycloalkyl, heteroaryl, or aryl where the aryl, arylalkyl, and heteroaryl are optionally substituted with 1, 2, or 3 groups selected from hydroxy, halo, haloalkyl, alkyl, alkoxy, carboxy, or alkoxycarbonyl;
X is oxygen, sulfur, NH or N-substituted; and
Y is taken from the group, oxygen, sulfur, NH or N-substituted, or carbon, substituted or unsubstituted; and
Z is oxygen, sulfur, NH or N-substituted; or
a pharmaceutically acceptable salt thereof.

Another aspect is a compound of formula Ia:

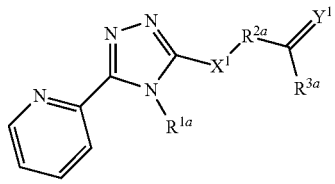

where
R$^{1a}$ is 2-hydroxylphenyl, 2-alkoxyphenyl, 3-hydroxylphenyl, or 3-alkoxyphenyl;
X$^1$ is S, O, NH, or N(C$_{1-3}$-alkyl);
R$^{2a}$ is (CH$_2$)$_m$;
M is 1, 2, or 3;
Y$^1$ is O, S, or NH;
R$^{3a}$ is hydroxy, alkoxy, or —NR$^7$R$^{7a}$;
R$^7$ is hydrogen or C$_{1-3}$-alkyl;
R$^{7a}$ is C$_{1-3}$-alkyl; hydroxyalkyl; cycloalkyl; phenyl substituted with 1, 2, or 3 R$^8$ groups; phenyl substituted with two independently selected halo; or a 6-membered heteroaryl optionally substituted with 1, 2, or 3 R$^9$ groups;
each R$^8$ is independently hydroxy or haloalkyl; and
each R$^9$, when present, is independently hydroxy, alkoxy, halo, haloalkyl, or C$_{1-6}$-alkyl; and
provided that 1) when X$^1$ is S, R$^{2a}$ is —CH$_2$—, Y$^1$ is O, and R$^{3a}$ is —NR$^7$R$^{7a}$, then R$^7$ and R$^{7a}$ are not both ethyl; 2) when X$^1$ is S, R$^{2a}$ is —CH$_2$—, Y$^1$ is O, and R$^{3a}$ is —NR$^7$R$^{7a}$ and R$^7$ is hydrogen, then R$^{7a}$ is not 2-methoxyphenyl; 3) when R$^{1a}$ is 2-methoxyphenyl, X$^1$ is S, R$^{2a}$ is —CH$_2$—, Y$^1$ is O, and R$^{3a}$ is —NR$^7$R$^{7a}$ and R$^7$ is hydrogen, then R$^{7a}$ is not 4-methoxyphenyl; and 4) when R$^{1a}$ is 2-methoxyphenyl or 2-ethoxyphenyl, X$^1$ is S, R$^{2a}$ is —CH$_2$—, Y$^1$ is O, and R$^{3a}$ is —NR$^7$R$^{7a}$ and R$^7$ is methyl, then R$^{7a}$ is not ethyl; or
a pharmaceutically acceptable salt thereof.

Another aspect is a method of treating a diseases or disorder caused by or associated with one or more premature termination codons comprising administering a compound of formula Ib having the ability to read through PTCs in RNA:

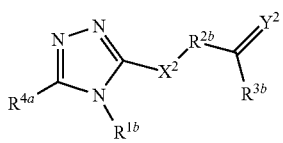

where
R$^{1b}$ is alkyl, alkoxyalkyl, heterocycloalkyl, heterocycloalkylalkyl, aryl, arylalkyl, heteroaryl, or heteroarylalkyl, where the aryl and heteroaryl, either alone or as part of arylalkyl and heteroarylalkyl, are optionally substituted with 1, 2, or 3 R$^{10}$ groups;
X$^2$ is S, O, NH, or N(alkyl);
R$^{2b}$ is (CH$_2$)$_p$;
p is 1, 2, or 3;
Y$^2$ is O, NH, or S;
R$^{3b}$ is hydroxy, alkoxy, or —NR$^{11}$R$^{11a}$;
R$^{4b}$ is alkyl, alkoxyalkyl, heterocycloalkyl, heterocycloalkylalkyl, aryl, arylalkyl, heteroaryl, or heteroarylalkyl, where the aryl and heteroaryl, either alone or as part of arylalkyl and heteroarylalkyl, are optionally substituted with 1, 2, or 3 R$^{12}$ groups;
each R$^{10}$, when present, is independently halo, haloalkyl, alkyl, hydroxy, or alkoxy;
R$^{11}$ is hydrogen or alkyl;
R$^{11a}$ is alkyl, hydroxyalkyl, cycloalkyl, aryl, or heteroaryl where the aryl and heteroaryl are optionally substituted with 1, 2, or 3 R$^{13}$ groups;
each R$^{12}$, when present, is amino, alkylamino, dialkylamino; and
each R$^{13}$, when present, is independently hydroxy, alkoxy, alkoxycarbonyl, halo, haloalkyl, or C$_{1-6}$-alkyl; or
a pharmaceutically acceptable salt thereof.

In another aspect, it is provided a composition, which composition comprising at least one compound according to formula 1, 2, 3, Ia, or Ib, or a pharmaceutically acceptable salt or prodrug thereof, in an amount effective for treating or ameliorating a medical condition associated with PTCs in RNA, wherein the compound of formula 1, 2, 3, Ia, or Ib is according to any of the various embodiments described above or below.

In a further aspect, it is provided a method of making a compound of formula Ia, comprising reacting a compound of formula NHR$^7$R$^{7a}$ with an intermediate of formula

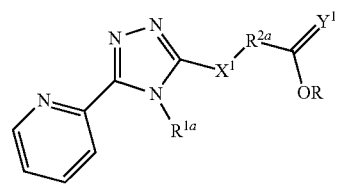

where R is hydrogen or C$_{1-3}$alkyl and all other groups are as described in the various embodiments described above or below. Examples of the method are further described in the Examples.

In a further aspect, it is provided a method of forming a composition, comprising providing a compound of formula 1, 2, 3, Ia, or Ib and forming the composition. In some embodiments, the composition further comprises a pharmaceutically acceptable carrier. In some embodiments of the composition, optionally in combination with any or all of the above various embodiments, the composition is formulated in a formulation for local or systemic delivery. Examples of such formulations are formulations for oral administration, injection, topical administration, pulmonary administration, or implant.

Another aspect is a method for enhancing production in a subject of a functional protein from a gene disrupted by the presence of a premature stop codon in the coding region of the gene, comprising administering to the subject a compound according to formula 1, 2, 3, Ia, or Ib in an amount effective to suppress the premature stop codon and increase transcription of the gene.

Another aspect is a method for enhancing production in a subject of a functional protein, where production of the protein is disrupted by a genetic mutation, comprising administering to the subject a compound of formula 1, 2, 3, Ib, or Ia in an amount effective to suppress the genetic mutation and/or correct a defect caused by the mutation and to increase transcription of the gene.

BRIEF DESCRIPTION OF THE DRAWINGS

FIG. 1. HTS of chemical libraries identified two novel RTCs, GJ071 and GJ072. A. chemical structures of GJ071 and GJ072. B. In vitro readthrough activity measured by PTT-ELISA using plasmid containing the disease-causing mutation, 5623C>T (TGA C) in ATM gene.

Figure 2:
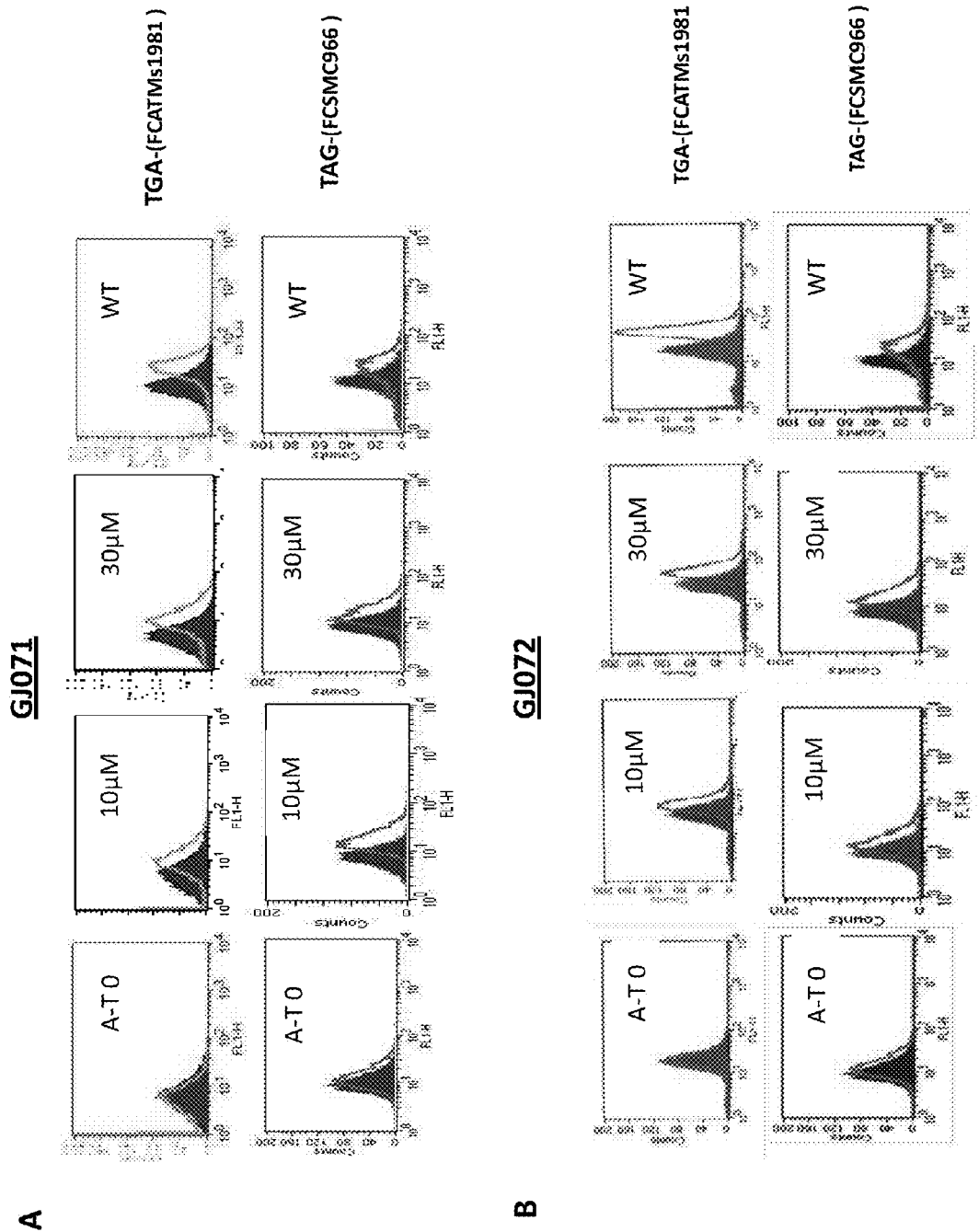

FIG. 2. GJ071 and GJ072 induced ATM kinase activity in A-T cells carrying homozygous TGA or TAG stop codons. A-T cells were treated for 4 days before harvesting. The ATM kinase activity in AT153LA cells with TGA A stop codon was measured by FACS-based ATMs1981 autophosphorylation, and the ATM kinase activity in AT229LA with TAG A stop codon was measured by FACS-based SMC1-966 transphosphorylation (FC-SMCs966). A right shift of fluorescence peaks indicated the restored ATM kinase activity for both. A. GJ071 readthrough activity measured by ATM autophosphorylation. B. GJ072 readthrough activity measured by ATM autophosphorylation.

Figure 3:
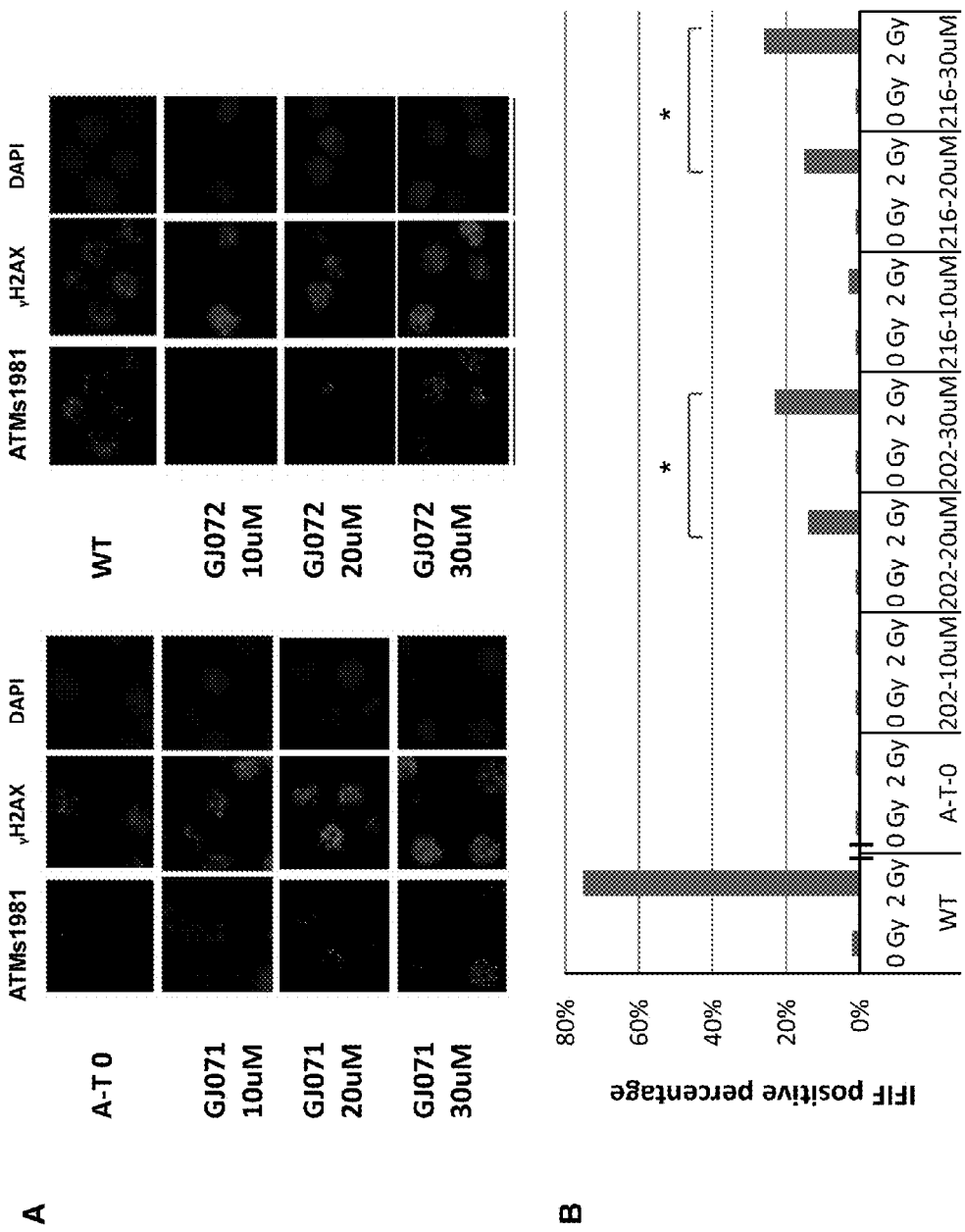

FIG. 3. GJ071 and GJ072 induced post-IR ATMs1981 foci formation in A-T cells with homozygous TAAG mutation. AT185LA cells were treated for 4 days and IRIF was performed. A. Representative photographs of ATMs1981 IRIF induced by GJ071 and GJ072 are shown. The formation of γ-H2AX foci was included as a control for effective irradiation damage. B. The quantitation of cells positive for ATMs1981 IRIF.

Figure 4:
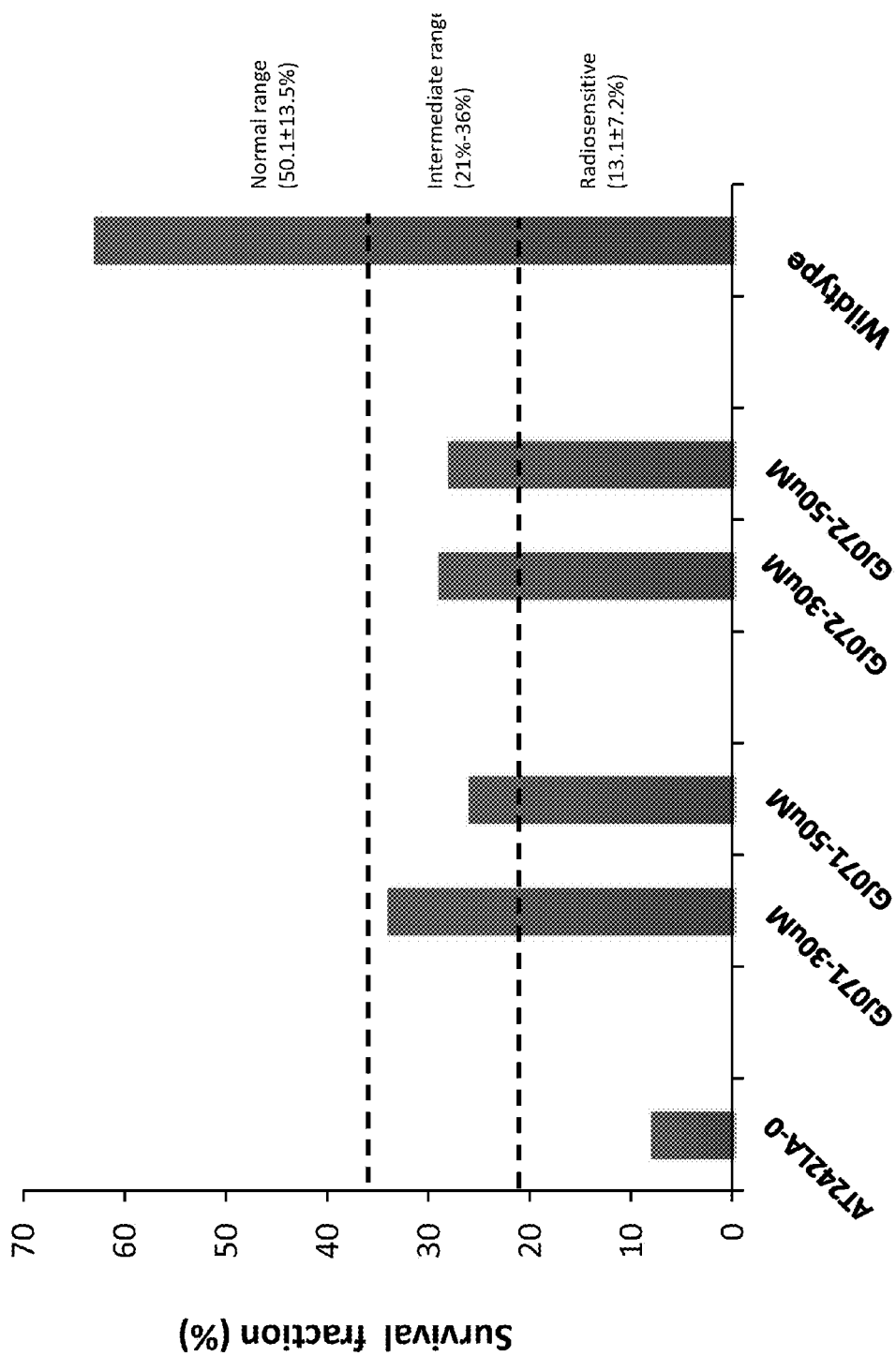

FIG. 4. GJ071 and GJ072 abrogated the radiosensitivity of A-T LCLs. AT242LA cells (containing TGA and TAG stop codons) were treated with compounds and the CSA was measured. Both RTCs increased cell survival fractions from "radiosensitive" to "intermediate" range (as previously described in Sun et al., 2002).

Figure 5:
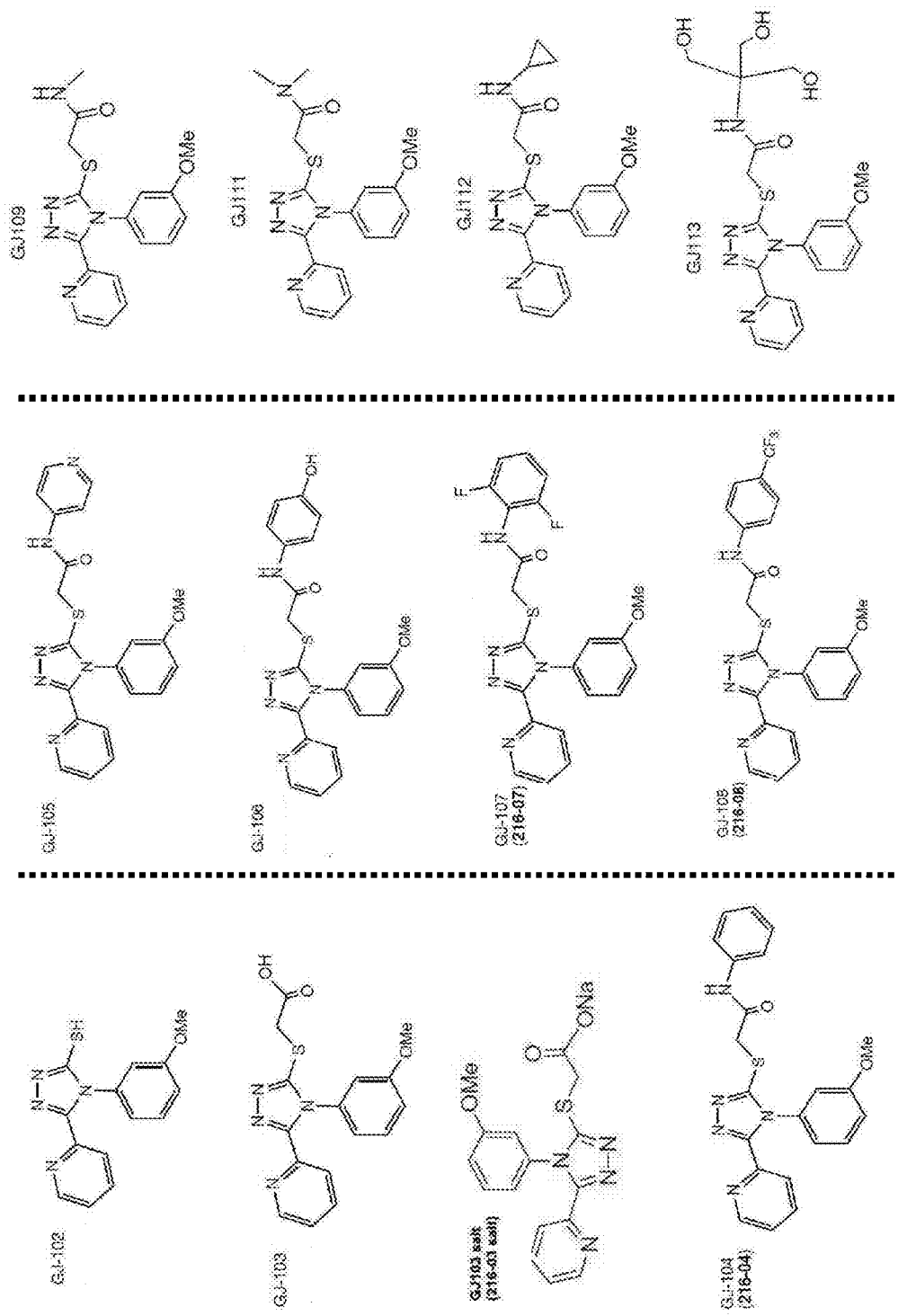

FIG. 5. Structures of all synthesized GJ-072 analogs including the salt form of GJ103.

Figure 6:
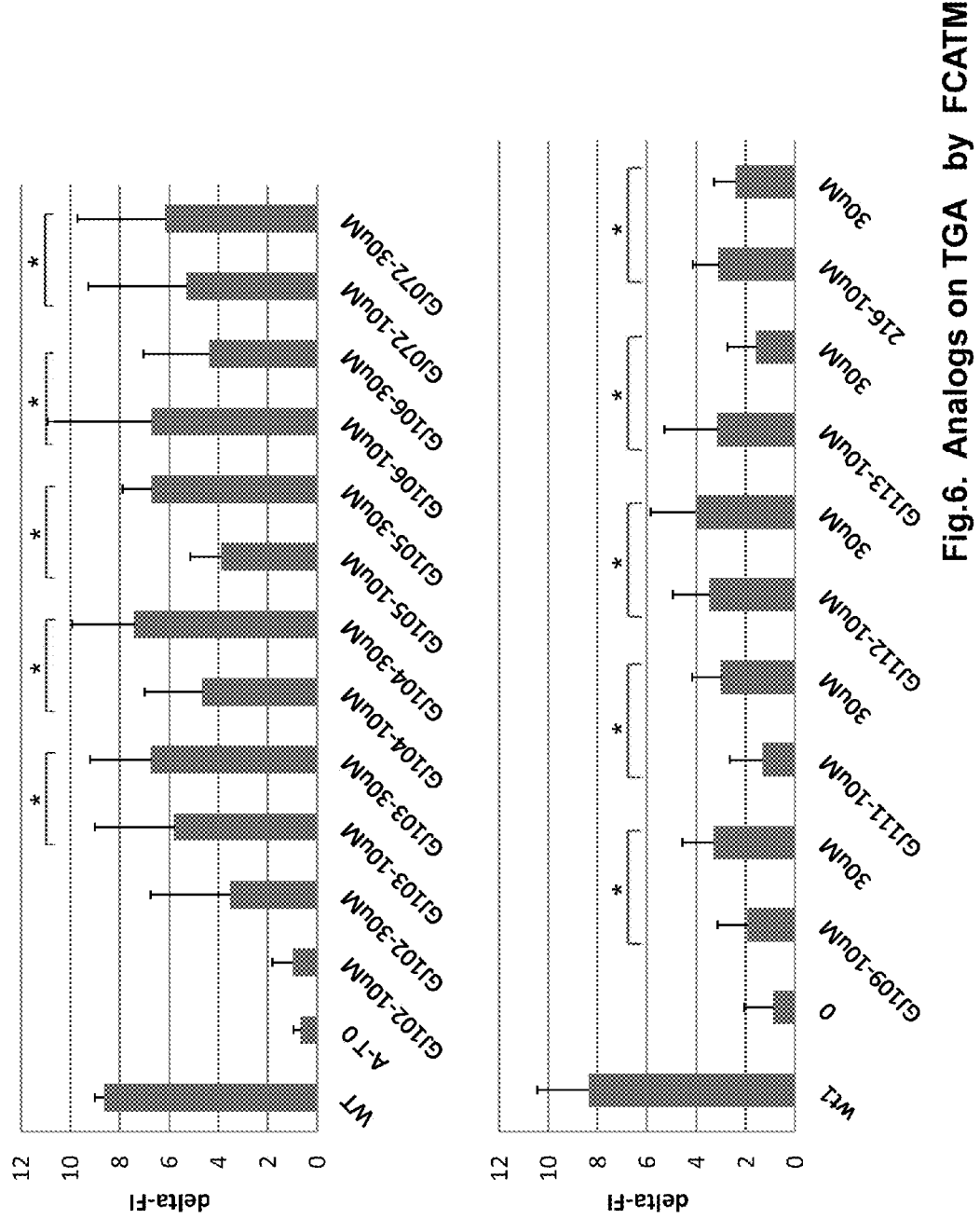

FIG. 6. The effect of GJ072 analogs on TGA in A-T cells measured by FCATMs1981. AT153LA cells were exposed to RTCs for 4 days before assaying. A. Activity of GJ102, GJ103, GJ104, GJ105 and GJ106. The figure data were summarized from 3 independent experiments. B. Activity of GJ109, GJ111, GJ112 and GJ113. These data were combined from 4 independent experiments. *: P≤0.05 as compared untreated A-T control.

Figure 7:
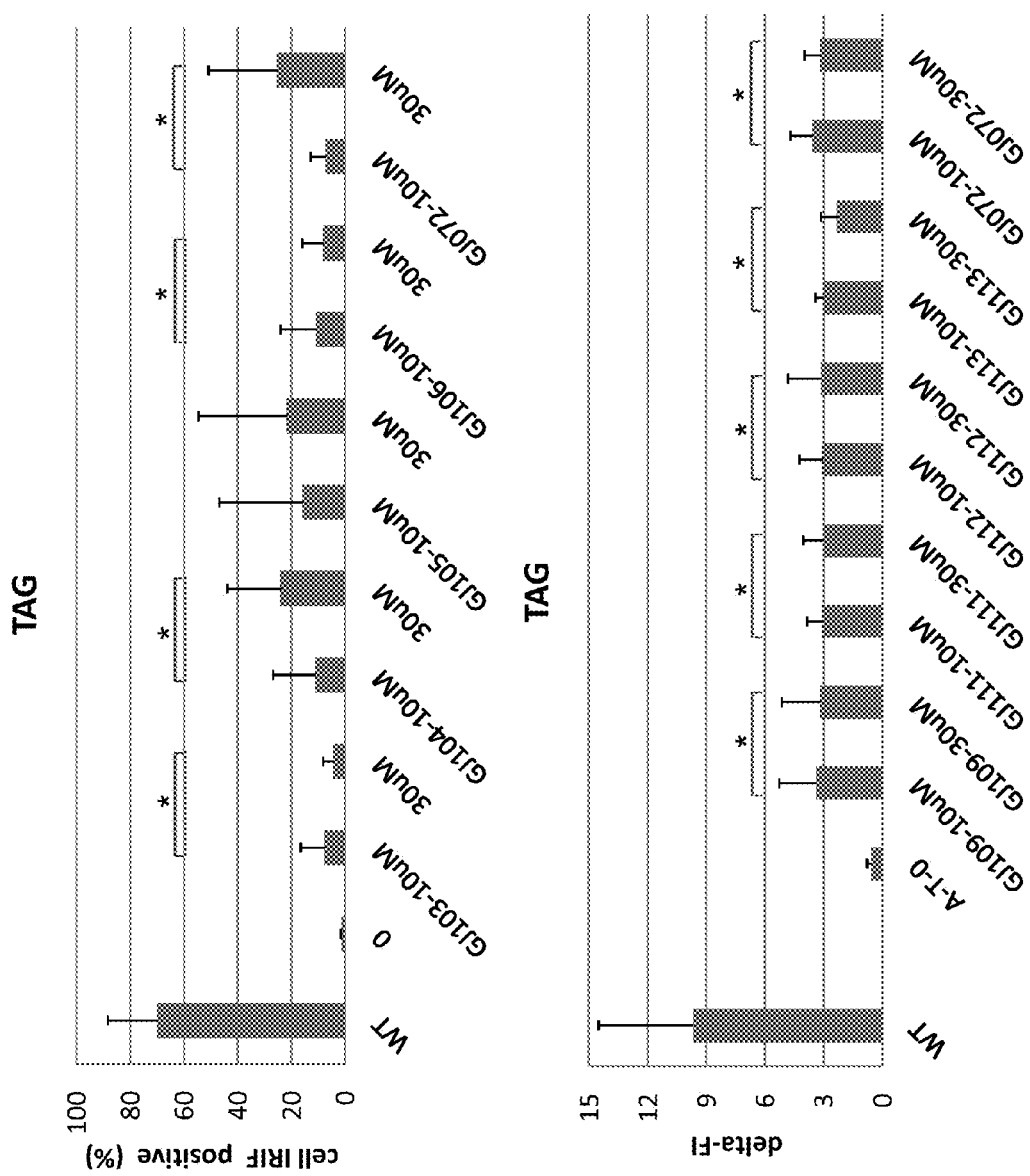

FIG. 7. The effect of GJ072 analogs on TAG in A-T cells. ATM kinase was measured by either ATMs1981-IRIF or FCATMs1981 assay. AT229LA cells were treated with RTCs for 4 days and collected for assaying. A. Activity of GJ103, GJ104, GJ105 and GJ106 by ATMs1981-IRIF. The figure data were summarized from 6 independent experiments. B. Activity of GJ109, GJ111, GJ112 and GJ113 by FCATMs1981. These data were combined from 3 independent experiments. *: P≤0.05 as compared untreated A-T control.

Figure 8:
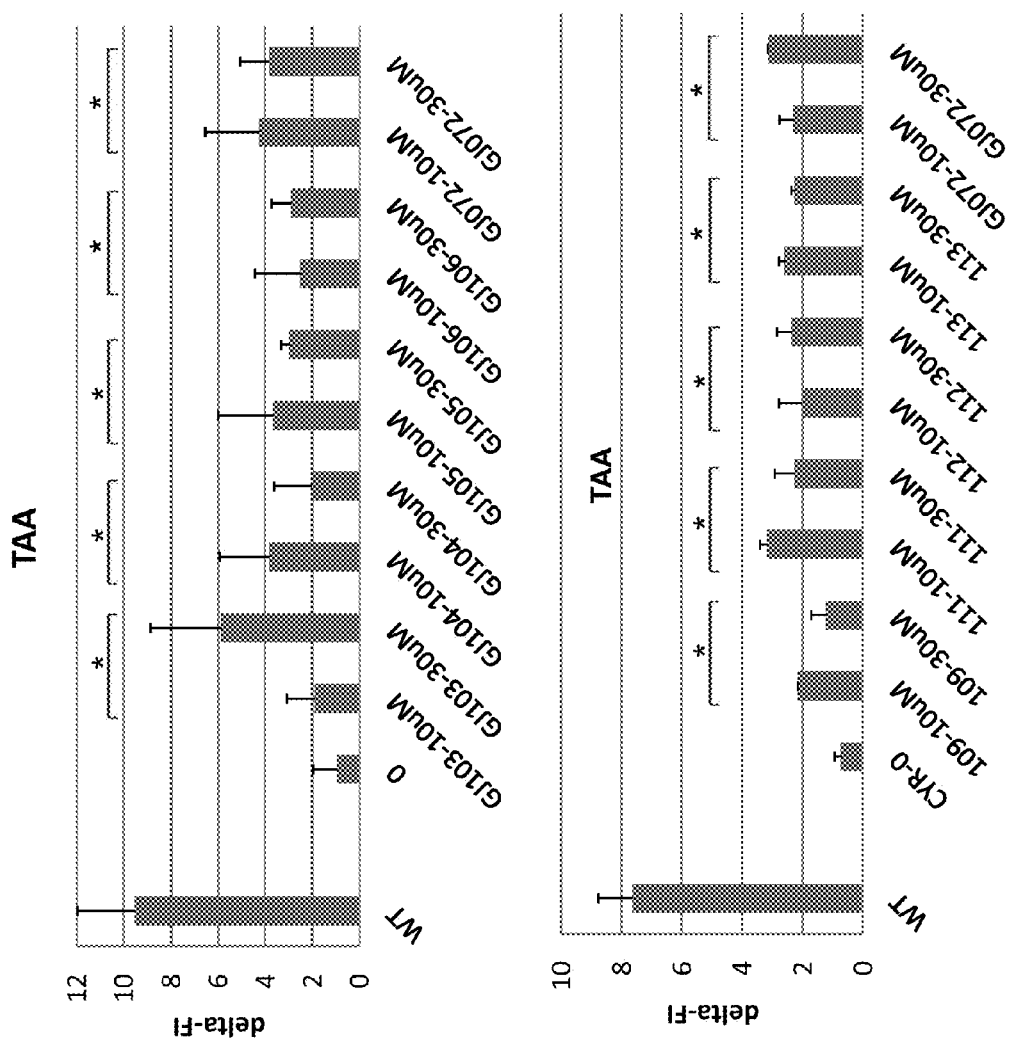

FIG. 8. The effect of GJ072 analogs on TAAG stop codons in A-T cells. AT185LA cells were treated with RTCs for 4 days and collected for FCATMs1981 assaying. A. Activity of GJ102, GJ103, GJ104, GJ105 and GJ106. These data were combined from 3 independent experiments. B. Activity of GJ109, GJ111, GJ112 and GJ113. These data were combined from 2 independent experiments. *: P≤0.05 as compared untreated A-T control.

Figure 9:
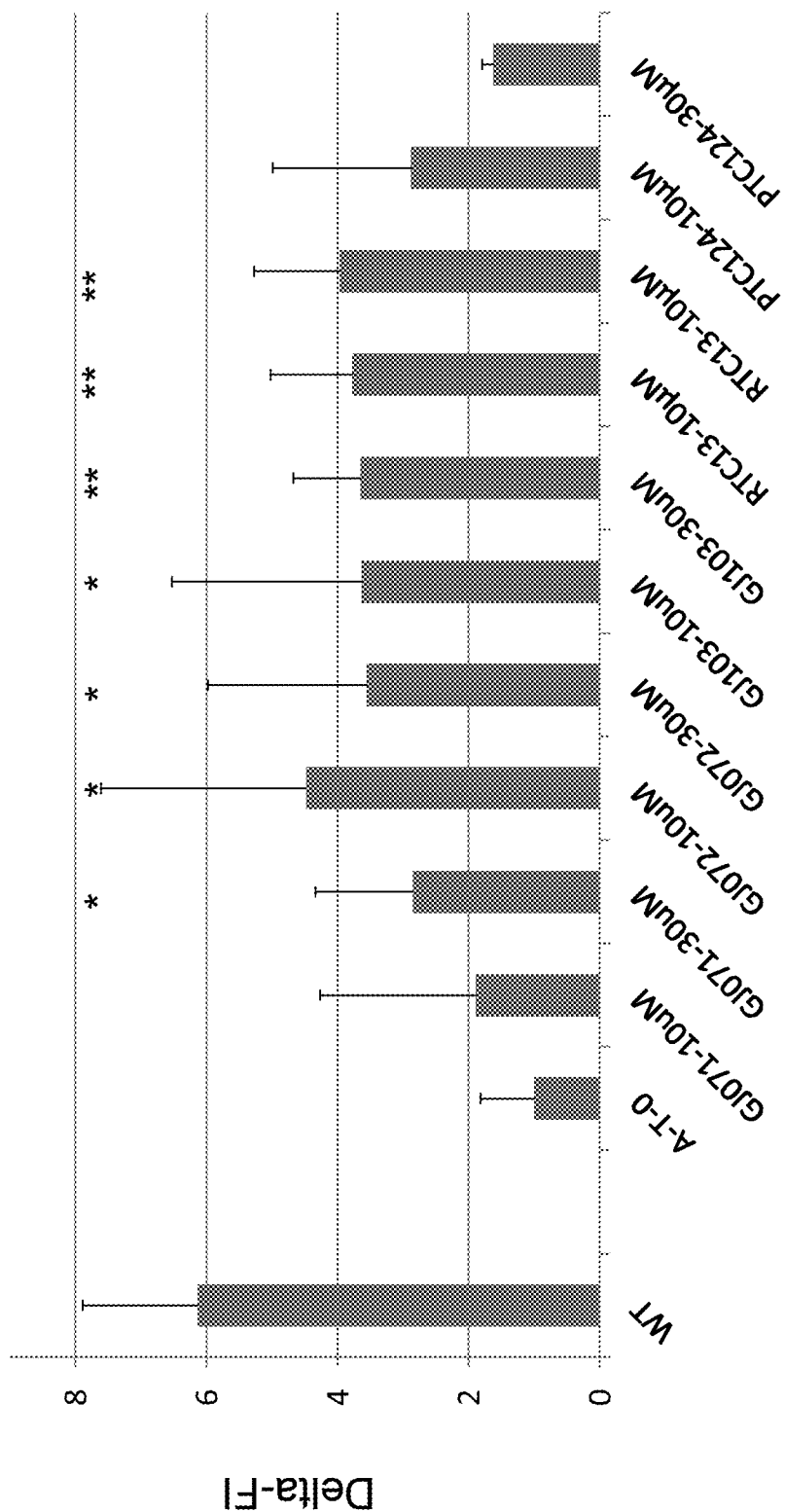

FIG. 9. ATM kinase activity: comparison of most active RTCs. AT153LA cells with homozygous TGA A premature stop codon were exposed to RTCs for 4 days and ATM kinase activity was measured by FCATMs1981. These data were combined from 3 independent experiments. *: P≤0.05; **:P≤0.01, as compared untreated A-T control.

Figure 10:
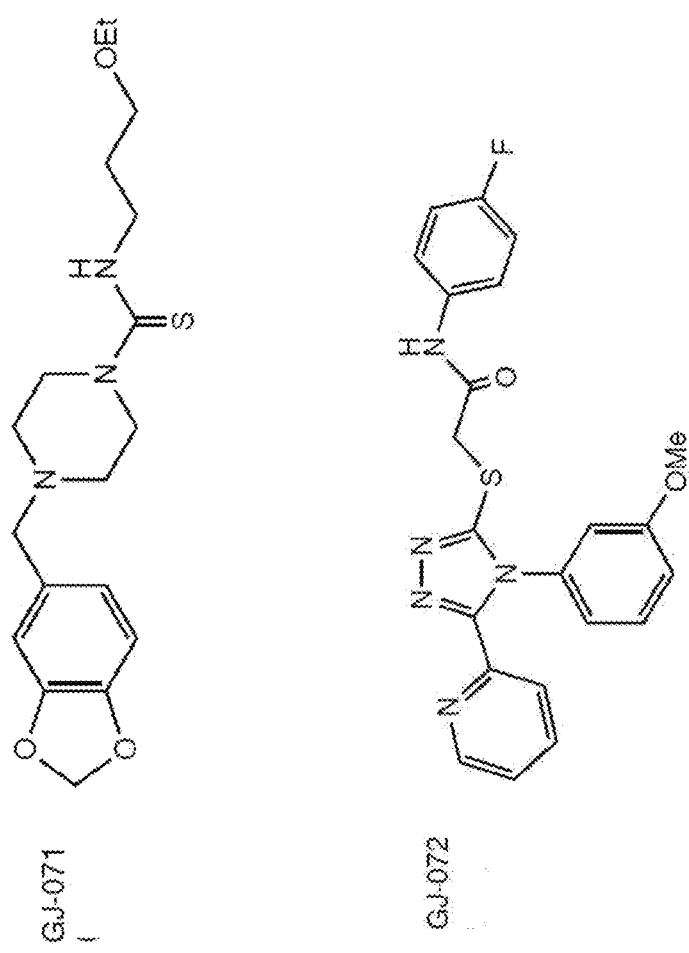

FIG. 10. Structures of exemplary compounds.

Figure 11:
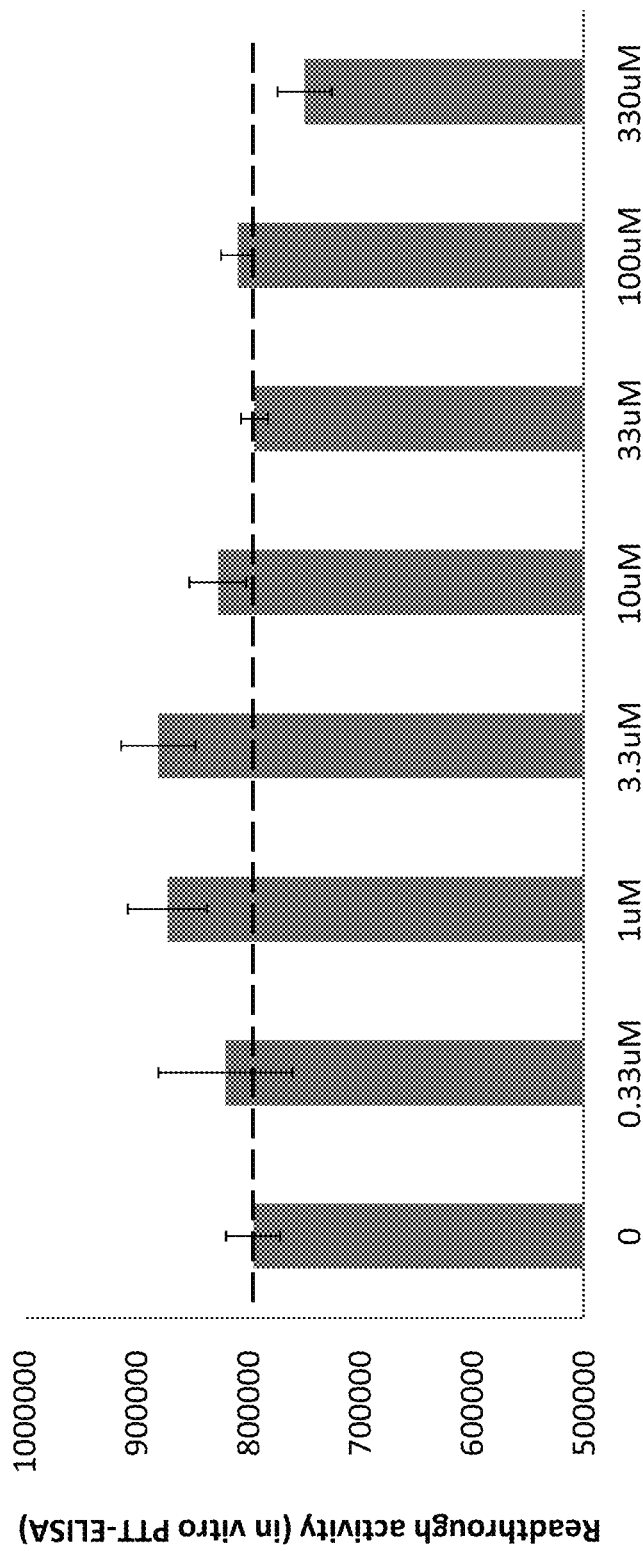

FIG. 11. In vitro readthrough activity of GJ-071 demonstrated by PTT-ELISA assay.

Figure 12:
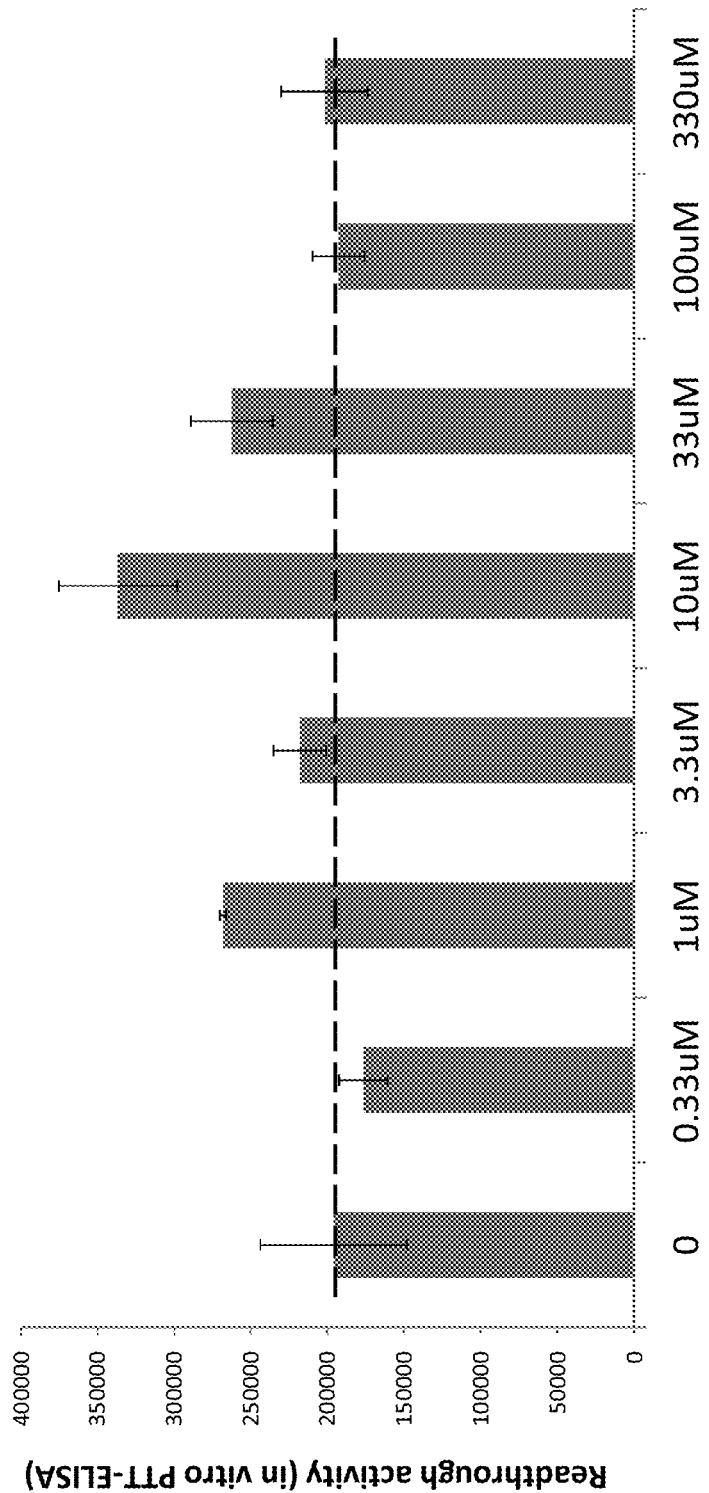

FIG. 12. In vitro readthrough activity of GJ-072 demonstrated by PTT-ELISA assay.

Figure 13:
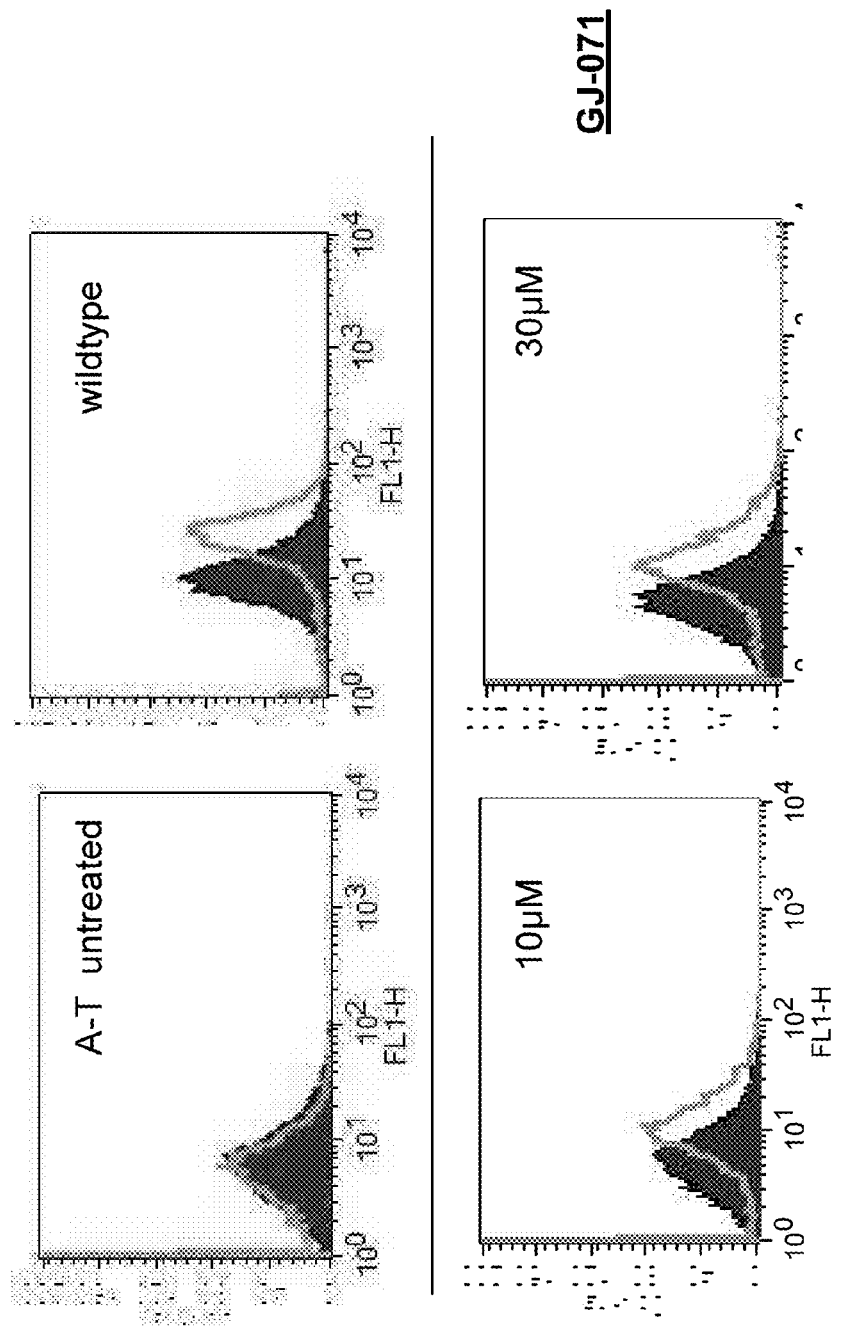

FIG. 13. Readthrough activity of GJ-071 using FCATMs1981 in A-T cells with homozygous TGA mutation. After 4 days of compound treatment, A-T cells were irradiated for 10Gy and collected for assaying. Wildtype cells (WT) were used as positive assay control. The increased fluorescent intensity after IR indicated the restoration of ATM auto-phosphorylation of at Serine 1981.

Figure 14:
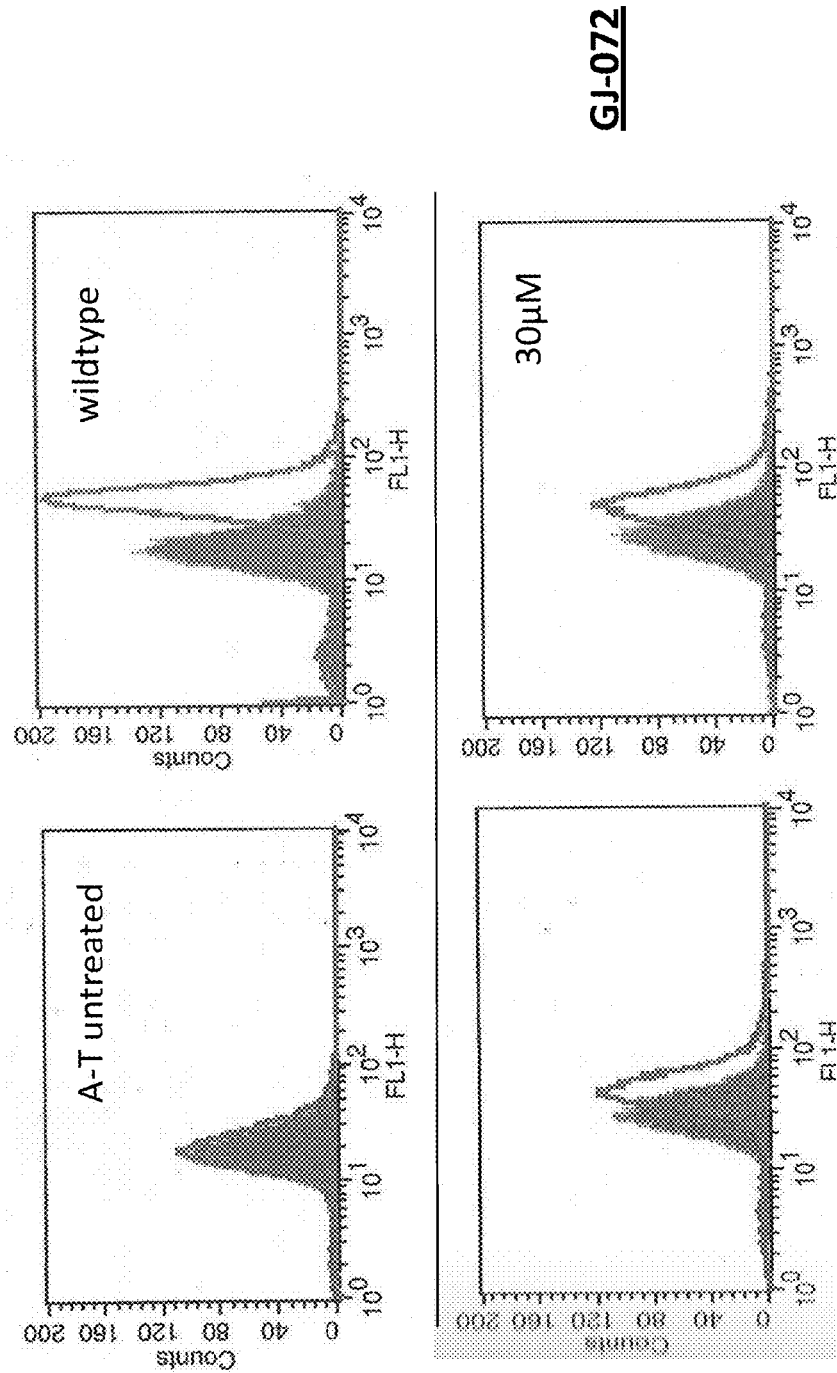

FIG. 14. Readthrough activity of GJ-072 using FCATMs1981 in A-T cells with homozygous TGA mutation. After 4 days of compound treatment, A-T cells were irradiated for 10Gy and collected for assaying. WT cells were used as positive assay control. The increased fluorescent intensity after IR indicated the restoration of ATM auto-phosphoryla-tion of at Serine 1981.

Figure 15:
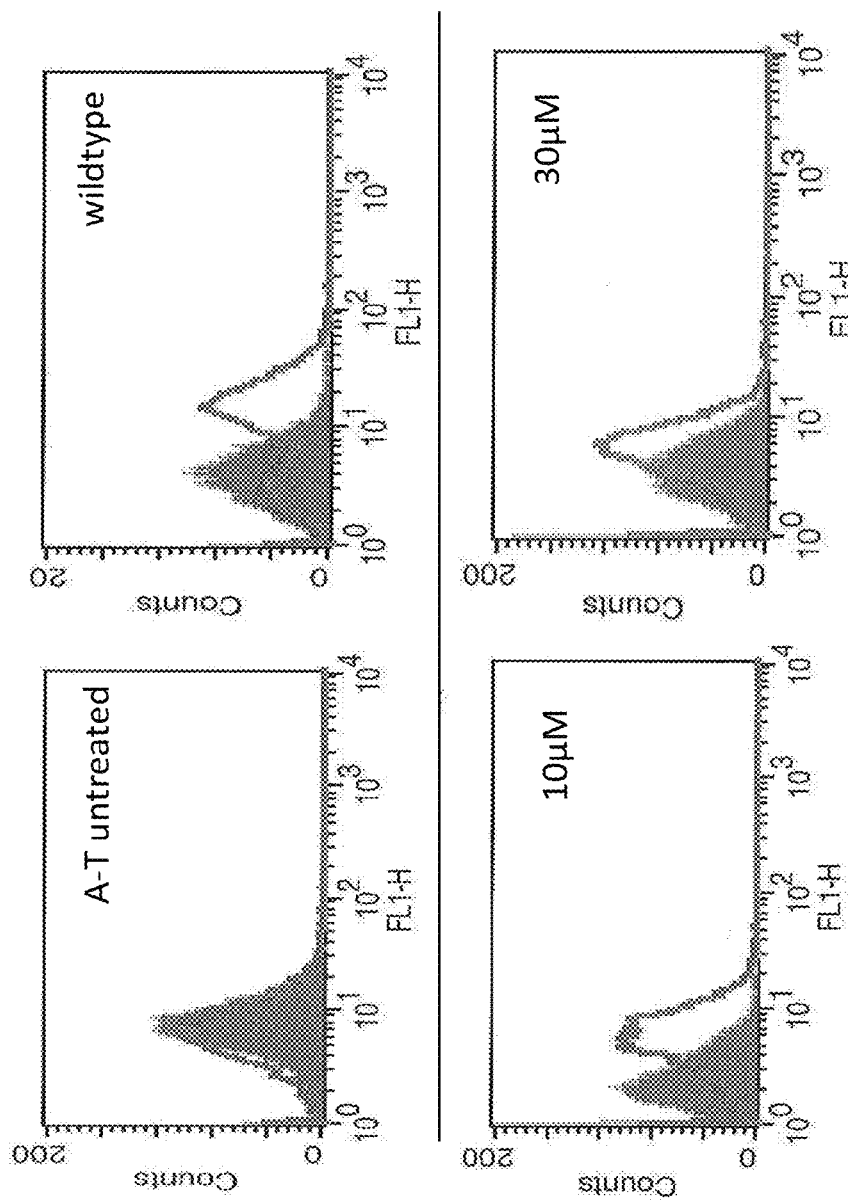

FIG. 15. GJ-071 induced FC-SMC1 pSer966 phosphorylation in A-T LCLs with homozygous TGA mutation. A-T cells were treated for 4 days and ATM kinase activity was assessed using FC-based SMC1-Ser966 phosphorylation. WT cells were used as positive assay control. Right shift of florescent intensity after 10Gy IR indicated the restoration of SMCs966 phosphorylation in the histograms.

Figure 16:
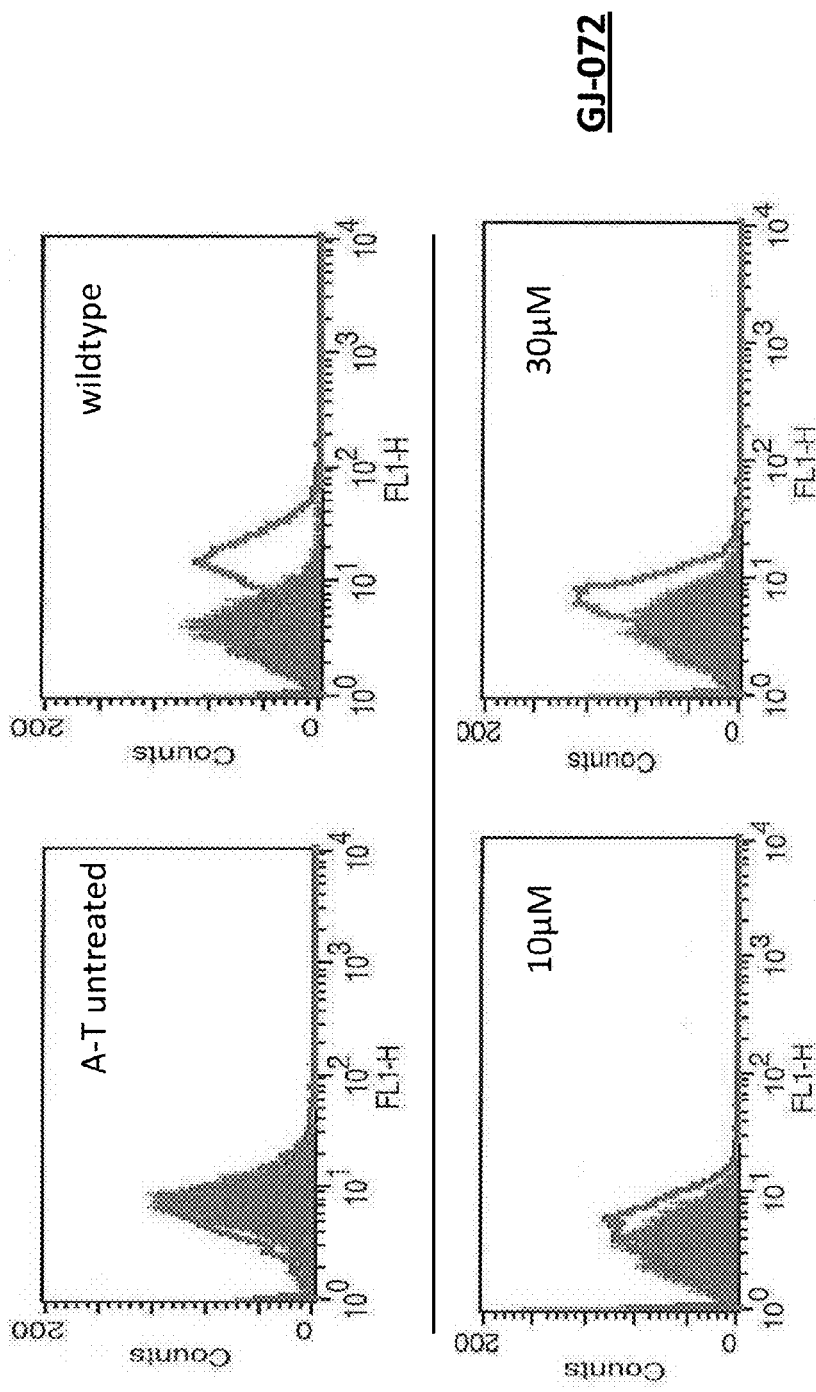

FIG. 16. GJ-072 induced FC-SMC1 pSer966 phosphorylation in A-T LCLs with homozygous TGA mutation. A-T cells were treated for 4 days and ATM kinase activity was assessed using FC-based SMC1-Ser966 phosphorylation. WT cells were used as positive assay control. Right shift of florescent intensity after 10Gy IR indicated the restoration of SMCs966 phosphorylation in the histograms.

Figure 17:
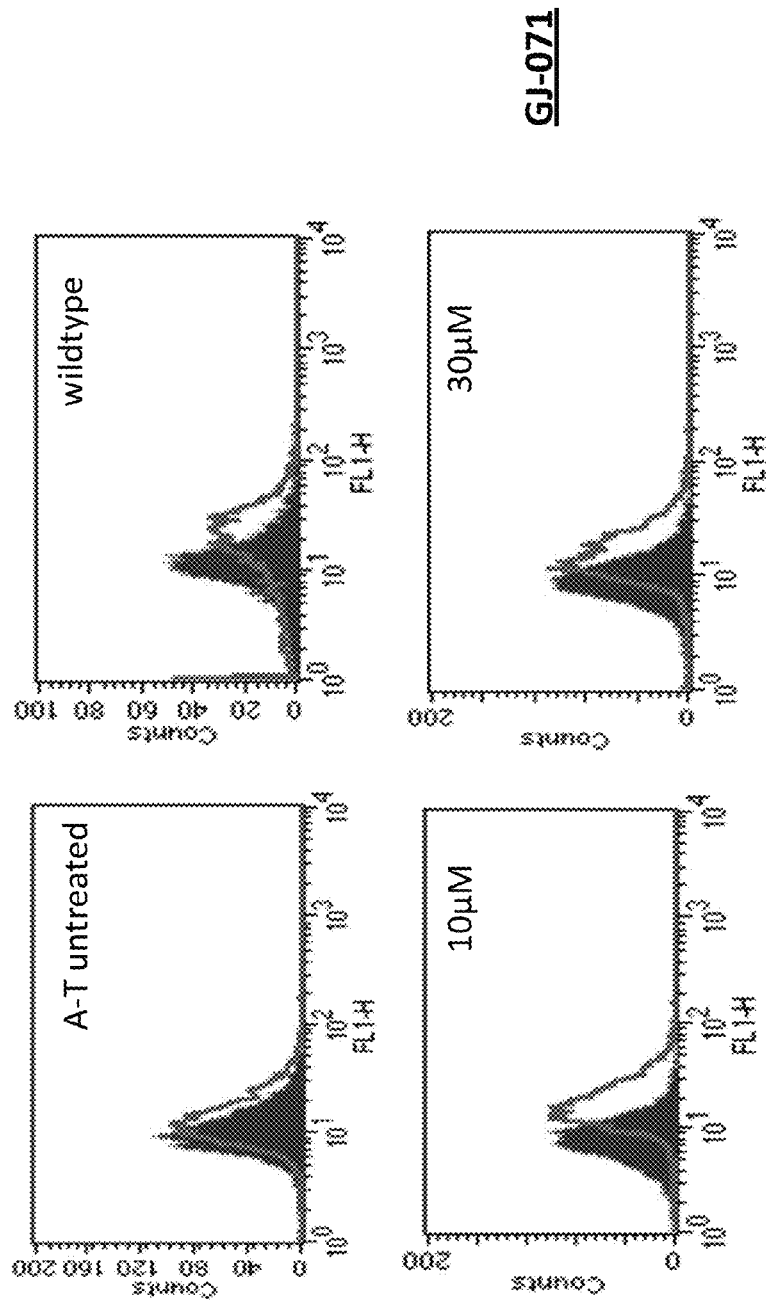

FIG. 17. GJ-071 induced FC-SMC1 pSer966 phosphorylation in A-T LCLs with homozygous TAG mutation. A-T cells were treated for 4 days and ATM kinase activity was assessed using FC-based SMC1-Ser966 phosphorylation. WT cells were used as positive assay control. Right shift of florescent intensity after 10Gy IR indicated the restoration of SMCs966 phosphorylation in the histograms.

Figure 18:
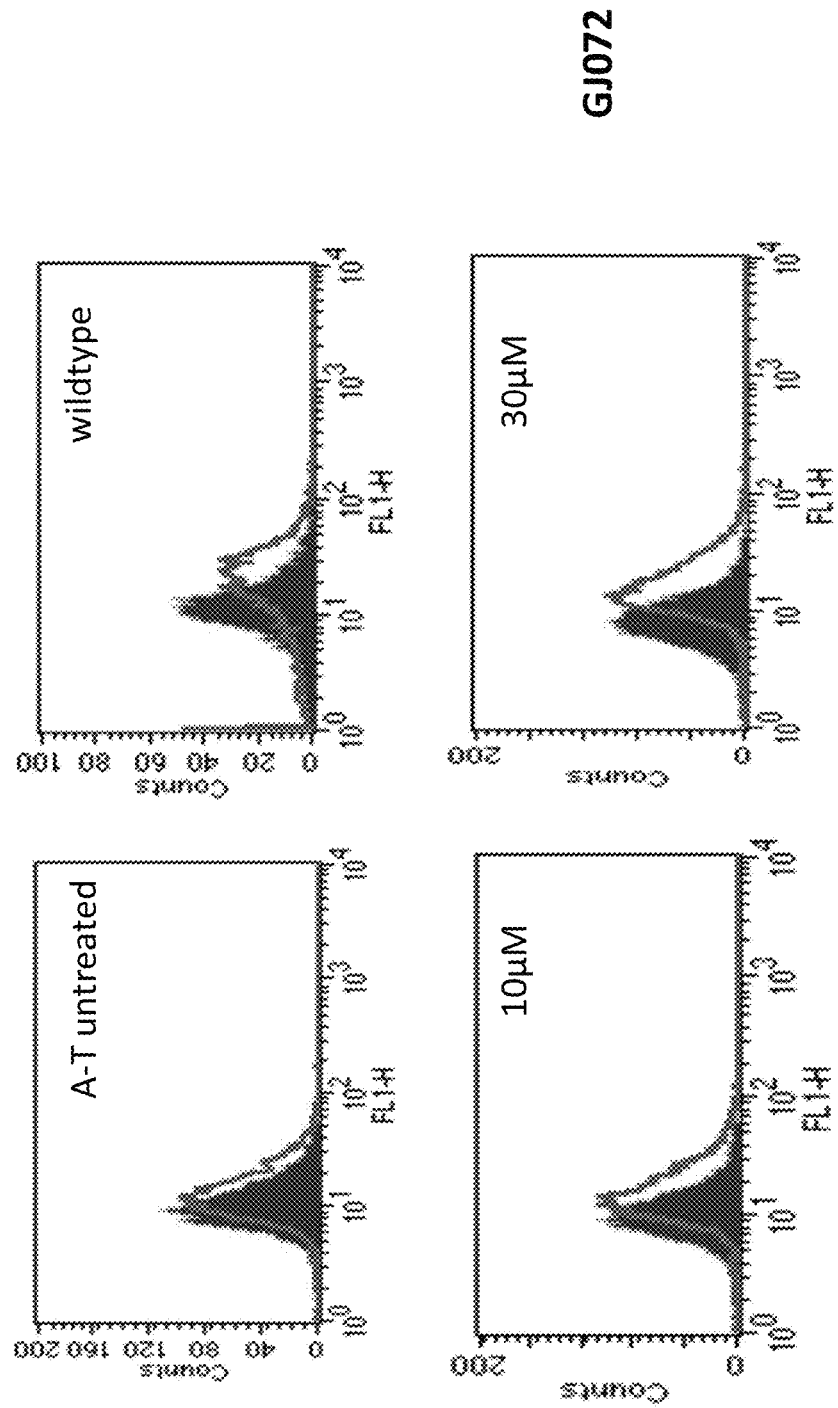

FIG. 18. GJ-072 induced FC-SMC1 pSer966 phosphorylation in A-T LCLs with homozygous TAG mutation. A-T cells were treated for 4 days and ATM kinase activity was assessed using FC-based SMC1-Ser966 phosphorylation. WT cells were used as positive assay control. Right shift of florescent intensity after 10Gy IR indicated the restoration of SMCs966 phosphorylation in the histograms.

Figure 19:
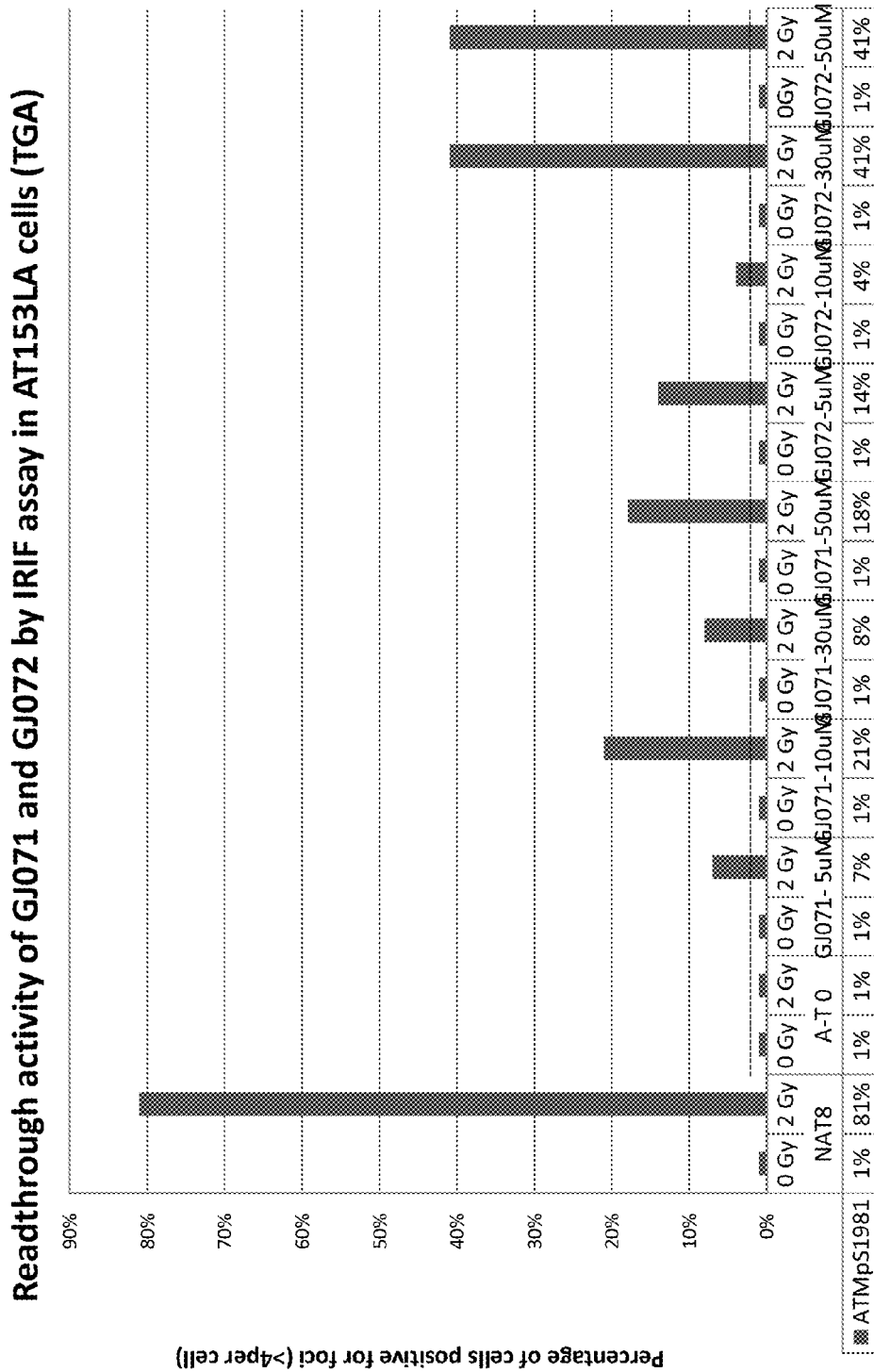

FIG. 19. Measurement of readthrough activity of GJ-071 and GJ-072 using ATMs1981 foci formation assay (IRIF-ATMs1981) assay in A-T cells with homozygous TGA mutation. After 4 days of compound treatment of the compounds, A-T cells were irradiated for 2Gy and collected for assaying. WT cells were used as positive assay control. The increased ATMs 1981 foci positive cell population was indicated. Both compounds induced ATMs1981 foci formation in A-T cells.

Figure 20:
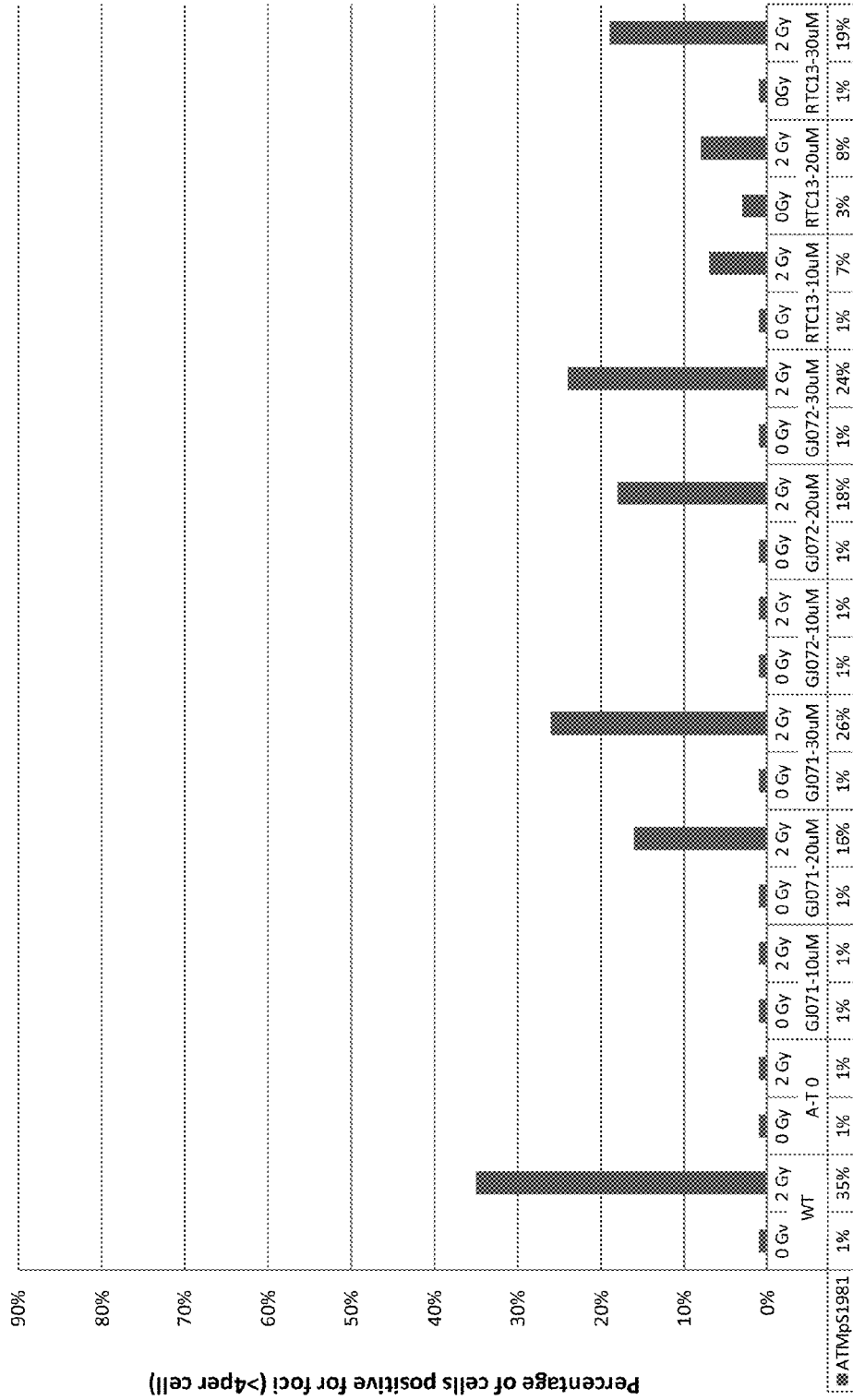

FIG. 20. Measurement of readthrough activity of GJ-071 and GJ-072 using ATMs1981 foci formation assay (IRIF-ATMs1981) assay in A-T cells with homozygous TAG mutation. After 4 days of compound treatment of the compounds, A-T cells were irradiated for 2Gy and collected for assaying. WT cells were used as positive assay control. The increased ATMs1981 foci positive cell population was indicated. Both compounds induced ATMs1981 foci formation in A-T cells.

Figure 21:
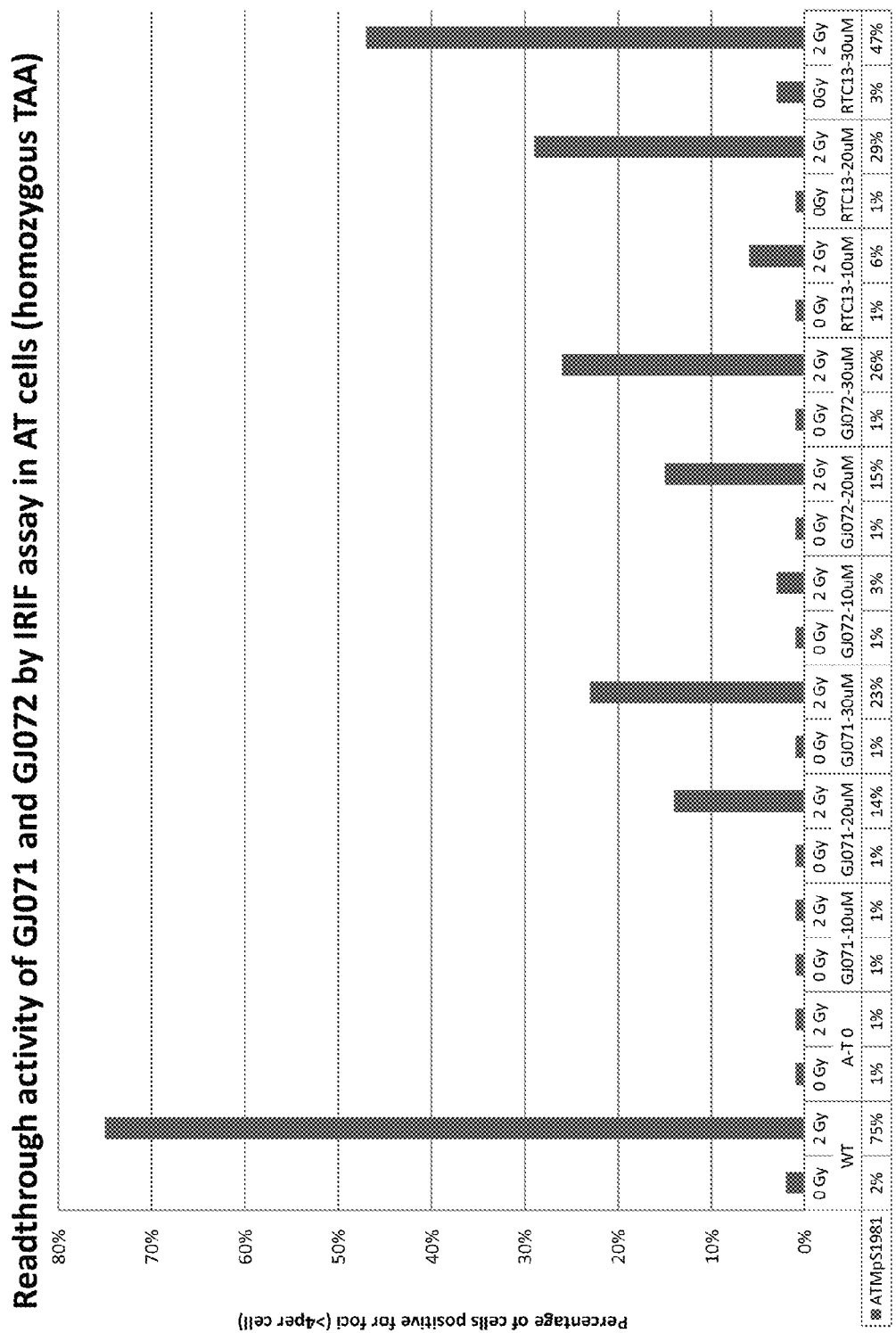

FIG. 21. Measurement of readthrough activity of GJ-071 and GJ-072 using ATMs1981 foci formation assay (IRIF-ATMs1981) assay in A-T cells with homozygous TAA mutation. After 4 days of compound treatment of the compounds, A-T cells were irradiated for 2Gy and collected for assaying. WT cells were used as positive assay control. The increased ATMs1981 foci positive cell population was indicated. Both compounds induced ATMs1981 foci formation in A-T cells.

Figure 22:
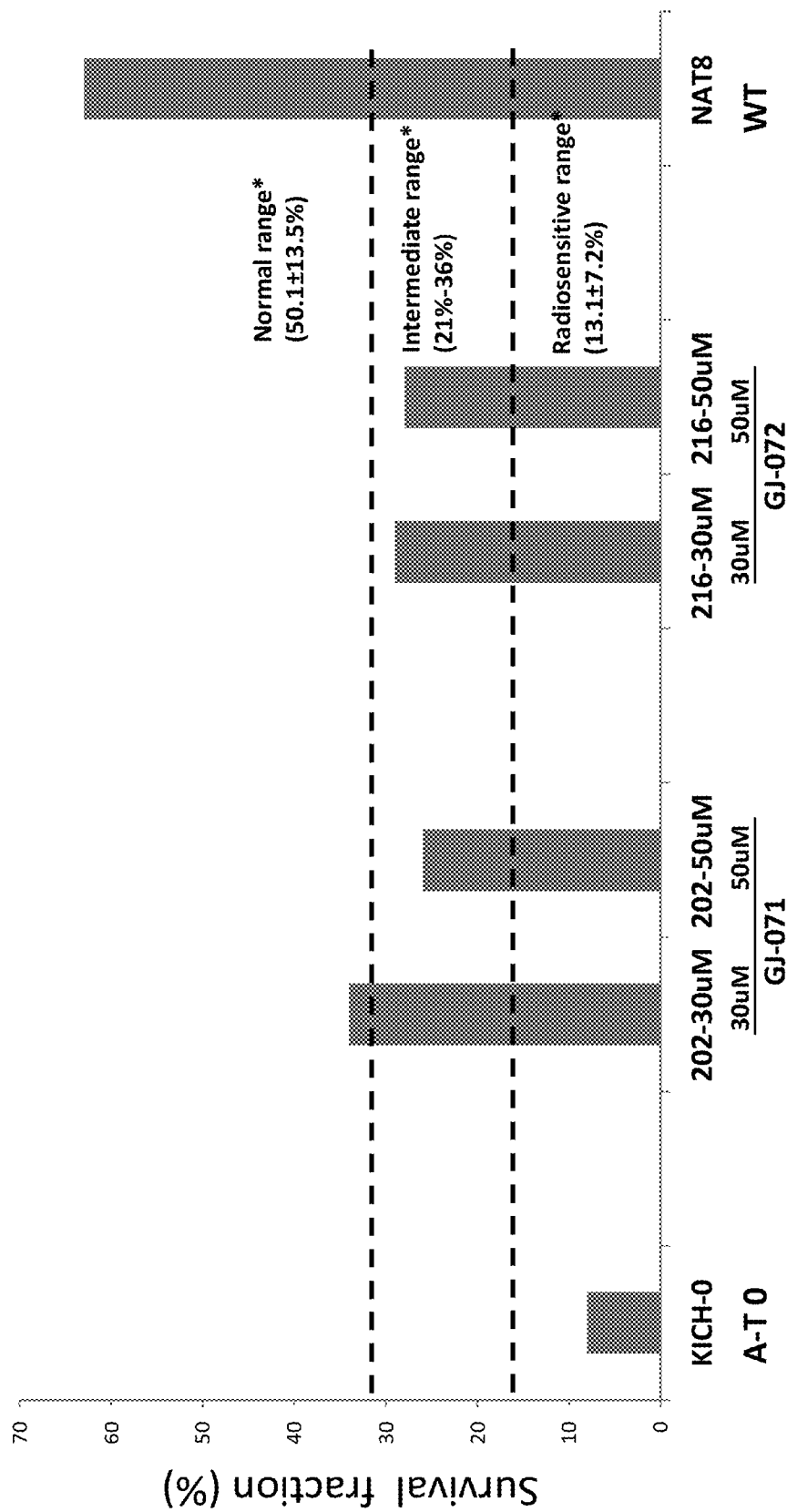

FIG. 22. GJ-071 and GJ-072 abrogated the radio-sensitivity of A-T LCLs with TGA and TAG mutation. AT242LA cells (with TGA and TAG nonsense mutations) were treated with compounds and the CSA was measured. WT cells were used as assay control. Both compounds increased cell survival fractions to "intermediate" range.

Figure 23:
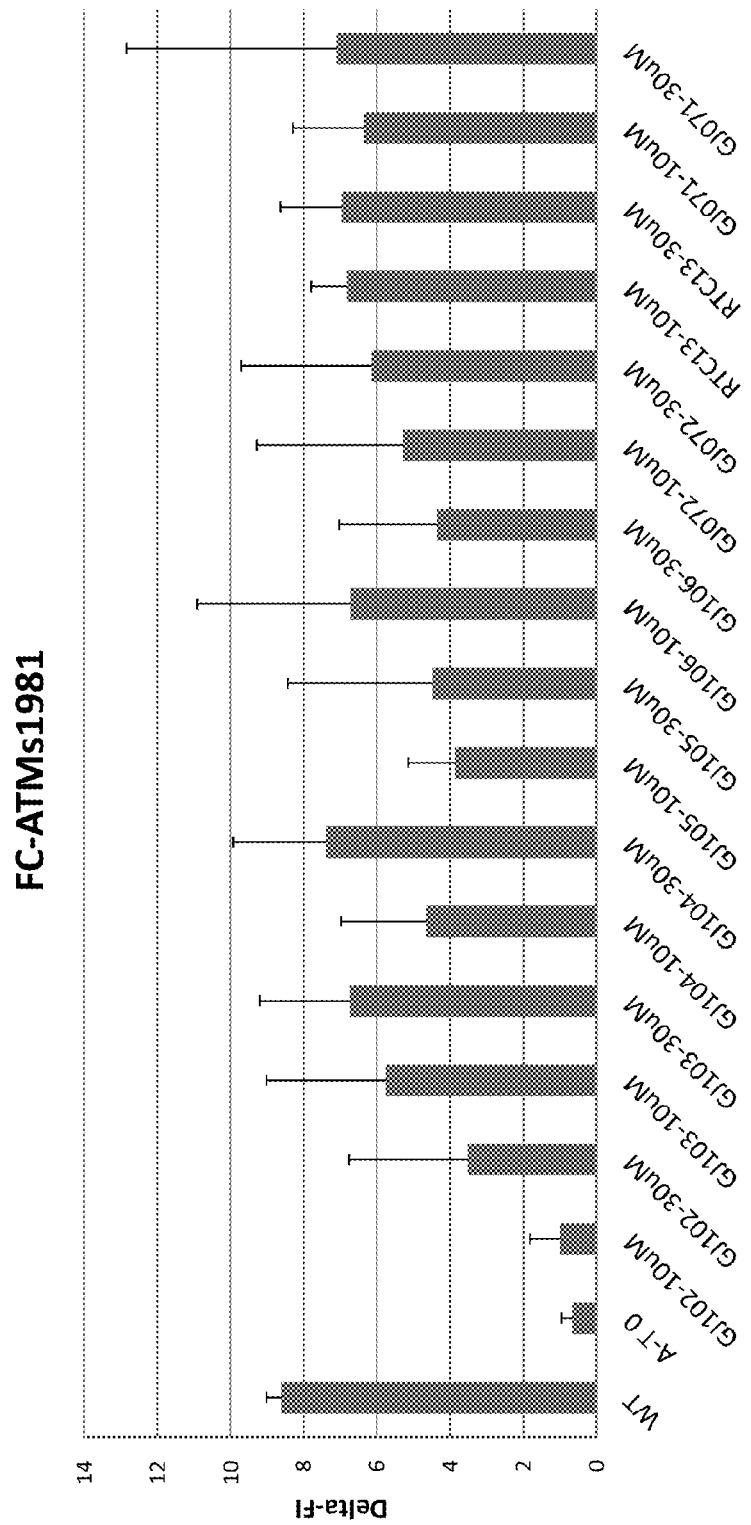

FIG. 23. Readthrough activity of four analogs of GJ-072 in A-T cells with homozygous TGA mutation demonstrated FCATMs1981. Five GJ-072 analogs, GJ102, GJ103, GJ104, GJ105 and GJ106, were tested. GJ071 and GJ072 and RTC13 were included as positive readthrough controls. After 4 days of compound treatment, A-T cells were irradiated for 10Gy and collected for assaying. WT cells were used as positive assay control. The data from 3 sets of independent of experiments were summarized here. The increased Delta-FI (difference of fluorescent intensity before and after IR) indicated the restoration of ATM auto-phosphorylation of at Serine 1981.

Figure 24:
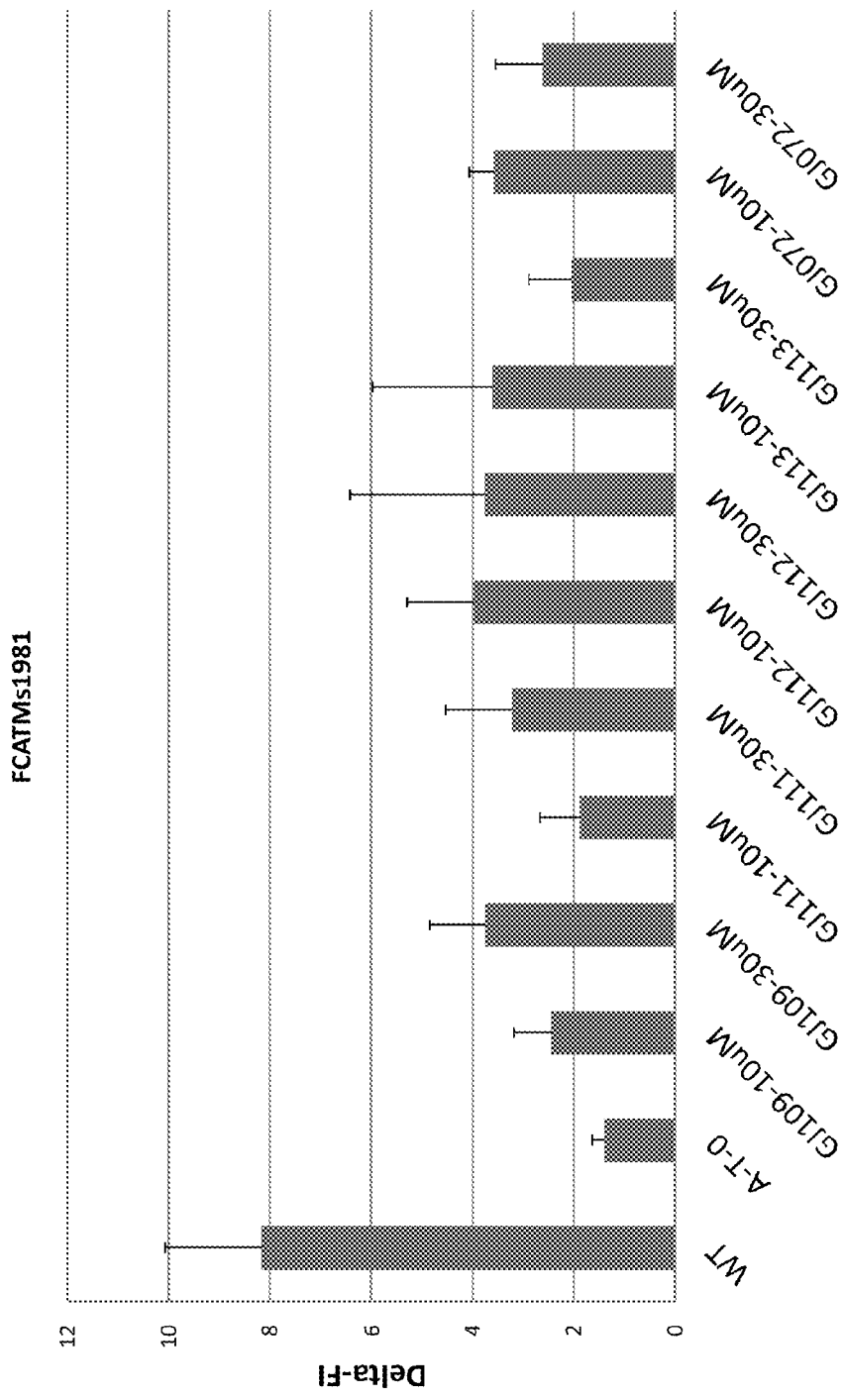

FIG. 24. Readthrough activity of four analogs of GJ-072 in A-T cells with homozygous TGA mutation demonstrated FCATMs1981. Four GJ-072 analogs, GJ109, GJ111, GJ112, GJ113 were tested. GJ-072 was included as positive readthrough control. After 4 days of compound treatment, A-T cells were irradiated for 10Gy and collected for assaying. WT cells were used as positive assay control. The data from 3 sets of independent of experiments were summarized here. The increased Delta-FI (difference of fluorescent intensity before and after IR) indicated the restoration of ATM auto-phosphorylation of at Serine 1981.

Figure 25:
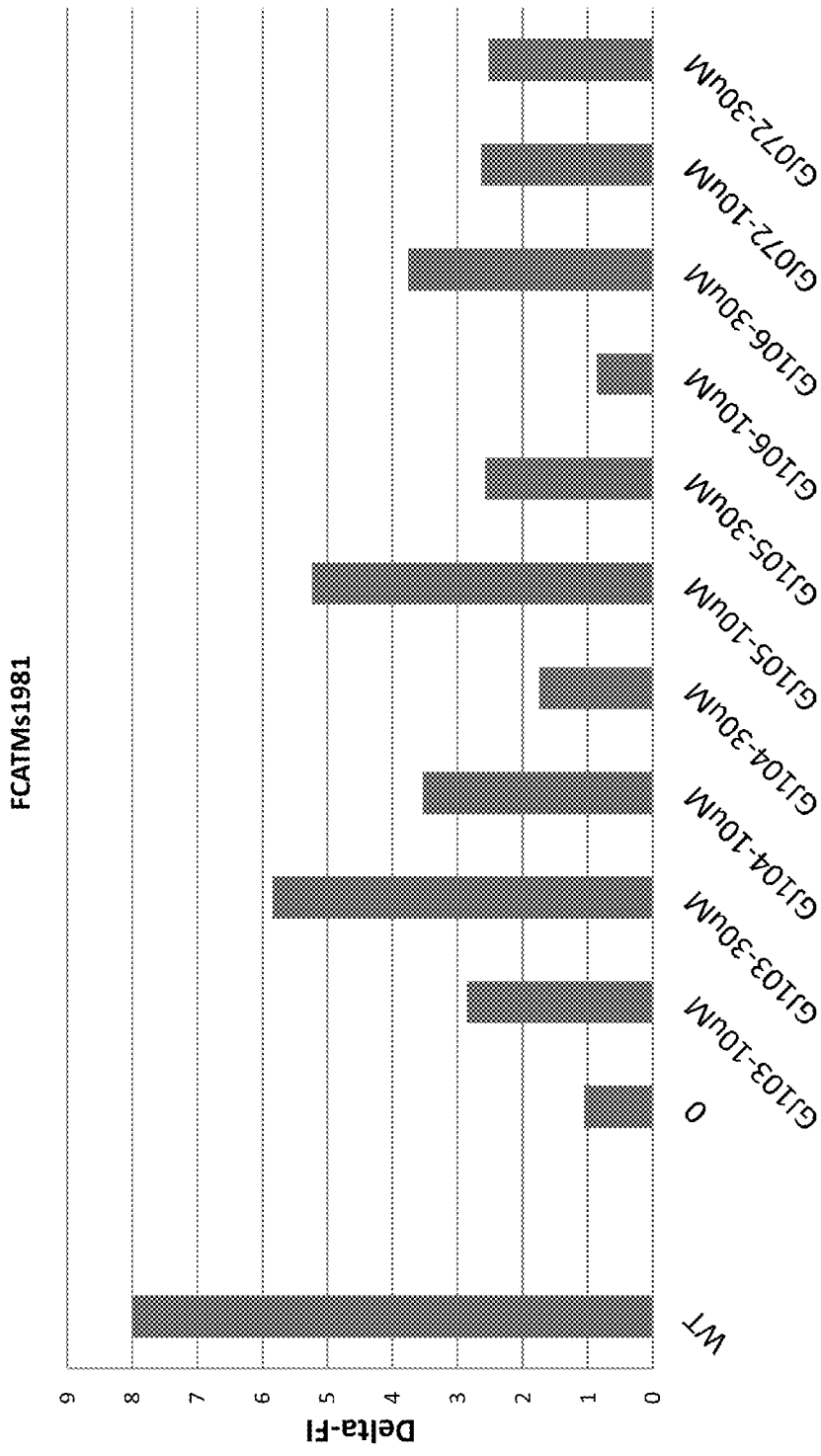

FIG. 25. Readthrough activity of four analogs of GJ-072 in A-T cells with homozygous TAA mutation demonstrated FCATMs1981. Four GJ-072 analogs, GJ103, GJ104, GJ105, GJ106 were tested. GJ-072 was included as positive readthrough control. After 4 days of compound treatment, A-T cells were irradiated for 10Gy and collected for assaying. WT cells were used as positive assay control. The increased Delta-FI (difference of fluorescent intensity before and after IR) indicated the restoration of ATM auto-phosphorylation of at Serine 1981.

Figure 26:
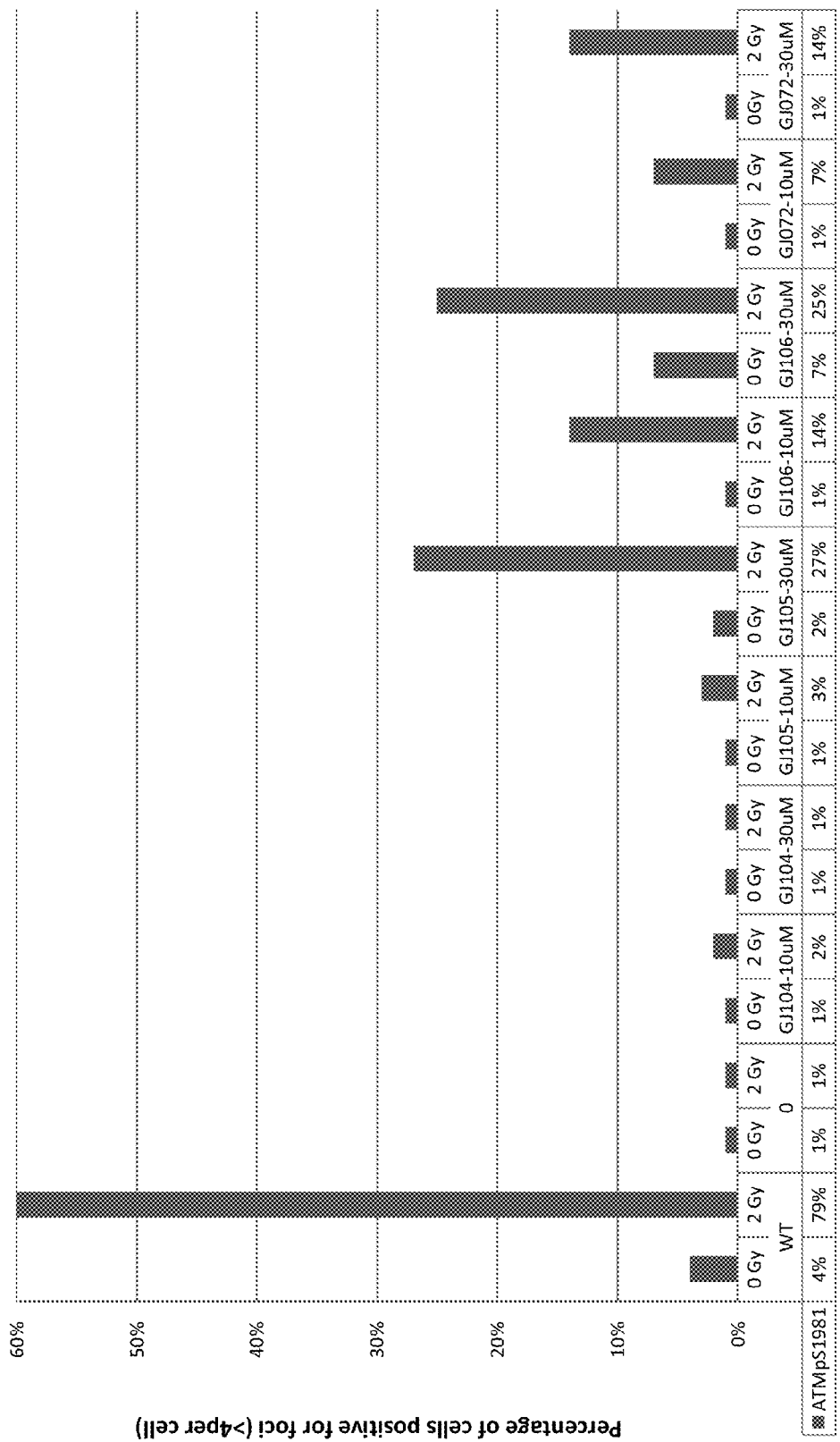

FIG. 26. Measurement of readthrough activity of three GJ-072 analogs using ATMs1981 foci formation assay (IRIF-ATMs1981) assay in A-T cells with homozygous TGA mutation. GJ104, GJ105 and GJ106 were tested. After 4 days of compound treatment of the compounds, A-T cells were irradiated for 2Gy and collected for assaying. WT cells were used as positive assay control. The increased ATMs1981 foci positive cell population was indicated. GJ105 and GJ106 increased ATMs1981 foci formation in A-T cells.

Figure 27:
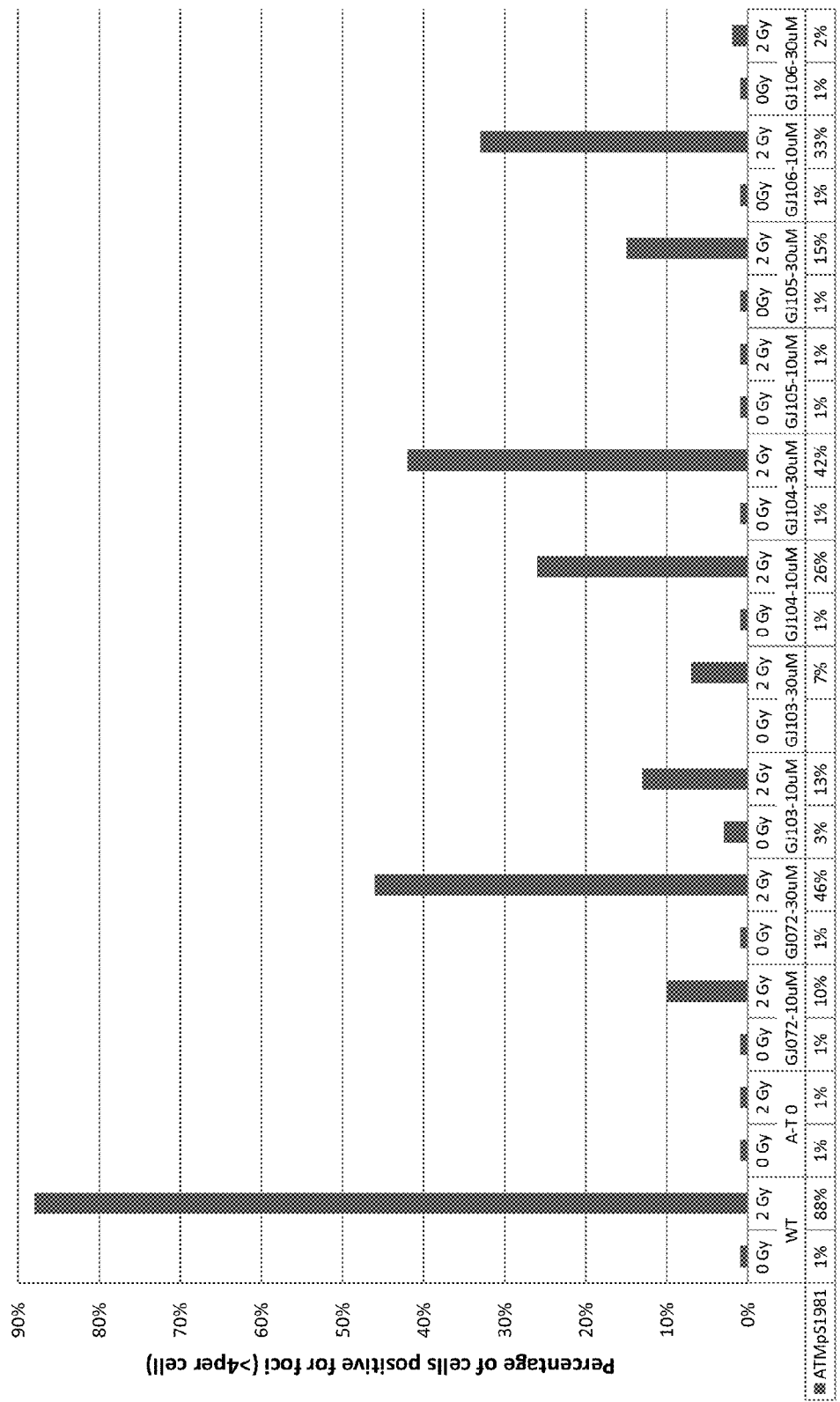

FIG. 27. Measurement of readthrough activity of three GJ-072 analogs using ATMs1981 foci formation assay (IRIF-ATMs1981) assay in A-T cells with homozygous TAG mutation. GJ103, GJ104, GJ105 and GJ106 were tested. After 4 days of compound treatment of the compounds, A-T cells were irradiated for 2Gy and collected for assaying. WT cells were used as positive assay control. The increased ATMs1981 foci positive cell population was indicated.

Figure 28:
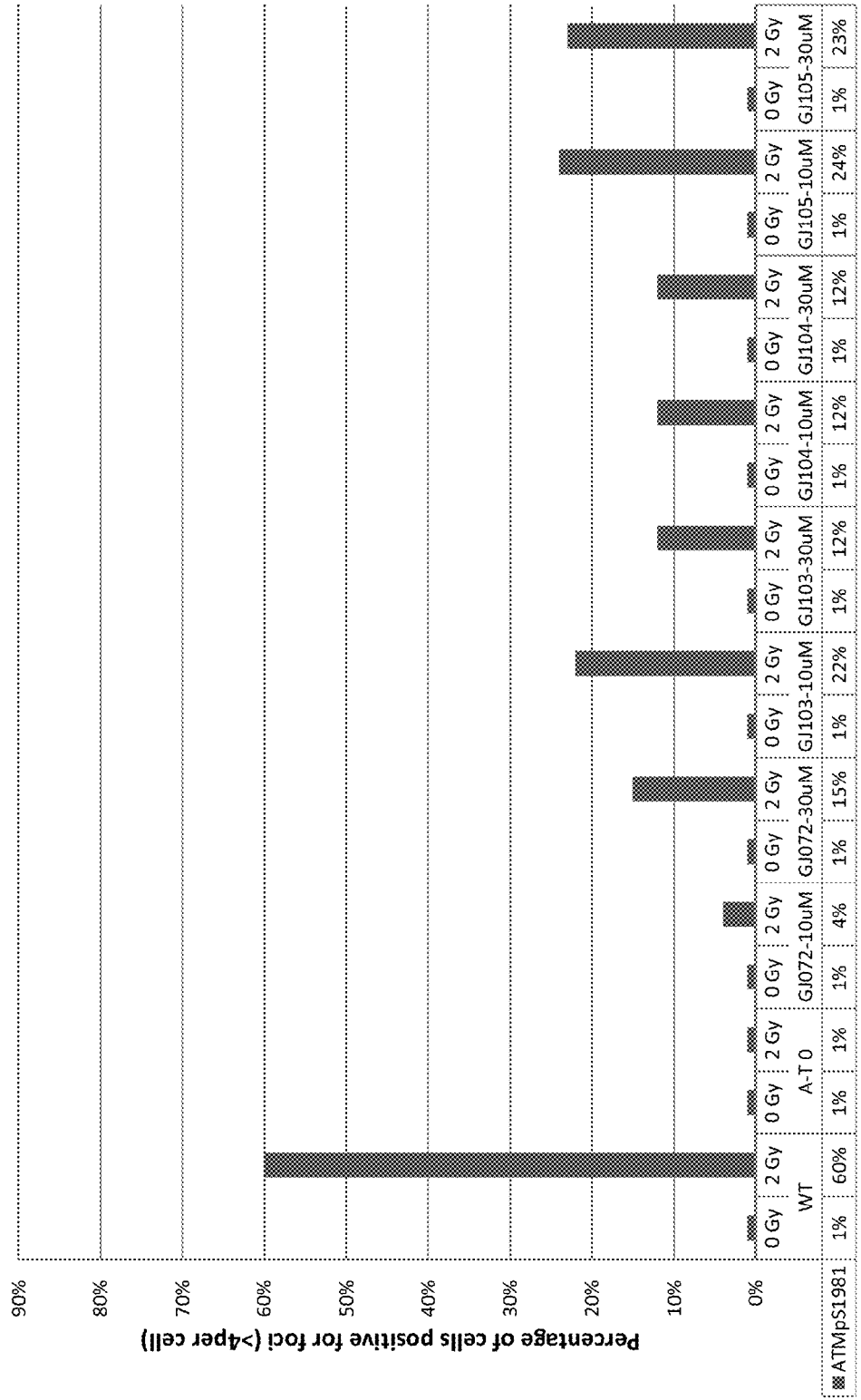

FIG. 28. Measurement of readthrough activity of three GJ-072 analogs using ATMs1981 foci formation assay (IRIF-ATMs1981) assay in A-T cells with homozygous TAA mutation. GJ103, GJ104, and GJ105 were tested. After 4 days of compound treatment of the compounds, A-T cells were irradiated for 2Gy and collected for assaying. WT cells were used as positive assay control. The increased ATMs1981 foci positive cell population was indicated.

FIG. 29. Other two potential readthrough compounds, 204 and 219. a) Structures of 204 and 219. b). Readthrough activity of 204 and 219 indicated by FCATMs1981 assay in A-T cells with TGA homozygous mutation after 4 day treatment.

FIG. 30. Cytotoxicity of some GJ-072 analogs in A-T cells. Cells were treated for 3 days before assaying.

FIG. 31. Four GJ072 analogs induced ATMs1981 IRIF in cells with homozygous TGA A stop codon. AT153LA cells were treated with RTCs for 4 days and followed by IRIF. These data were combined from 4 independent experiments. *: $P \leq 0.05$ as compared untreated A-T control.

FIG. 32. GJ072 analogs induced ATMs1981 IRIF in cells with homozygous TAA G stop codon. AT185LA cells were treated with RTCs for 4 days and followed by IRIF. These data were combined from 2 independent experiments. *: $P \leq 0.05$ as compared untreated A-T control.

FIG. 33. Cytotoxicity of GJ071, GJ072 and some of GJ072 analogs. AT153LA cells were treated with RTC for 4 days at various concentrations as indicated. Cytotoxicity was measured using XTT assay according to the regular protocol.

DETAILED DESCRIPTION

| Abbreviations | |
|---|---|
| Abbreviation | Meaning |
| A-T | ataxia-telangiectasia |
| h | hours |
| HTS | high-throughput screening |
| IRIF | Ionizing Radiation-Induced Focus |
| kg | kilogram |
| LCL | lymphoblastoid cell line |
| mg | milligram |
| mL | milliliter |
| μg | microgram |
| μL | microliter |
| MTT | 3-(4,5-dimethylthiazol-2-yl)-2,5-diphenyltetrazolium bromide |
| NMR | nuclear magnetic resonance |
| PTC | premature termination codons |
| PTT-ELISA | protein transcription/translation-enzyme-linked immunosorbent assay |
| rt or RT | room temperature |
| RTC | readthrough compound |
| TLC | thin layer chromatography |
| TMS | trimethylsilane |
| UV | ultraviolet |
| WT | wild-type |

Definitions

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

As used throughout this application and the appended claims, the following terms have the following meanings:

"About" preceding a numerical value refers to a range of values ±10% of the value specified.

"Acceptable" with respect to a formulation, composition or ingredient, as used herein, means having no persistent detrimental effect on the general health of the subject being treated.

A "readthrough compound" is one which allows the cellular machinery to read-through nonsense mutations and produce full-length protein(s).

"Alkenyl" means a straight or branched hydrocarbon radical containing from 2-10 carbon atoms and at least one double bond, in another example 2-6 carbon atoms and one or two double bonds. Illustrative examples include, but are not limited to, allyl.

"Alkoxy" means an —OR group where R is alkyl, as defined herein. Illustrative examples include, but are not limited to, methoxy, ethoxy, propoxy, 2-propoxy, butoxy, tert-butoxy, pentyloxy, and hexyloxy.

"Alkoxyalkyl" means an alkyl group substituted with one or two alkoxy groups, as defined herein.

"Alkoxycarbonyl" means an alkoxy group, as defined herein, appended to the parent molecular moiety through a carbonyl group, as defined herein. Illustrative examples of alkoxycarbonyl include, but are not limited to, methoxycarbonyl, ethoxycarbonyl, and tert-butoxycarbonyl.

"Alkyl" means a straight or branched saturated hydrocarbon radical containing from 1-10 carbon atoms, in another example 1-6 carbon atoms. Illustrative examples include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

"Alkylamino" means an —NHR group where R is alkyl, as defined herein.

"Dialkylamino" means an —NRR' group where R and R' are independently alkyl, as defined herein.

"Cycloalkyl" means a monocyclic or fused bicyclic, saturated or partially unsaturated, hydrocarbon radical of three to ten carbon ring atoms. Fused bicyclic hydrocarbon radical includes bridged rings. Unless stated otherwise, the valency of the group may be located on any atom of any ring within the radical, valency rules permitting. One or two ring carbon atoms may be replaced by a —C(O)—, —C(S)—, or —C(=NH)— group. Representative examples of cyclic include but are not limited to:

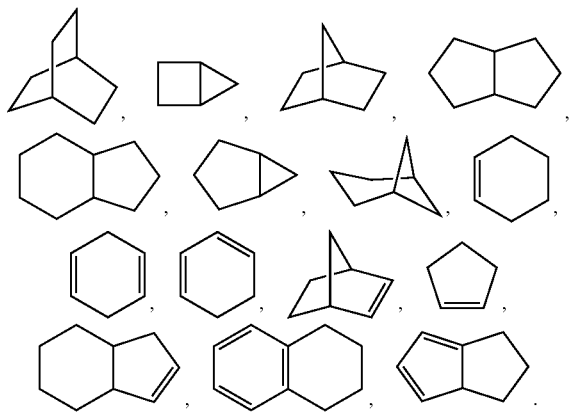

"Aryl" means a monovalent, monocyclic or fused bicyclic hydrocarbon radical of 6 to 12 ring atoms, wherein the ring comprising a monocyclic radical ring is aromatic and wherein at least one of the fused rings comprising a bicyclic radical is aromatic. Fused bicyclic hydrocarbon radical includes bridged ring systems. Unless otherwise stated, the valency of the group may be located on any atom of any ring within the radical, valency rules permitting. For example, the term aryl includes, but is not limited to, phenyl, naphthyl, indanyl (including, for example, indan-5-yl, or indan-2-yl, and the like) or tetrahydronaphthyl (including, for example, tetrahydronaphth-1-yl, or tetrahydronaphth-2-yl, and the like), and the like.

"Arylalkyl" means an alkyl group, as defined herein, substituted with one or two aryl groups as defined herein.

"Haloalkoxy" means an alkoxy group, as defined herein, substituted with one or more halo atoms, in another example by 1, 2, or 3 halo atoms.

"Haloalkyl" means an alkyl group substituted with one or more halo atoms, in another example by 1, 2, 3, 4, 5, or 6 halo atoms, in another example by 1, 2, or 3 halo atoms. Examples include, but are not limited to, trifluoromethyl, chloromethyl, and the like.

"Heteroaryl" means monocyclic, fused bicyclic, or fused tricyclic, radical of 5 to 14 ring atoms containing one or more, in another example one, two, three, or four ring heteroatoms independently selected from —O—, —S(O)$_n$— (n is 0, 1, or 2), —N—, and —N(R$^{200}$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^{200}$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. In particular, when the point of valency is located on a nitrogen, R$^{200}$ is absent. The term heteroaryl includes, but is not limited to, 1,2,4-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), pyrazinyl, pyrimidinyl, pyridazinyl, oxazolyl, isooxazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, methylenedioxyphenyl (including, for example, methylenedioxyphen-5-yl), and the derivatives thereof, or N-oxide or a protected derivative thereof.

"Heteroarylalkyl" means an alkyl group, as defined herein, substituted with one or two heteroaryl groups, as defined herein.

"Heterocycloalkyl" means a saturated or partially unsaturated (but not aromatic) monocyclic group of 3 to 8 ring atoms or a saturated or partially unsaturated (but not aromatic) fused or bridged bicyclic or tricyclic group of 5 to 12 ring atoms in which one or more (specifically one, two, three, or four) ring atoms is a heteroatom independently selected from —O—, —S(O)$_n$— (n is 0, 1, or 2), —N=, and —NH— and the remaining ring atoms being carbon. One or two ring carbon atoms may be replaced by a —C(O)—, —C(S)—, or —C(=NH)— group. Unless otherwise stated, the valency of the group may be located on any atom of any ring within the radical, valency rules permitting. Illustrative examples include lactams, lactones, cyclic imides, cyclic thioimides, cyclic carbamates, More specifically the term heterocycloalkyl includes, but is not limited to, azetidinyl, pyrrolinyl, pyrrolidinyl, 2-oxopyrrolidinyl, 2,5-dioxo-1H-pyrrolyl, 2,5-dioxo-pyrrolidinyl, 2,5-dihydro-1H-pyrrolyl, piperidinyl, 4-piperidonyl, morpholinyl, piperazinyl, 2-oxopiperazinyl, dioxopiperazinyl, pyranyl, tetrahydropyranyl, tetrahydrothiopyranyl, 1,3-dioxinyl, 1,3-dioxanyl, 1,4-di-oxinyl, 1,4-dioxanyl, 2-oxopiperidinyl, thiomorpholinyl, thiamorpholinyl, perhydroazepinyl, pyrazolidinyl, imidazolinyl, imidazolidinyl, 2,4-dioxo-imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, 1,3-oxathianyl, 1,4-oxathiinyl, 1,4-oxathianyl, tetrahydro-1,4-thiazinyl, 2H-1,2-oxazinyl, tetrahydrofuryl, 2,4,6-trioxo-(1H,3H,5H)pyrimidinyl, 4,6-dioxo-2-(1H,5H)thioxodihydropyrimidinyl, 2,4(1H,3H)-di-oxo-dihydropyrimidinyl, trioxanyl, hexahydro-1,3,5-triazinyl, tetrahydrothienyl, tetrahydrofuranyl, pyrazolinyl, 1,3-dioxolyl, 1,3-dioxolanyl, 1,3-dithiolyl, 1,3-dithiolanyl, isoxazolinyl, isoxazolidinyl, oxazolidinonyl, 1,3-oxathiolanyl, 2(3H)-oxo-dihydrothienyl, 2(3H)-oxo-dihydrofuranyl, 1,1-dioxo-tetrahydrothienyl, 2-oxo-1,3-dioxolanyl, 4,5-dihydrooxazolyl, oxiranyl, (1s,4s)-7-oxabicyclo[2.2.1]heptanyl, 2,3-dihydrobenzo[b][1,4]dioxinyl, 4H-1,4-thiazinyl, octahydro-1H-quinolizinyl, and tetrahydropyranyl, and the derivatives thereof and N-oxide or a protected derivative thereof. Additional examples include

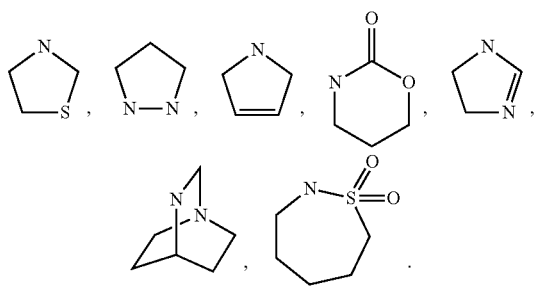

"Heterocycloalkylalkyl" means an alkyl group substituted with one or two heterocycloalkyl groups, as defined herein.

"Hydroxyalkyl" means an alkyl group, as defined herein, substituted with 1, 2, 3, or 4 hydroxy groups.

"Pseudohalo" means a cyano, cyanate (—N═C═O), thiocyanate group (—S═C═N), or azide.

"Thioalkoxy" means an —SR group where R is alkyl, as defined herein.

"Excipient" or "pharmaceutically acceptable excipient" means a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

"Pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined.

"Subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

"Treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

Embodiments

The following paragraphs present a number of embodiments of the compounds disclosed herein. In each instance the embodiment includes both the recited compound(s) as well as a single stereoisomer or mixture of stereoisomers thereof, as well as a pharmaceutically acceptable salt thereof.

A series of 4,5-di-substituted 1,2,4-triazoles bearing a carbonyl- or carboxyl-methylthio substituent at C3, e.g., 1, showed very potent activity. A second set of compounds, 4-(3,4-methylenedioxyphenyl)methyl piperazines with various substituents on the N1 position 2 also showed read-through activity.

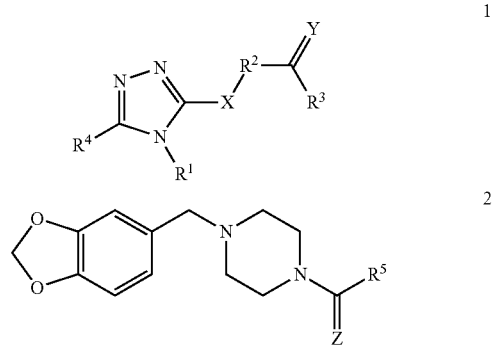

In some or any embodiments, the compound has a structure of formula (3) where A is C—$R^4$ and B and C are both nitrogen and the compound has a structure of (formula 1)

In some or any embodiments of the compound, optionally in combination with any or all of the above various embodiments, $R^4$ is 2-pyridyl for a compound of formula 1 or 3.

In some or any embodiments of the compound, optionally in combination with any or all of the above various embodiments, $R^1$ is 3-methoxyphenyl for a compound of formula 1 or 3.

In some or any embodiments of the compound, optionally in combination with any or all of the above various embodiments, $R^3$ is NH-phenyl for a compound of formula 1 or 3.

In some or any embodiments of the compound, optionally in combination with any or all of the above various embodiments, $R^2$ is —$CH_2$— for a compound of formula 1 or 3.

In some or any embodiments of the compound, optionally in combination with any or all of the above various embodiments, X is sulfur for a compound of formula 1 or 3.

In some or any embodiments of the compound, optionally in combination with any or all of the above various embodiments, Y is oxygen for a compound of formula 1 or 3.

In some or any embodiments of the compound, optionally in combination with any or all of the above various embodiments, the compound is

GJ-103 or a salt thereof, which can be

GJ-103 salt or another pharmaceutically acceptable salt.

In some or any embodiments, the compound is any of the compounds below or a salt thereof:

GJ-001

GJ-002

GJ-003

GJ-004

GJ-005

GJ-006

GJ-007

GJ-008

-continued
GJ-009
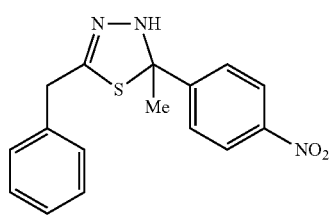
GJ-010
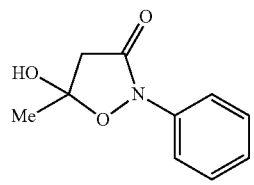
GJ-011
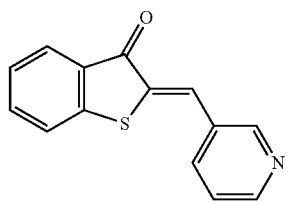
GJ-012
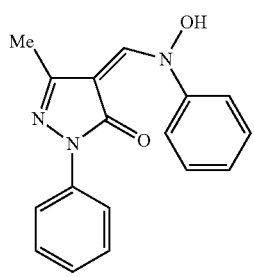
GJ-013
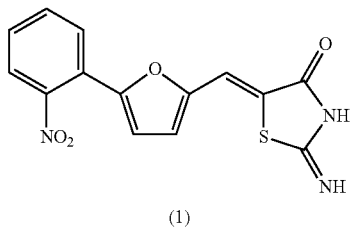
(1)
GJ-014
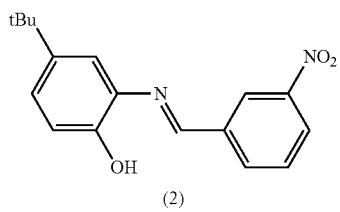
(2)
GJ-015
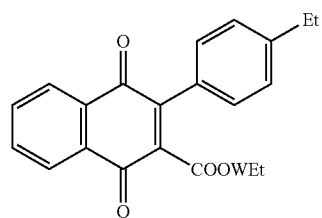
-continued
GJ-016
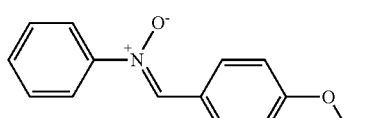
GJ-017
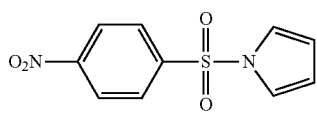
GJ-018
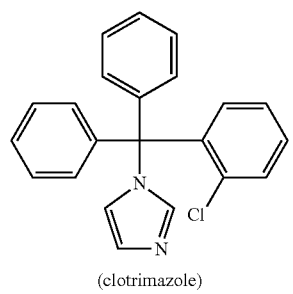
(clotrimazole)
GJ-019
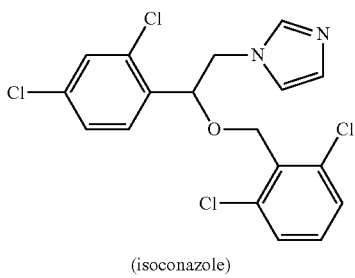
(isoconazole)
GJ-020
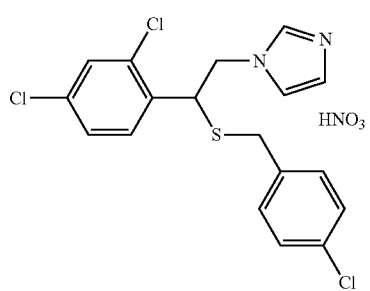
(sulconazole nitrate)
GJ-022
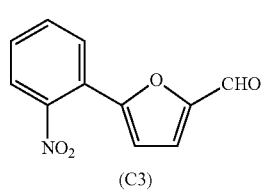
(C3)
GJ-023
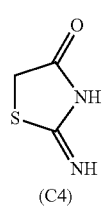
(C4)

-continued (BA1-7a) GJ-024

(BB1-9f) GJ-025

(BC1-7b) GJ-026

(BD1-7c) GJ-027

(BZ1-9e) GJ-028

(BA3-7j) GJ-029

(BA4-7d) GJ-029

(BA5-7e) GJ-030

(BC3-7q) GJ-032

(BC6-7m) GJ-033

(BC7-7n) GJ-034

(BA8-7h) GJ-035

(BA9-7i) GJ-036

(C1) GJ-037

-continued
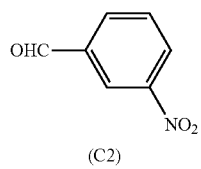
(C2) GJ-038
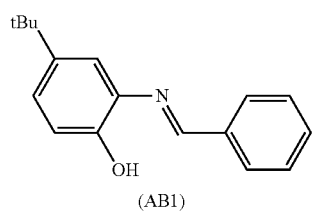
(AB1)
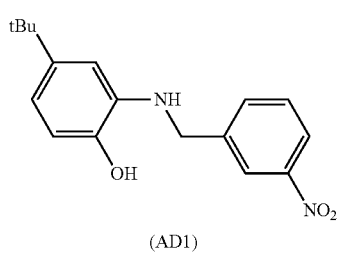
(AD1) GJ-040
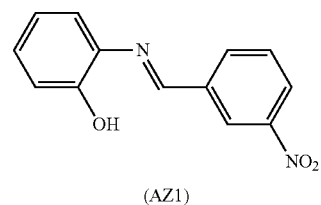
(AZ1) GJ-041
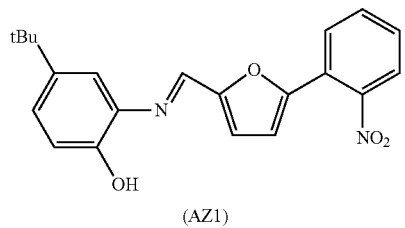
(AZ1) GJ-042
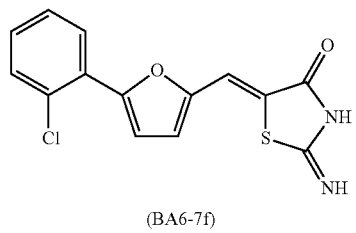
(BA6-7f) GJ-043
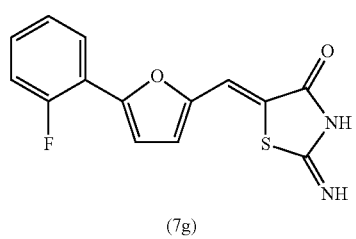
(7g) GJ-044
-continued
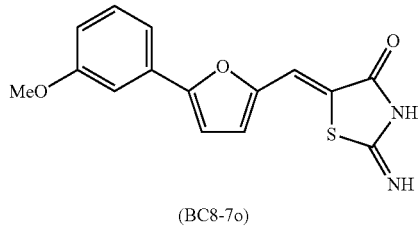
(BC8-7o) GJ-045
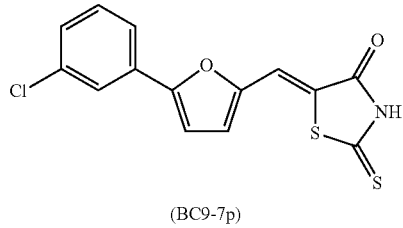
(BC9-7p) GJ-046
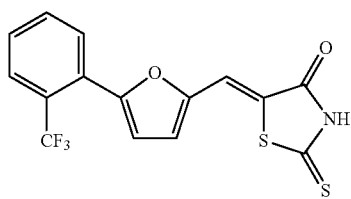
(7k) GJ-047
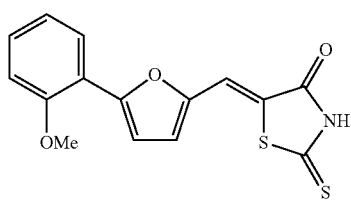
(7l) GJ-048
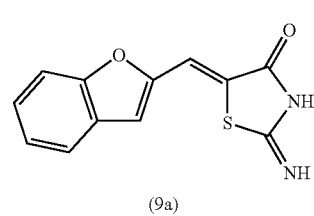
(9a) GJ-049
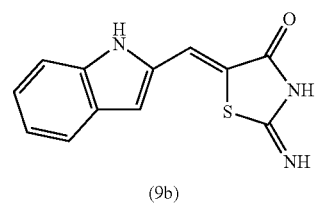
(9b) GJ-050
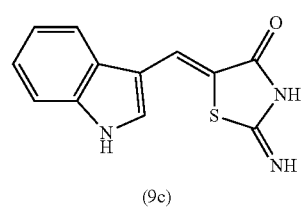
(9c) GJ-051

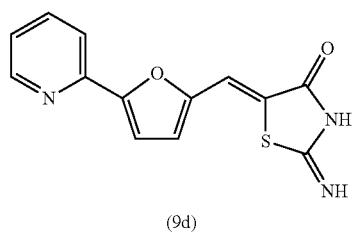
(9d) GJ-052
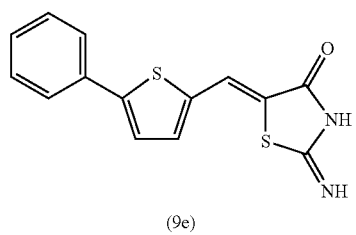
(9e) GJ-053
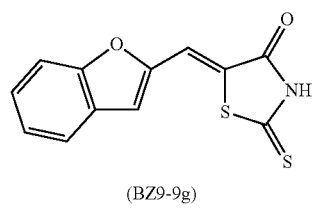
(BZ9-9g) GJ-054
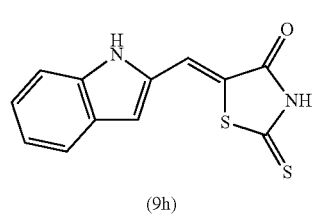
(9h) GJ-055
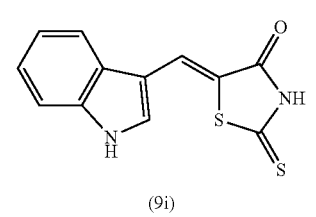
(9i) GJ-056
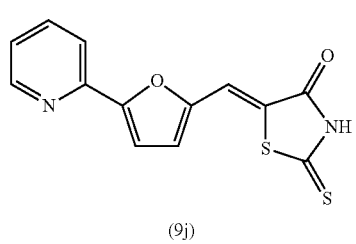
(9j) GJ-057
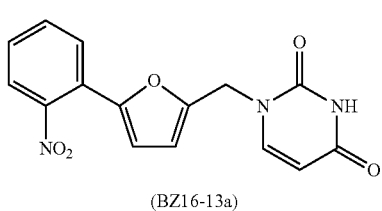
(BZ16-13a) GJ-058
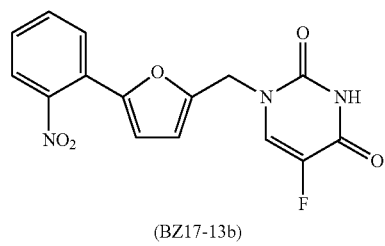
(BZ17-13b) GJ-059
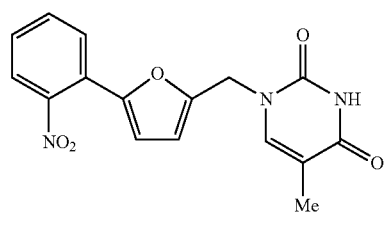
(13c) GJ-060
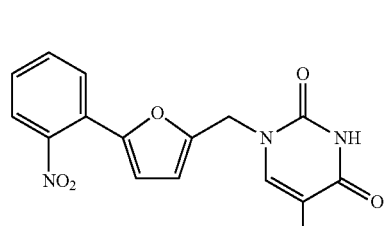
(BZ26-13d) GJ-061
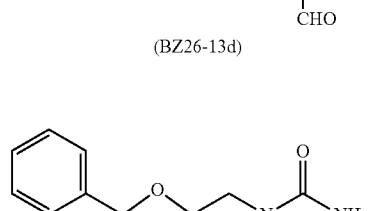
(BZ24-13e) GJ-062
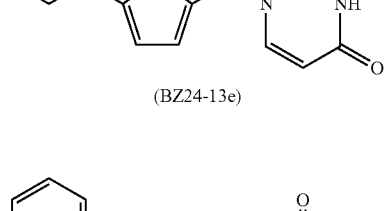
(BZ25-13f) GJ-063
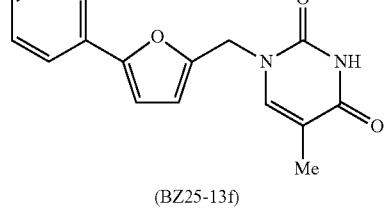
(BZ22-13g) GJ-064

-continued
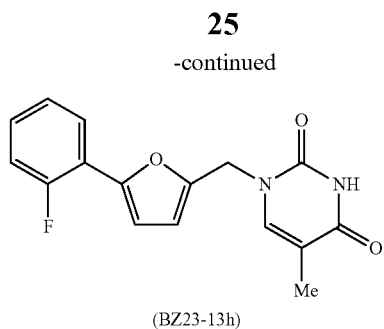
(BZ23-13h)
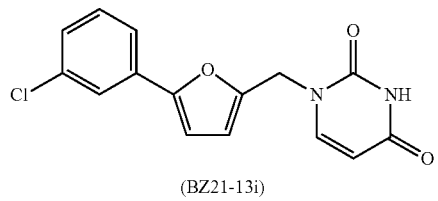
(BZ21-13i)
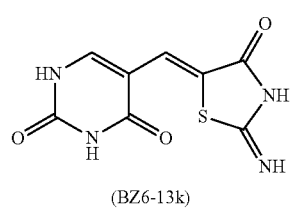
(BZ6-13k)
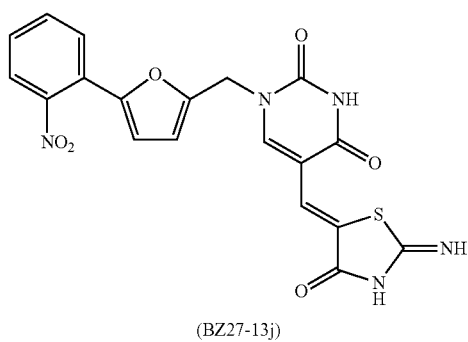
(BZ27-13j)
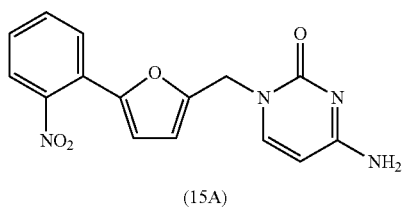
(15A)
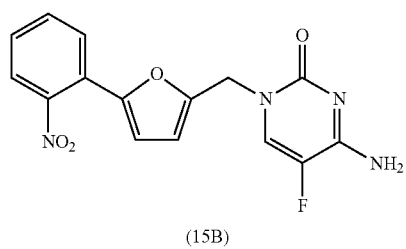
(15B)
-continued
GJ-065
GJ-066
GJ-067
GJ-068
GJ-069
GJ-070
GJ-071
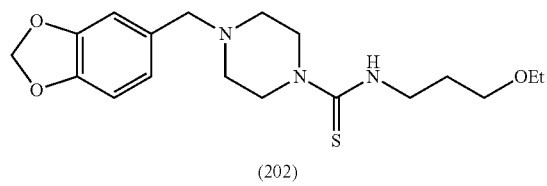
(202)
GJ-072
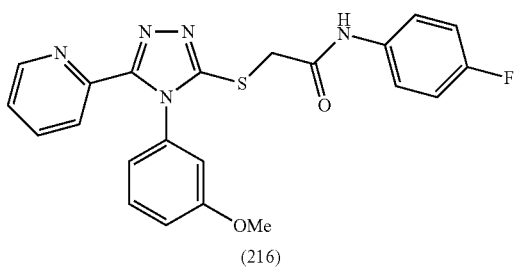
(216)
GJ-073
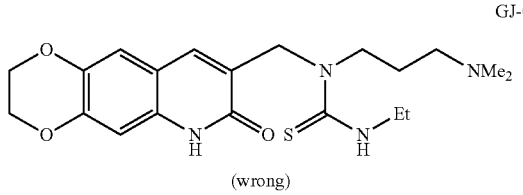
(wrong)
GJ-074
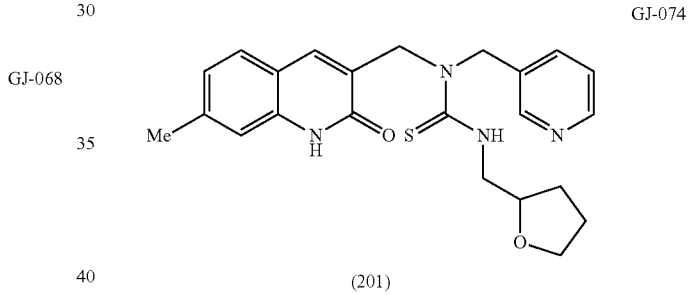
(201)
GJ-075
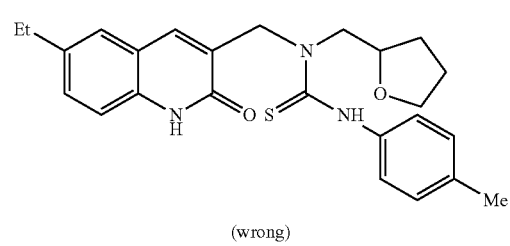
(wrong)
GJ-076
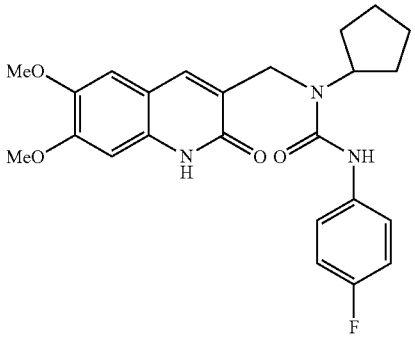
(206)

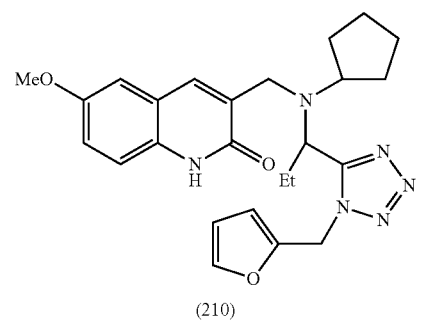
(210) GJ-077
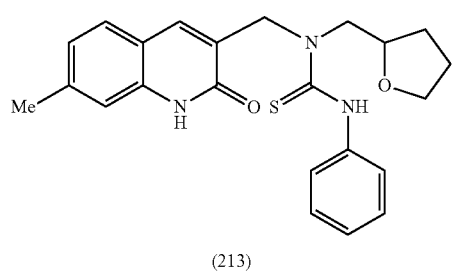
(213) GJ-078
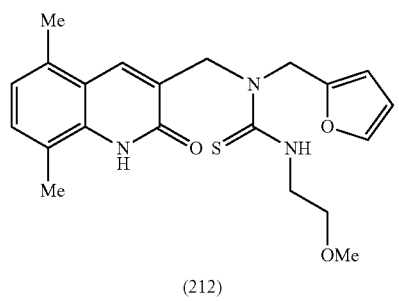
(212) GJ-079
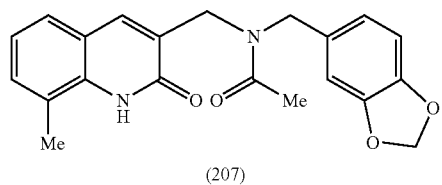
(207) GJ-080
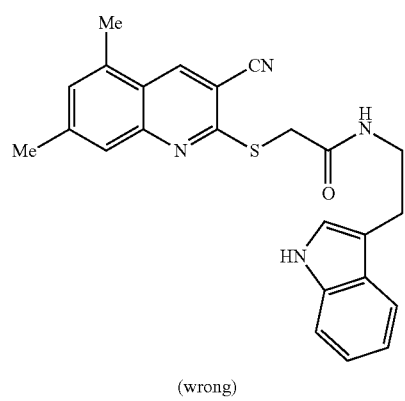
(wrong) GJ-081
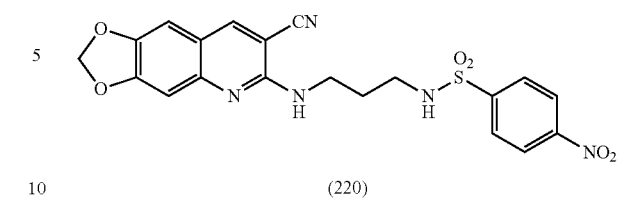
(220) GJ-082
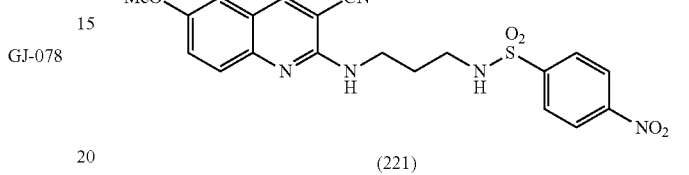
(221) GJ-083
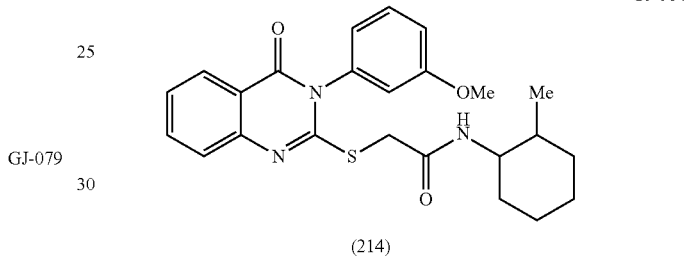
(214) GJ-084
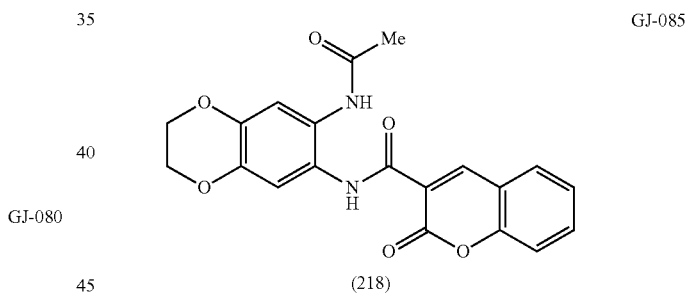
(218) GJ-085
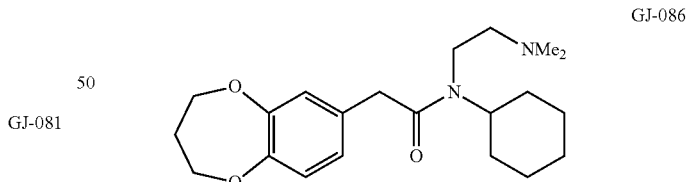
(222) GJ-086
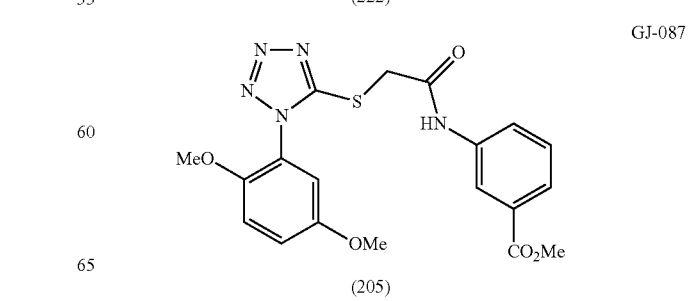
(205) GJ-087

-continued
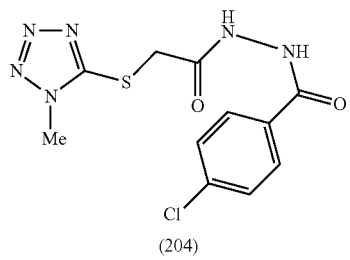
(204) GJ-088
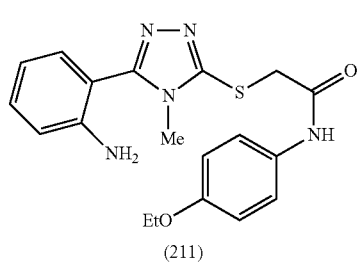
(211) GJ-089
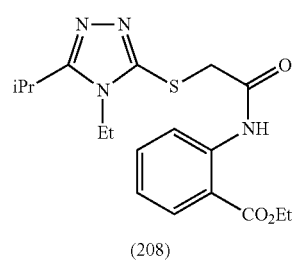
(208) GJ-090
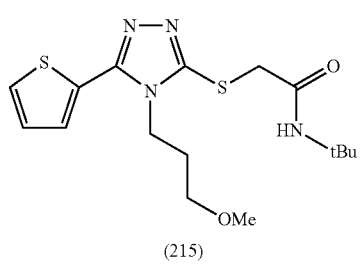
(215) GJ-091
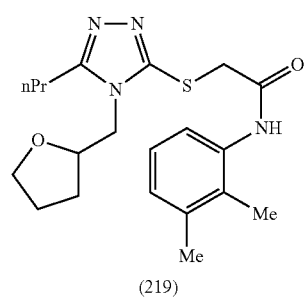
(219) GJ-092
-continued
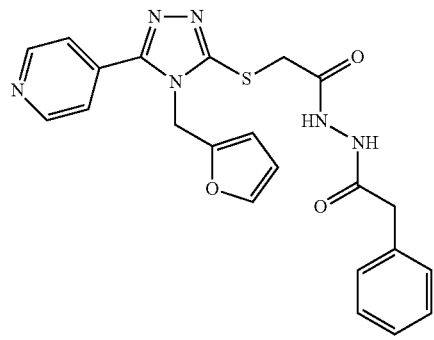
(209) GJ-093
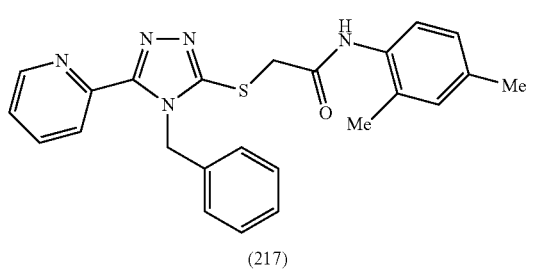
(217) GJ-094
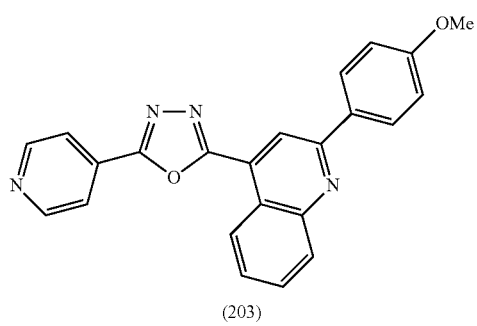
(203) GJ-095
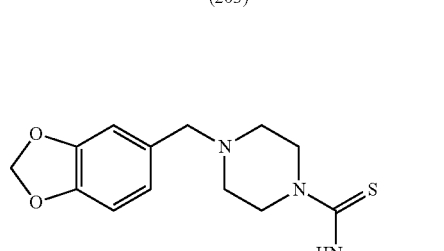
(RT-08-02) GJ-096
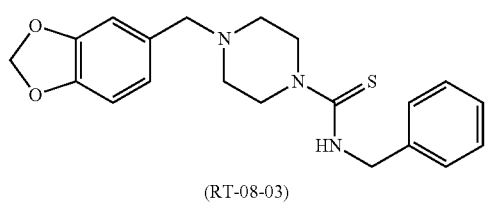
(RT-08-03) GJ-097

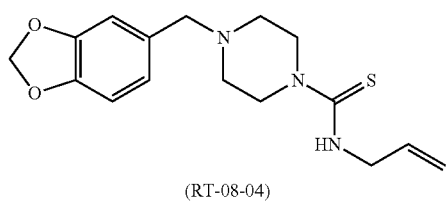
(RT-08-04)
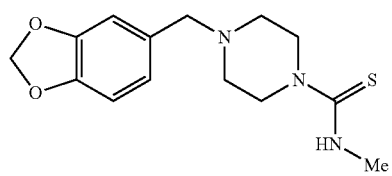
(RT-08-05)
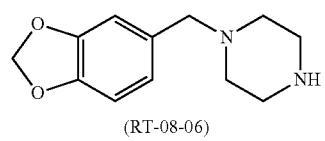
(RT-08-06)
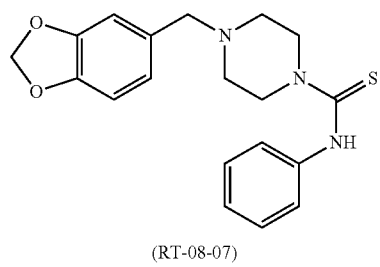
(RT-08-07)
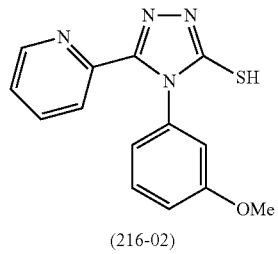
(216-02)
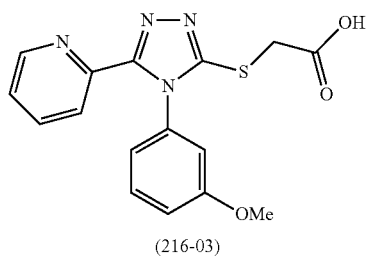
(216-03)
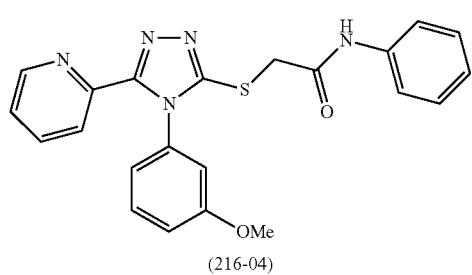
(216-04)
GJ-098
GJ-099
GJ-100
GJ-101
GJ-102
GJ-103
GJ-104
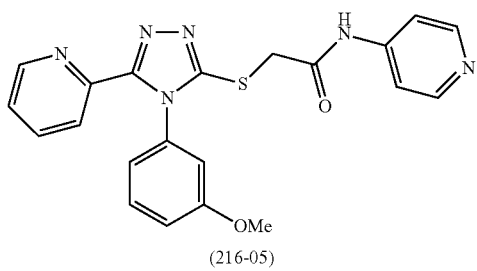
(216-05)
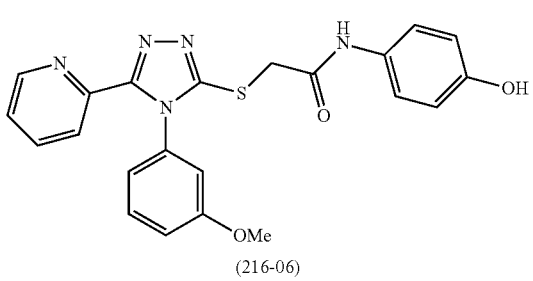
(216-06)
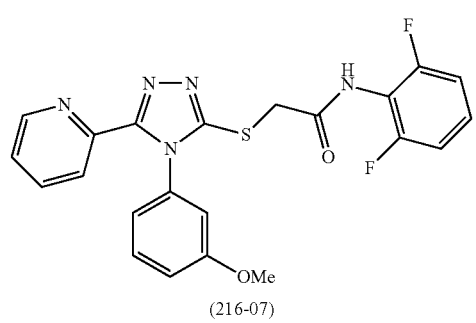
(216-07)
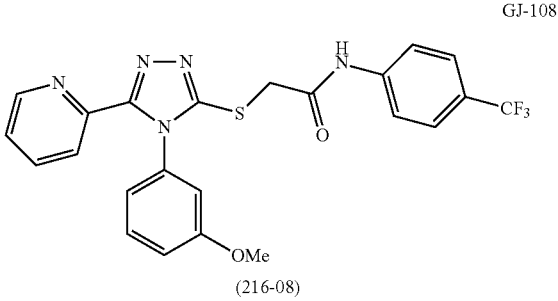
(216-08)
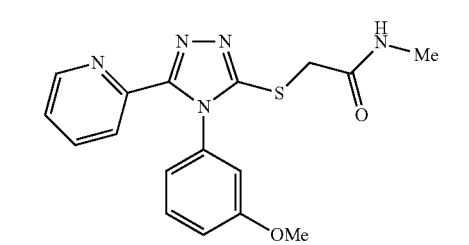
GJ-105
GJ-106
GJ-107
GJ-108
GJ-109

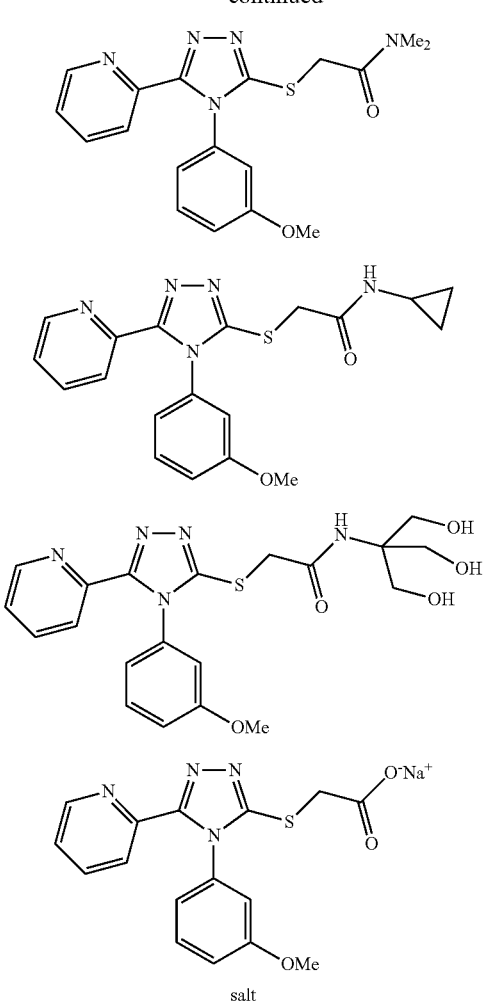

In some or any embodiments and aspects, the compound of formula Ia is that where $X^1$ is S.

In some or any embodiments and aspects, the compound of formula Ia is that where $Y^1$ is O.

In some or any embodiments and aspects, the compound of formula Ia is that where $R^{2a}$ is —$(CH_2)_m$— and m is 1.

In some or any embodiments and aspects, the compound of formula Ia is that where $R^{1a}$ is 3-hydroxylphenyl or 3-alkoxyphenyl. In some or any embodiments and aspects, the compound of formula Ia is that where $R^{1a}$ is 3-methoxyphenyl.

In some or any embodiments and aspects, the compound of formula Ia is that where $R^{3a}$ is hydroxy.

In some or any embodiments and aspects, the compound of formula Ia is that where $R^{3a}$ is —$NR^7R^{7a}$. In some or any embodiments and aspects, the compound of formula Ia is that where $R^{3a}$ is —$NR^7R^{7a}$ and $R^7$ is hydrogen.

In some or any embodiments and aspects, the compound of formula Ia is that where $R^{3a}$ is —$NR^7R^{7a}$ and $R^7$ is hydrogen and $R^{7a}$ is a 6-membered heteroaryl optionally substituted with 1, 2, or 3 $R^9$ groups. In some or any embodiments and aspects, the compound of formula Ia is that where $R^{3a}$ is —$NR^7R^{7a}$ and $R^7$ is hydrogen and $R^{7a}$ is pyridinyl optionally substituted with 1, 2, or 3 $R^9$ groups. In some or any embodiments and aspects, the compound of formula Ia is that where $R^{3a}$ is —$NR^7R^{7a}$ and $R^7$ is hydrogen and $R^{7a}$ is unsubstituted pyridinyl.

In some or any embodiments and aspects, the compound of formula Ia is that where $R^{3a}$ is —$NR^7R^{7a}$ and $R^7$ is hydrogen and $R^{7a}$ is $C_{1-3}$-alkyl. In some or any embodiments and aspects, the compound of formula Ia is that where $R^{3a}$ is —$NR^7R^{7a}$ and $R^7$ is hydrogen and $R^{7a}$ is methyl. In some or any embodiments and aspects, the compound of formula Ia is that where $R^{3a}$ is —$NR^7R^{7a}$ and $R^7$ and $R^{7a}$ are alkyl.

In some or any embodiments and aspects, the compound of formula Ia is that where $R^{3a}$ is —$NR^7R^{7a}$ and $R^7$ is hydrogen and $R^{7a}$ is cycloalkyl. In some or any embodiments and aspects, the compound of formula Ia is that where $R^{3a}$ is —$NR^7R^{7a}$ and $R^7$ is hydrogen and $R^{7a}$ is cyclopropyl, cyclobutyl, or cyclopentyl. In some or any embodiments and aspects, the compound of formula Ia is that where $R^{3a}$ is —$NR^7R^{7a}$ and $R^7$ is hydrogen and $R^{7a}$ is cyclopropyl.

In some or any embodiments and aspects, the compound of formula Ia is that where $R^{3a}$ is —$NR^7R^{7a}$ and $R^7$ is hydrogen and $R^{7a}$ is hydroxyalkyl. In some or any embodiments and aspects, the compound of formula Ia is that where $R^{3a}$ is —$NR^7R^{7a}$ and $R^7$ is hydrogen and $R^{7a}$ is 1,3-(dihydroxy)-2-(hydroxymethyl)prop-2-yl.

In some or any embodiments and aspects, the compound of formula Ia is that where $R^{3a}$ is —$NR^7R^{7a}$ and $R^7$ is hydrogen and $R^{7a}$ is phenyl substituted with two independently selected halo. In some or any embodiments and aspects, the compound of formula Ia is that where $R^{3a}$ is —$NR^7R^{7a}$ and $R^7$ is hydrogen and $R^{7a}$ is phenyl substituted with two fluoro.

In some or any embodiments and aspects, the compound of formula Ia is that where $R^{3a}$ is —$NR^7R^{7a}$ and $R^7$ is hydrogen and $R^{7a}$ is phenyl substituted with 1, 2, or 3 $R^8$ groups. In some or any embodiments and aspects, the compound of formula Ia is that where $R^{3a}$ is —$NR^7R^{7a}$ and $R^7$ is hydrogen and $R^{7a}$ is phenyl substituted with 1 or 2 $R^8$ groups. In some or any embodiments and aspects, the compound of formula Ia is that where $R^{3a}$ is —$NR^7R^{7a}$ and $R^7$ is hydrogen and $R^{7a}$ is phenyl substituted with 1 $R^8$ group which is hydroxy and optionally substituted with a second $R^8$. In some or any embodiments and aspects, the compound of formula Ia is that where $R^{3a}$ is —$NR^7R^{7a}$ and $R^7$ is hydrogen and $R^{7a}$ is phenyl substituted with 1 $R^8$ which is haloalkyl and optionally substituted with a second $R^8$. In some or any embodiments and aspects, the compound of formula Ia is that where $R^{3a}$ is —$NR^7R^{7a}$ and $R^7$ is hydrogen and $R^{7a}$ is phenyl substituted with 1 $R^8$ which is trifluoromethyl and optionally substituted with a second $R^8$.

In some or any embodiments and aspects, the compound of formula Ib is that where $X^2$ is S.

In some or any embodiments and aspects, the compound of formula Ib is that where $Y^2$ is O.

In some or any embodiments and aspects, the compound of formula Ib is that where $R^{2b}$ is —$(CH_2)_p$— and p is 1.

In some or any embodiments and aspects, the compound of formula Ib is that where $R^{1b}$ is heterocycloalkylalkyl. In some or any embodiments and aspects, the compound of formula Ib is that where $R^{1b}$ is tetrahydrofuranylalkyl. In some or any embodiments and aspects, the compound of formula Ib is that where $R^{1b}$ is tetrahydrofuranylmethyl.

In some or any embodiments and aspects, the compound of formula Ib is that where $R^{1b}$ is aryl optionally substituted with 1, 2, or 3 $R^{10}$ groups. In some or any embodiments and aspects, the compound of formula Ib is that where $R^{1b}$ is phenyl optionally substituted with 1, 2, or 3 $R^{10}$ groups. In some or any embodiments and aspects, the compound of formula Ib is that where $R^{1b}$ is phenyl optionally substituted with 1 or 2 $R^{10}$ groups. In some or any embodiments and aspects, the compound of formula Ib is that where $R^{1b}$ is phenyl substituted with 1 or 2 $R^{10}$ groups. In some or any embodiments and aspects, the compound of formula Ib is that where $R^{1b}$ is phenyl substituted with one alkoxy. In some or any embodiments and aspects, the compound of formula Ib is that where $R^{1b}$ is 3-alkoxyphenyl. In some or any embodiments and aspects, the compound of formula Ib is that where $R^{1b}$ is 3-methoxy-phenyl.

In some or any embodiments and aspects, the compound of formula Ib is that where $R^{1b}$ is alkyl. In some or any embodiments and aspects, the compound of formula Ib is that where $R^{1b}$ is methyl, ethyl, or propyl.

In some or any embodiments and aspects, the compound of formula Ib is that where $R^{1b}$ is alkoxyalkyl. In some or any embodiments and aspects, the compound of formula Ib is that where $R^{1b}$ is methoxyalkyl. In some or any embodiments and aspects, the compound of formula Ib is that where $R^{1b}$ is 3-methoxy-propyl.

In some or any embodiments and aspects, the compound of formula Ib is that where $R^{1b}$ is heteroarylalkyl. In some or any embodiments and aspects, the compound of formula Ib is that where $R^{1b}$ is furanylmethyl.

In some or any embodiments and aspects, the compound of formula Ib is that where $R^{1b}$ is arylalkyl. In some or any embodiments and aspects, the compound of formula Ib is that where $R^{1b}$ is phenylalkyl. In some or any embodiments and aspects, the compound of formula Ib is that where $R^{1b}$ is benzyl.

In some or any embodiments and aspects, the compound of formula Ib is that where $R^{3b}$ is carboxy.

In some or any embodiments and aspects, the compound of formula Ib is that where $R^{3b}$ is —$NR^{11}R^{11a}$ In some or any embodiments and aspects, the compound of formula Ib is that where $R^{3b}$ is —$NR^{11}R^{11a}$ and $R^{11}$ is hydrogen.

In some or any embodiments and aspects, the compound of formula Ib is that where $R^{3b}$ is —$NR^{11}R^{11a}$ and $R^{11}$ is hydrogen and $R^{11a}$ is aryl optionally substituted with 1, 2, or 3 $R^{13}$ groups. In some or any embodiments and aspects, the compound of formula Ib is that where $R^{3b}$ is —$NR^{11}R^{11a}$ and $R^{11}$ is hydrogen and $R^{11a}$ is phenyl optionally substituted with 1, 2, or 3 $R^{13}$ groups. In some or any embodiments and aspects, the compound of formula Ib is that where $R^{3b}$ is —$NR^{11}R^{11a}$ and $R^{11}$ is hydrogen and $R^{11a}$ is phenyl optionally substituted with 1 or 2 $R^{13}$ groups. In some or any embodiments and aspects, the compound of formula Ib is that where $R^{3b}$ is —$NR^{11}R^{11a}$ and $R^{11}$ is hydrogen and $R^{11a}$ is phenyl substituted with 1 or 2 $R^{13}$ groups. In some or any embodiments and aspects, the compound of formula Ib is that where $R^{3b}$ is —$NR^{11}R^{11a}$ and $R^{11}$ is hydrogen and $R^{11a}$ is phenyl substituted with 1 $R^{13}$ group which is halo, hydroxy, alkyl, haloalkyl, alkoxy, or alkoxycarbonyl and optionally substituted with a second $R^{13}$.

In some or any embodiments and aspects, the compound of formula Ib is that where $R^{4b}$ is heteroaryl. In some or any embodiments and aspects, the compound of formula Ib is that where $R^{4b}$ is pyridinyl. In some or any embodiments and aspects, the compound of formula Ib is that where $R^{4b}$ is pyridin-2-yl or pyridiny-4-yl. In some or any embodiments and aspects, the compound of formula Ib is that where $R^{4b}$ is pyridin-2-yl. In some or any embodiments and aspects, the compound of formula Ib is that where $R^{4b}$ is thienyl. In some or any embodiments and aspects, the compound of formula Ib is that where $R^{4b}$ is thien-2-yl.

In some or any embodiments and aspects, the compound of formula Ib is that where $R^{4b}$ is alkyl. In some or any embodiments and aspects, the compound of formula Ib is that where $R^{4b}$ is methyl, ethyl, or propyl. In some or any embodiments and aspects, the compound of formula Ib is that where $R^{4b}$ is propyl.

In some or any embodiments and aspects, the compound of formula Ib is that where $R^{4b}$ is aryl optionally substituted with 1, 2, or 3 $R^{12}$ groups. In some or any embodiments and aspects, the compound of formula Ib is that where $R^{4b}$ is phenyl optionally substituted with 1, 2, or 3 $R^{12}$ groups. In some or any embodiments and aspects, the compound of formula Ib is that where $R^{4b}$ is phenyl substituted with for 2 $R^{12}$ groups. In some or any embodiments and aspects, the compound of formula Ib is that where $R^{4b}$ is phenyl substituted with 1$R^{12}$ which is amino and optionally substituted with a second $R^{12}$.

In some or any embodiments and aspects, the compound is according to formula 2.

In some or any embodiments and aspects, the compound according to formula 2 is that where Z is S.

In some or any embodiments and aspects, the compound according to formula 2 is that where $R^5$ is —$NR^{5a}R^{5b}$. In some or any embodiments and aspects, the compound according to formula 2 is that where $R^5$ is —$NR^{5a}R^{5b}$ and $R^{5a}$ is hydrogen.

In some or any embodiments and aspects, the compound according to formula 2 is that where $R^5$ is —$NR^{5a}R^{5b}$ and $R^{5a}$ is hydrogen and $R^{5b}$ is aryl. In some or any embodiments and aspects, the compound according to formula 2 is that where $R^5$ is —$NR^{5a}R^{5b}$ and $R^{5a}$ is hydrogen and $R^{5b}$ is phenyl.

In some or any embodiments and aspects, the compound according to formula 2 is that where $R^5$ is —$NR^{5a}R^{5b}$ and $R^{5a}$ is hydrogen and $R^{5b}$ is alkyl. In some or any embodiments and aspects, the compound according to formula 2 is that where $R^5$ is —$NR^{5a}R^{5b}$ and $R^{5a}$ is hydrogen and $R^{5b}$ is methyl, ethyl, or propyl.

In some or any embodiments and aspects, the compound according to formula 2 is that where $R^5$ is —$NR^{5a}R^{5b}$ and $R^{5a}$ is hydrogen and $R^{5b}$ is alkenyl. In some or any embodiments and aspects, the compound according to formula 2 is that where $R^5$ is —$NR^{5a}R^{5b}$ and $R^{5a}$ is hydrogen and $R^{5b}$ is allyl.

In some or any embodiments and aspects, the compound according to formula 2 is that where $R^5$ is —$NR^{5a}R^{5b}$ and $R^{5a}$ is hydrogen and $R^{5b}$ is arylalkyl. In some or any embodiments and aspects, the compound according to formula 2 is that where $R^5$ is —$NR^{5a}R^{5b}$ and $R^{5a}$ is hydrogen and $R^{5b}$ is phenylalkyl. In some or any embodiments and aspects, the compound according to formula 2 is that where $R^5$ is —$NR^{5a}R^{5b}$ and $R^{5a}$ is hydrogen and $R^{5b}$ is benzyl.

In some or any embodiments and aspects, the compound according to formula 2 is that where $R^5$ is —$NR^{5a}R^{5b}$ and $R^{5a}$ is hydrogen and $R^{5b}$ is alkoxyalkyl. In some or any embodiments and aspects, the compound according to formula 2 is that where $R^5$ is —$NR^{5a}R^{5b}$ and $R^{5a}$ is hydrogen and $R^{5b}$ is methoxyalkyl. In some or any embodiments and aspects, the compound according to formula 2 is that where $R^5$ is —$NR^{5a}R^{5b}$ and $R^{5a}$ is hydrogen and $R^{5b}$ is 3-methoxy-propyl.

In another aspect, it is provided a composition, which composition comprising at least one compound or a pharmaceutically acceptable salt or prodrug thereof, in an amount effective for treating or ameliorating a medical condition associated with PTCs in RNA, wherein the compound is according to any of the various embodiments described above or below.

In some or any embodiments of the composition, optionally in combination with any or all of the above various embodiments, the composition further comprises a pharmaceutically acceptable carrier or pharmaceutically acceptable excipient.

In some or any embodiments of the composition, optionally in combination with any or all of the above various embodiments, the composition is in a formulation for local or systemic delivery.

In some or any embodiments of the composition, optionally in combination with any or all of the above various embodiments, the composition is in a formulation for oral administration, injection, topical administration, pulmonary administration, or implant.

In some or any embodiments of the composition, optionally in combination with any or all of the above various embodiments, the medical condition is selected from the group consisting of central nervous system diseases, such as ataxia-telangiectasia, muscular dystrophy, Duchenne muscular dystrophy, Dravet syndrome, myotonic dystrophy, multiple sclerosis, infantile neuronal ceroid lipofuscinosis, Alzheimer's disease, Tay-Sachs disease, neural tissue degeneration, and Parkinson's disease; autoimmune diseases such as chronic rheumatoid arthritis, lupus erythematosus, and graft-versus-host disease; primary immunodeficiencies such as severe combined immunodeficiency and DNA Ligase IV deficiency; DNA repair disorders such as Nijmegen breakage disorders and xeroderma pigmentosum (XP); inflammatory diseases such as rheumatoid arthritis; blood diseases such as hemophilia, von Willebrand disease, thalassemia, familial erythrocytosis, and nephrolithiasis; collagen diseases such as osteogenesis imperfecta and cirrhosis; neurofibroma; bullous disease; lysosomal storage disease; Hurler's disease; familial cholesteremia; cerebellar ataxia; tuberous sclerosis; immune deficiency; kidney disease; lung disease; cystic fibrosis; familial hypercholesterolemia; pigmentary retinopathy; amyloidosis; atherosclerosis; gigantism; dwarfism; hypothyroidism; hyperthyroidism; aging; obesity; diabetes mellitus; Niemann-Pick disease; Marfan syndrome; neuromuscular diseases; Becker muscular dystrophy (BMD); spinal muscular atrophy; cancer; and any genetic disorder caused by nonsense mutation(s).

In another aspect, it is provided a method of treating or ameliorating a medical condition associated with PTCs in RNA, comprising administering to a subject in need thereof a compound according to any of the various embodiments described above or below or a composition according to any of the various embodiments described above or below.

In some embodiments of the method, optionally in combination with any or all of the above various embodiments, the medical condition is selected from the group consisting of central nervous system diseases, such as ataxia-telangiectasia, muscular dystrophy, Duchenne muscular dystrophy, Dravet syndrome, myotonic dystrophy, multiple sclerosis, infantile neuronal ceroid lipofuscinosis, Alzheimer's disease, Tay-Sachs disease, neural tissue degeneration, and Parkinson's disease; autoimmune diseases such as chronic rheumatoid arthritis, lupus erythematosus, and graft-versus-host disease; primary immunodeficiencies such as severe combined immunodeficiency and DNA Ligase IV deficiency; DNA repair disorders such as Nijmegen breakage disorders and xeroderma pigmentosum (XP); inflammatory diseases such as rheumatoid arthritis; blood diseases such as hemophilia, von Willebrand disease, thalassemia, familial erythrocytosis, and nephrolithiasis; collagen diseases such as osteogenesis imperfecta and cirrhosis; neurofibroma; bullous disease; lysosomal storage disease; Hurler's disease; familial cholesteremia; cerebellar ataxia; tuberous sclerosis; immune deficiency; kidney disease; lung disease; cystic fibrosis; familial hypercholesterolemia; pigmentary retinopathy; amyloidosis; atherosclerosis; gigantism; dwarfism; hypothyroidism; hyperthyroidism; aging; obesity; diabetes mellitus; Niemann-Pick disease; Marfan syndrome; neuromuscular diseases; Becker muscular dystrophy (BMD); spinal muscular atrophy; cancer; and any genetic disorder caused by nonsense mutation(s).

In a further aspect, it is provided a method of making a compound, comprising synthesizing a compound as any of the various embodiments described above or below. Examples of the method are further described in the Examples.

In a further aspect, it is provided a method of forming a composition, comprising providing a compound and forming the composition. In some embodiments, the composition further comprises a pharmaceutically acceptable carrier. In some embodiments of the composition, optionally in combination with any or all of the above various embodiments, the composition is formulated in a formulation for local or systemic delivery. Examples of such formulations are formulations for oral administration, injection, topical administration, pulmonary administration, or implant.

Methods of Use

As described herein, the RTCs disclosed are able to induce readthrough of ATM nonsense mutations and restore its kinase activity. In the ATM mutation spectrum identified from A-T patients, primary nonsense mutations account for ~15% of the unique mutations. Considering the most patients are compounds heterozygotes, this RTC treatment approach could apply to more than 30% of total patients.

The compounds described here could be used as oral formulation to treat e.g. A-T, DMD, cystic fibrosis or other genetic diseases. If proven safe for long-term administration, they may be useful prophylactically in carriers of highly penetrant cancer genes, such as BRAC1/2, for preventing cancer.

In a further aspect, it is provided a method of using the RTCs disclosed herein. The method comprises applying the RTC to a subject to treat, prevent, or ameliorate a medical condition. The medical condition can be any disease or disorder caused by or otherwise associated with PTC.

In some embodiments, the method can be conducted in living bodies of mammals. In such a case, the compounds may be administered to the mammals. In one embodiment, the mammals may be patients with genetic diseases caused by nonsense mutation, and the method may be conducted as a treatment method of genetic diseases caused by nonsense mutation.

As used herein, the term disorder and medical condition can be used interchangeably and generally refer to a disease attributable to an internal termination codon in a gene (a premature termination codon) generated by such as a point mutation, deletion, and insertion in the gene which leads to inhibition of expression of protein having a normal function, or attributable to degradation of mRNA that contains the premature termination codon which leads to inhibition of protein expression. The genetic disease caused by nonsense mutation is not specifically limited, but is exemplified by the following: central nervous system diseases such as ataxia-telangiectasia, muscular dystrophy, Duchenne muscular dystrophy, Dravet syndrome, myotonic dystrophy, multiple sclerosis, infantile neuronal ceroid lipofuscinosis, Alzheimer's disease, Tay-Sachs disease, neural tissue degeneration, and Parkinson's disease; autoimmune diseases such as chronic rheumatoid arthritis, lupus erythematosus, and graft-versus-host disease; primary immunodeficiencies such as severe combined immunodeficiency and DNA Ligase IV deficiency; DNA repair disorders such as Nijmegen breakage disorders and xeroderma pigmentosum (XP); inflammatory diseases such as rheumatoid arthritis; blood diseases such as hemophilia, von Willebrand disease, thalassemia, familial erythrocytosis, and nephrolithiasis; collagen diseases such as osteogenesis imperfecta and cirrhosis; neurofibroma; bullous disease; lysosomal storage disease; Hurler's disease; familial cholesterolemia; cerebellar ataxia; tuberous sclerosis; immune deficiency; kidney disease; lung disease; cystic fibrosis; familial hypercholesterolemia; pigmentary retinopathy; amyloidosis; atherosclerosis; gigantism; dwarfism; hypothyroidism; hyperthyroidism; aging; obesity; diabetes mellitus; Niemann-Pick disease; Marfan syndrome; neuromuscular diseases; Becker muscular dystrophy (BMD); spinal muscular atrophy; cancer; and any genetic disorder caused by nonsense mutation(s). The term "cancer", such as cancer associated with a nonsense mutation of a suppressor gene such as p53 gene, includes all types of cancer, which is exemplified by lung cancer, colon and rectal cancer, stomach cancer, esophageal cancer, kidney cancer, pancreatic cancer, prostate cancer, breast cancer, uterine cancer, ovarian cancer, skin cancer, sarcoid, leukemia, lymphoma, and brain tumor.

In another aspect is a method for enhancing production in a subject of a functional protein from a gene disrupted by the presence of a premature stop codon in the coding region of the gene, comprising administering to the subject a compound of formula 1, 2, 3, Ia, or Ib according to some or any embodiments in an amount effective to suppress the premature stop codon and increase transcription of the gene. In some or any embodiments the compound further comprises a pharmaceutical composition. In some or any embodiments, the pharmaceutical composition comprises the compound of formula XXX and a pharmaceutically acceptable carrier or a pharmaceutically acceptable excipient. In some or any embodiments, the gene is ATM.

A method for enhancing production in a subject of a functional protein, where production of the protein is disrupted by a genetic mutation, comprising administering to the subject a compound of formula 1, 2, 3, Ia, or Ib according to some or any embodiments in an amount effective to suppress the genetic mutation and/or correct a defect caused by the mutation and to increase transcription of the gene. In some or any embodiments the compound further comprises a pharmaceutical composition. In some or any embodiments, the pharmaceutical composition comprises the compound of formula XXX and a pharmaceutically acceptable carrier or a pharmaceutically acceptable excipient. In some or any embodiments, the gene is ATM.

Pharmaceutical Compositions

In another aspect, a pharmaceutical composition for use in treatment or prevention of the genetic diseases caused by nonsense mutation is provided, wherein the pharmaceutical composition comprises as an effective ingredient a compound expressed by any one of the aforementioned formulae a pharmacologically acceptable salt or prodrug thereof.

The pharmaceutical composition preferably comprises a compound described above or a pharmacologically acceptable salt or prodrug thereof.

The pharmaceutical composition more preferably comprises a compound shown in the aforementioned table.

In the aforementioned aspect, the pharmaceutical composition may contain a pharmacologically acceptable carrier or excipients. An amount of the compound used in the pharmaceutical composition is not limited as far as it is an effective amount for treatment. The genetic disease caused by nonsense mutation is not specifically limited, but is exemplified by the following: central nervous system diseases, such as ataxia-telangiectasia, muscular dystrophy, Duchenne muscular dystrophy, Dravet syndrome, myotonic dystrophy, multiple sclerosis, infantile neuronal ceroid lipofuscinosis, Alzheimer's disease, Tay-Sachs disease, neural tissue degeneration, and Parkinson's disease; autoimmune diseases such as chronic rheumatoid arthritis, lupus erythematosus, and graft-versus-host disease; primary immunodeficiencies such as severe combined immunodeficiency and DNA Ligase IV deficiency; DNA repair disorders such as Nijmegen breakage disorders and xeroderma pigmentosum (XP); inflammatory diseases such as rheumatoid arthritis; blood diseases such as hemophilia, von Willebrand disease, thalassemia, familial erythrocytosis, and nephrolithiasis; collagen diseases such as osteogenesis imperfecta and cirrhosis; neurofibroma; bullous disease; lysosomal storage disease; Hurler's disease; familial cholesterolemia; cerebellar ataxia; tuberous sclerosis; immune deficiency; kidney disease; lung disease; cystic fibrosis; familial hypercholesterolemia; pigmentary retinopathy; amyloidosis; atherosclerosis; gigantism; dwarfism; hypothyroidism; hyperthyroidism; aging; obesity; diabetes mellitus; Niemann-Pick disease; Marfan syndrome; neuromuscular diseases; Becker muscular dystrophy (BMD); spinal muscular atrophy; cancer; and any genetic disorder caused by nonsense mutation(s). The term "cancer", such as cancer associated with a nonsense mutation of a suppressor gene such as p53 gene, includes all types of cancer, which is exemplified by lung cancer, colon and rectal cancer, stomach cancer, esophageal cancer, kidney cancer, pancreatic cancer, prostate cancer, breast cancer, uterine cancer, ovarian cancer, skin cancer, sarcoid, leukemia, lymphoma, and brain tumor.

The pharmaceutical composition may contain, as active ingredients, the aforementioned compound and other compounds, or may contain a mixture of two or more aforementioned compounds.

The pharmacologically acceptable salt s not specifically limited as far as it can be used in medicaments. Examples of a salt that the compound of the present invention forms with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

Further, the compounds include hydrates thereof, various pharmaceutically acceptable solvates thereof, and polymorphic crystals thereof.

The pharmaceutical compositions can be formulated in various dosage forms, which are exemplified by the following: oral administration forms such as tablets, capsules, powders, granules, pills, liquids, emulsions, suspensions, solutions, spirits, syrups, extracts, and elixirs; parenteral administration forms such as injections, for example, subcutaneous injections, intravenous injections, intramuscular injections, and intraperitoneal injections; transdermal administration forms, plasters and pressure sensitive adhesives, ointments or lotions; intramouth administration forms such as sublingual forms and oral patch preparations; and nasal administration forms such as aerosols, but are not limited thereto. These preparations can be manufactured by using a known method generally used in a drug manufacturing process. In one embodiment, the pharmaceutical composition may be administered for treating muscular disease as an injection such as an intramuscular injection for administering directly into muscle.

The pharmaceutical compositions may contain various kind of ingredients generally used, for example, one or more pharmaceutically acceptable fillers, disintegrators, diluents, lubricants, flavoring agents, colorants, sweetening agents, corrigents, suspending agents, humectants, emulsifying agents, dispersing agents, auxiliary agents, preservatives, buffers, binders, stabilizers, and coating agents. In addition, the pharmaceutical composition of the present invention may be sustained-release dosage forms or extended-release dosage forms.

Dosage ranges of the pharmaceutical compositions are not particularly limited, and can be determined in accordance with the following: effectiveness of the ingredients contained therein; the administration form; the route of administration; the type of disease; the characteristics of the subject (e.g., body weight, age, symptomatic conditions, and whether a subject is taking other pharmaceutical agents); and the judgment of a physician in charge. In general, a suitable dosage may fall, for example, within a range of about 0.01 μg to 100 mg, per 1 kg of the body weight of the subject, and preferably within a range of about 0.1 μg to 1 mg, per 1 kg of body weight. However, the dosage may be altered using conventional experiments for optimization of a dosage that are well known in the art. The aforementioned dosage can be divided for administration once to several times a day. Alternatively, periodic administration once every few days or few weeks can be employed.

The pharmaceutical compositions may be administered to a patient whose biological sample obtained in advance is subjected to a study for presence or absence of premature termination codons in genes contained therein and is found to have a detected premature termination codon. A biological sample may be any ones insofar as it contains nucleic acids, and is exemplified by cells, bloods, cerebrospinal fluids, bronchoalveolar lavage fluids, expectorations, or other body fluids as well as biopsy tissues. Nucleic acid samples can be prepared from the biological samples for use. The nucleic acid samples can be prepared by well known nucleic acid preparation methods. The nucleic acid samples may be DNA or RNA. The nucleic acid samples prepared may be used directly for detection, or may be subjected to enzymatic amplification of predetermined region thereof by PCR or other amplification methods in advance for analysis. Detection of a termination codon can be carried out by using well known methods for detecting genetic mutations such as DNA sequencing, Southern blot, polymerase chain reaction (PCR), short tandem repeat (STR), or restricted fragment length polymorphism. The detection method is not limited to the exemplified methods, and any method can be used insofar as it can detect a premature termination codon. Alternatively, the presence of a premature termination codon can be detected by measuring an amount of mRNA derived from the predetermined gene in the biological sample and detecting reduction of the amount of the mRNA compared to an amount of mRNA derived from the gene in a biological sample obtained from healthy subject. mRNA can be measures by using known analysis methods such as northern blotting.

In terms of a route of administration of the pharmaceutical composition, it may be either systemic administration or local administration. The route of administration that is appropriate for a particular disease, symptomatic condition, or other factors, should be selected. For example, parenteral administration including normal intravenous injection, intraarterial administration, subcutaneous administration, intracutaneous administration, and intramuscular administration can be employed. Oral administration can be also employed. Further, transmucosal administration or transdermal administration can be employed.

The term "read-through" herein means to skip over a premature termination codon in ribosomal translation, or to substitute an amino acid, or to suppress degradation of mRNA that comprises a premature termination codon.

In the aforementioned aspect, a sequence that comprises a premature termination codon derive from responsible genes for diseases caused by nonsense mutation is not specifically limited insofar as it is a sequence comprising a termination codon such as TAA, TAG, or TGA, in a reading frame. The sequence is preferably around 20 to 150 by long. In one embodiment, the sequence may be a sequence containing a sequence that comprises a premature termination codon of humans or animals having genetic disease caused by nonsense mutation including animal models for the diseases. For example, such a gene can contain a premature termination codon in the dystrophin gene of mdx mice.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However, the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch, or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds described herein. Agents which can advantageously be combined with compounds described herein in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds described herein in single formulations are in accord with the doses used in standard clinical practice. Established safe and effective dose ranges for certain representative compounds are set forth above.

The following are illustrative examples of how the compounds can be prepared and tested. Although the examples can represent only some embodiments, it should be understood that the following examples are illustrative and not limiting.

SYNTHETIC EXAMPLES

Compounds disclosed herein are commercially available or can be readily prepared from commercially available starting materials according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Synthesis of some of the compounds are exemplified in detail below.

Materials were obtained from commercial suppliers and were used without further purification. Air or moisture sensitive reactions were conducted under argon atmosphere using oven-dried glassware and standard syringe/septa techniques. The reactions were monitored with a silica gel TLC plate under UV light (254 nm) followed by visualization with a p-anisaldehyde or ninhydrin staining solution. Column chromatography was performed on silica gel 60. $^1$H NMR spectra were measured at 400 MHz in CDCl$_3$ unless stated otherwise and data were reported as follows in ppm (δ) from the internal standard (TMS, 0.0 ppm: chemical shift (multiplicity, integration, coupling constant in Hz.).

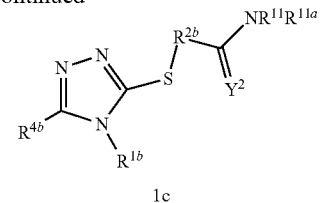

1c

Compounds of formula 1 (where X is S, Y is O, $R^3$ is OH, alkoxy, or $NR^6R^{6a}$ and all other groups are as defined in the Summary of the Invention) or of formula Ib (where $X^2$ is S, $Y^2$ is P, $R^{3b}$ is OH, alkoxy, or $NR^{11}R^{11a}$ and all other groups are as defined in the Summary of the Invention) can be prepared by the condensation of an acyl hydrazide of formula 3a with a substituted isothiocyanate of formula $R^1NCS$ followed by treatment with base such as NaOH to give an intermediate of formula 5a. Alkylation of 5a in base, e.g. KOH, with an intermediate of formula $XCH_2C(O)OR$ (where X is halo and R is hydrogen or alkyl), afforded the intermediate of formula 6a. Condensation of 6a with mono- and di-substituted amines of formula $NHR^6R^{6a}$ in the presence of a coupling reagent such as HBTU and a base such as triethylamine (or using other amide formation procedures known to one of ordinary skill in the art) afforded compounds of 1c.

General Scheme 1a

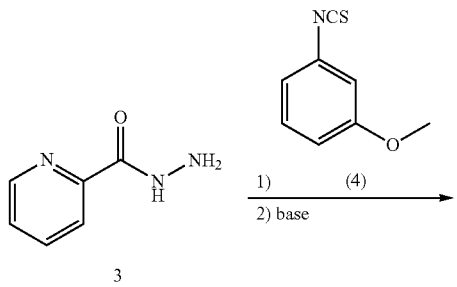

General Scheme 1

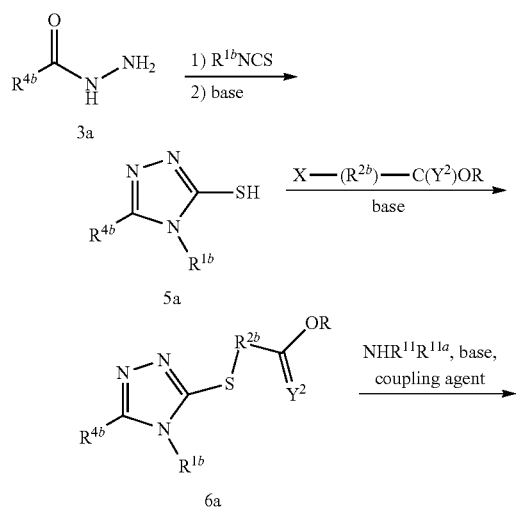

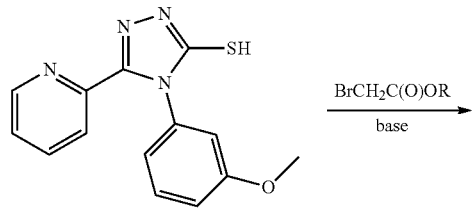

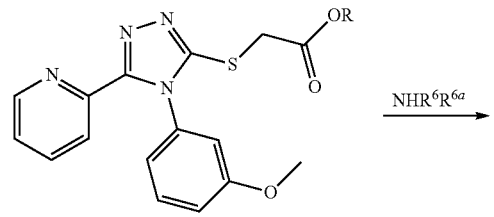

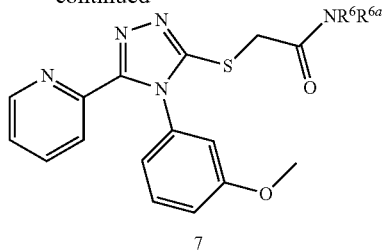

7

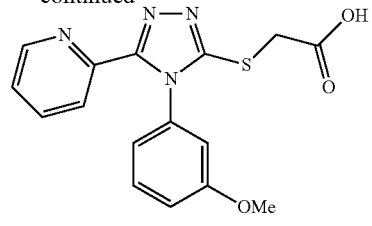

1a

More particularly, the 1,2,4-triazole-3-thiones were prepared by the condensation of an acyl hydrazide, e.g., the 2-pyridyl compound 3, with a substituted isothiocyanate, e.g., the 3-methoxyphenyl compound 4, to give, after treatment of the intermediate with base such as NaOH, the triazolethione 5. Alkylation of this thione 5 in base, e.g. KOH, with chloroacetic acid or an alkyl bromoacetate, afforded the 3-[(carboxymethyl)thio]triazole or the 3-[(carboalkoxymethyl)thio]triazole 6. Condensation of the acid or esters with mono- and di-substituted amines of formula NHR$^6$R$^{6a}$ afforded the amides 7.

Using the procedures described in Scheme 1 and 1a, the following compounds were made, namely the acid 1a and its sodium salt 1k, and the series of amides, 1b-1j.

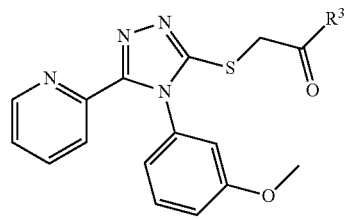

1a R$^3$=OH
1b R$^3$=NH(phenyl)
1c R$^3$=NH(pyridin-4-yl)
1d R$^3$=NH(4-hydroxyphenyl)
1e R$^3$=NH(4-fluorophenyl)
1f R$^3$=NH(2,6-difluorophenyl)
1g R$^3$=NH(4-trifluoromethylphenyl)
1h R$^3$=NHCH$_3$
1i R$^3$=N(CH$_3$)$_2$
1j R$^3$=NH(cyclopropyl)
1k R$^3$=O$^-$Na$^+$ Synthetic Examples 1a-1k

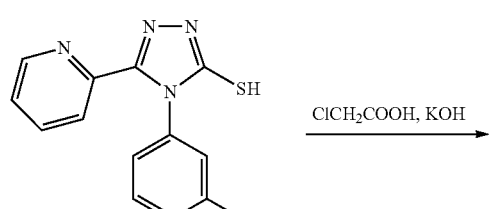

5

Preparation of 2-(4-(3-methoxyphenyl)-5-(pyridin-2-yl)-4H-1,2,4-triazol-3-ylthio)acetic acid 1a A mixture of triazolethione 5 (1.75 g, 6.2 mmol), 2-chloroacetic acid (584 mg, 5.1 mmol) and aqueous potassium hydroxide solution (2 M) (170 mL, 5.1 mmol) was refluxed for 3 h. The hot reaction mixture was filtered and the filtrate acidified with 2 M hydrochloric acid. The compound was precipitated out, filtered, washed with water. Recrystallization from an ethyl acetate/hexanes mixture gave 1a in 83% yield (1.76 g, light yellow solid). $^1$H NMR (500 MHz, (CD$_3$)$_2$SO): 8.37 (d, J=4.0 Hz, 1H), 7.99-7.91 (m, 2H), 7.44-7.38 (m, 2H), 7.09 (d, J=6.5 Hz, 1H), 6.98 (s, 1H), 6.90 (d, J=7.5 Hz, 1H), 4.10 (s, 2H), 3.73 (s, 3H). $^{13}$C NMR (125 MHz, (CD$_3$)$_2$SO): δ 169.6, 159.9, 153.9, 152.7, 149.4, 146.5, 137.5, 135.7, 130.5, 124.7, 123.9, 119.6, 115.2, 113.5, 55.8, 34.5 ppm.

Salt 1k: To a solution of 1a (1.0 mmol) in THF, was added 1.0 M aqueous NaOH (1.3 mmol). The reaction mixture was stirred overnight at rt. The organic solvent was evaporated and the aqueous solution was stirred at 0° C. for 2 h. The precipitate formed was filtered off and the filtrate was concentrated. The yellow solid was washed with cold water and dried using a lyophilizer. The desired salt 1k was obtained as a yellow solid. $^1$H NMR (500 MHz, DMSO-d$_6$): 8.37 (d, J=4.0 Hz, 1H), 7.99-7.91 (m, 2H), 7.44-7.38 (m, 2H), 7.09 (d, J=6.5 Hz, 1H), 6.98 (s, 1H), 6.90 (d, J=7.5 Hz, 1H), 4.10 (s, 2H), 3.73 (s, 3H). $^{13}$C NMR (125 MHz, DMSO-d$_6$): δ 169.6, 159.9, 153.9, 152.7, 149.4, 146.5, 137.5, 135.7, 130.5 124.7, 123.9, 119.6, 115.2, 113.5, 55.8, 34.5 ppm.

General Procedure for the Synthesis of Compounds 1b-1j.

To a solution of triazole 1a (100 mg, 0.30 mmol) and the appropriate amine, NHR$^6$R$^{6a}$, e.g. aniline (34 mg, 0.36 mmol) in dichoromethane (2 mL), O-benzotriazole-N,N,N', N'-tetramethyl-uronium-hexafluoro-phosphate (HBTU) (120 mL, 0.36 mmol), and triethylamine (0.05 mL, 0.36 mmol) were added. The reaction mixture was stirred for 4 h. After removal of solvent under reduced pressure, the residue was dissolved in ethyl acetate, washed with water, aqueous NaHCO$_3$, and brine solution. The organic layers were combined, dried over anhydrous MgSO$_4$, and then concentrated in vacuo. The crude mixture was purified by column chromatography on silica gel (ethyl acetate:hexane, 1:1) yielding the desired product (1b to 1j) at 70-90% yield.

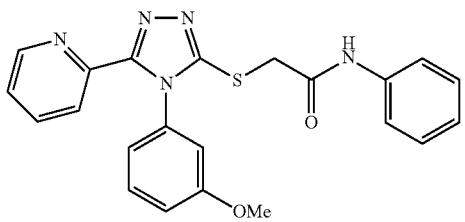 [SMILES: COc1cccc(-n2c(SCC(=O)Nc3ccccc3)nnc2-c2ccccn2)c1]

2-(4-(3-Methoxyphenyl)-5-(pyridin-2-yl)-4H-1,2,4-triazol-3-ylthio)-N-phenylacetamide (1b)

$^1$H NMR (300 MHz, CDCl$_3$): δ 10.40 (s, 1H), 8.00 (d, J=8.1 Hz, 1H), 7.74 (dt, J=7.8, 1.8 Hz, 1H), 7.63 (d, J=8.7 Hz, 1H), 7.38-7.21 (m, 4H), 7.09-6.99 (m, 2H), 6.83-6.79 (m, 2H), 4.01 (s, 2H), 3.85 (s, 3H); $^{13}$C NMR (75 MHz, CDCl$_3$): δ 166.7, 160.3, 154.9, 154.3, 149.3, 146.1, 138.4, 136.8, 135.2, 130.3, 128.9, 124.3, 124.1, 123.5, 119.8, 119.2, 115.7, 112.7 ppm

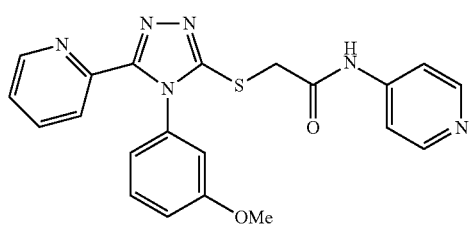 [SMILES: COc1cccc(-n2c(SCC(=O)Nc3ccncc3)nnc2-c2ccccn2)c1]

2-(4-(3-Methoxyphenyl)-5-(pyridin-2-yl)-4H-1,2,4-triazol-3-ylthio)-N-(pyridin-4-yl)acetam-ide (1c)

$^1$H NMR (500 MHz, CDCl$_3$): δ 10.97 (s, 1H), 8.45 (d, J=6.0 Hz, 1H), 8.36 (d, J=4.5 Hz, 1H), 7.97 (d, J=8.0 Hz, 1H), 7.76 (dt, J=1.5, 7.5 Hz, 1H), 7.56-7.54 (m, 2H), 7.35 (t, J=8.5 Hz, 1H), 7.25 (d, J=8.5 Hz, 1H), 7.02 (dd, J=2.0, 8.5 Hz, 1H), 6.82-6.79 (m, 2H), 3.98 (s, 2H), 3.80 (s, 3H); $^{13}$C NMR (75 MHz, CDCl$_3$): δ 167.4, 160.2, 154.7, 150.5, 149.2, 145.8, 145.1, 136.7, 134.9, 130.2, 124.3, 123.4, 118.9, 115.5, 113.7, 113.6, 112.6, 55.5, 36.2 ppm.

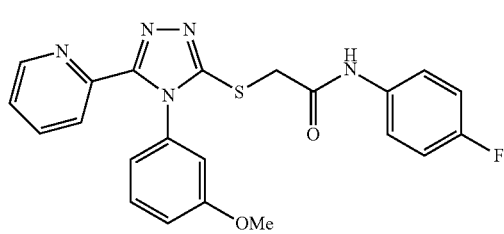 [SMILES: COc1cccc(-n2c(SCC(=O)Nc3ccc(F)cc3)nnc2-c2ccccn2)c1]

2-(4-(3-Methoxyphenyl)-5-(pyridin-2-yl)-4H-1,2,4-triazol-3-ylthio)-N-(4-fluorophenyl)acet-amide (1e)

$^1$H NMR (300 MHz, CDCl$_3$): δ 10.47 (s, 1H), 8.34 (bs, 1H), 8.05 (d, J=7.5 Hz, 1H), 7.74 (t, J=7.5 Hz, 1H), 7.35 (t, J=7.5 Hz, 1H), 7.26-7.13 (m, 2H), 7.02 (dd, J=8.0, 0.5 Hz, 1H), 6.91 (t, J=8.0 Hz, 2H), 6.84-6.81 (m, 2H), 4.08 (s, 2H), 3.79 (s, 3H). $^{19}$F NMR (400 MHz, CDCl$_3$): δ−118.9 ppm.

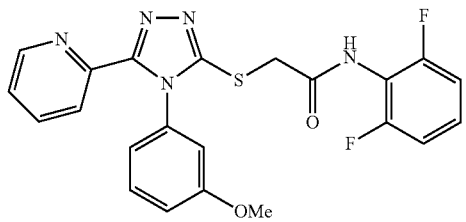 [SMILES: COc1cccc(-n2c(SCC(=O)Nc3c(F)cccc3F)nnc2-c2ccccn2)c1]

2-(4-(3-Methoxyphenyl)-5-(pyridin-2-yl)-4H-1,2,4-triazol-3-ylthio)-N-(2,6-difluorophenyl)-acetamide (1f)

$^1$H NMR (400 MHz, CDCl$_3$): δ 9.94 (s, 1H), 8.34 (bs, 1H), 8.05 (d, J=7.5 Hz, 1H), 7.74 (t, J=7.5 Hz, 1H), 7.35 (t, J=7.5 Hz, 1H), 7.26-7.13 (m, 2H), 7.02 (dd, J=8.0, 0.5 Hz, 1H), 6.91 (t, J=8.0 Hz, 2H), 6.84-6.81 (m, 2H), 4.08 (s, 2H), 3.79 (s, 3H). $^{13}$C NMR (125 MHz, CDCl$_3$): δ 167.3, 160.2, 158.8, 158.7, 156.8, 156.7, 154.6, 154.1, 149.1, 146.0, 136.6, 135.2, 130.1, 127.409, 127.3, 127.3, 124.2, 123.4, 119.0, 115.4, 112.7, 111.6, 111.6, 111.5, 111.4, 55.5, 34.9 ppm. $^{19}$F NMR (376.5 MHz, CDCl$_3$) δ−117.93 ppm.

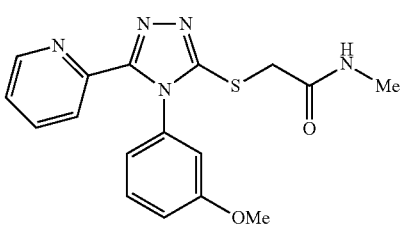 [SMILES: CNC(=O)CSc1nnc(-c2ccccn2)n1-c1cccc(OC)c1]

2-(4-(3-Methoxyphenyl)-5-(pyridin-2-yl)-4H-1,2,4-triazol-3-ylthio)-N-methylacetamide (1h)

$^1$H NMR (300 MHz, CDCl$_3$): δ 8.34 (d, J=4.2 Hz, 1H), 8.05 (d, J=7.8 Hz, 1H), 7.75 (t, J=7.5 Hz, 1H), 7.35 (t, J=7.5 Hz, 1H), 7.22 (d, J=9.0 Hz, 1H), 7.02 (dd, J=8.7, 2.4 Hz, 1H), 6.83-6.78 (m, 2H), 4.28 (s, 2H), 3.79 (s, 3H), 2.77 (s, 3H).

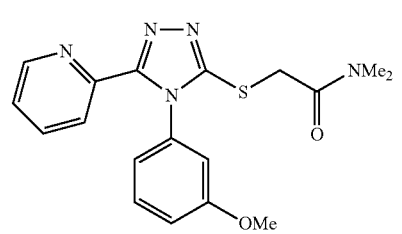 [SMILES: COc1cccc(-n2c(SCC(=O)N(C)C)nnc2-c2ccccn2)c1]

2-(4-(3-Methoxyphenyl)-5-(pyridin-2-yl)-4H-1,2,4-triazol-3-ylthio)-N,N-dimethylacetamide (1i)

$^1$H NMR (300 MHz, CDCl$_3$): δ 8.34 (d, J=4.5 Hz, 1H), 8.05 (d, J=7.8 Hz, 1H), 7.73 (dt, J=7.5, 1.5 Hz, 1H), 7.35 (t, J=8.4 Hz, 1H), 7.22 (dd, J=7.5, 4.8 Hz, 1H), 7.02 (dd, J=8.4, 2.4 Hz, 1H), 6.85-6.63 (m, 2H), 4.38 (s, 2H), 3.78 (s, 3H), 3.16 (s, 3H), 2.99 (s, 3H).

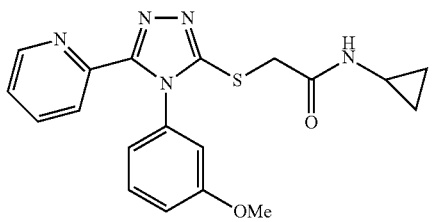 [SMILES: COc1cccc(-n2c(SCC(=O)NC3CC3)nnc2-c2ccccn2)c1]

2-(4-(3-Methoxyphenyl)-5-(pyridin-2-yl)-4H-1,2,4-triazol-3-ylthio)-N-cyclopropylacetamide (1j)

$^1$H NMR (300 MHz, CDCl$_3$): δ 8.35 (d, J=4.2 Hz, 1H), 8.00 (s, 1H), 7.98 (d, J=8.1 Hz, 1H), 7.75 (dt, J=7.5, 1.5 Hz, 1H), 7.36 (t, J=8.2 Hz, 1H), 7.22 (dd, J=7.5, 4.8 Hz, 1H), 7.02 (dd, J=8.4, 2.4 Hz, 1H), 6.81-6.77 (m, 2H), 3.79 (s, 2H), 3.71 (s, 3H), 2.77-2.71 (m, 1H), 0.78-0.75 (m, 1H), 0.59-0.54 (m. 1H).

General Scheme 2

The second series of compounds 2 were made from commercially available piperazine 2a by any of several methods. Addition of the isothiocyanate 8, which is commercially available or was prepared from the corresponding amine (e.g., with thiophosgene), to 2a in the presence of base such as triethylamine afforded the thioureas 2b-2f.

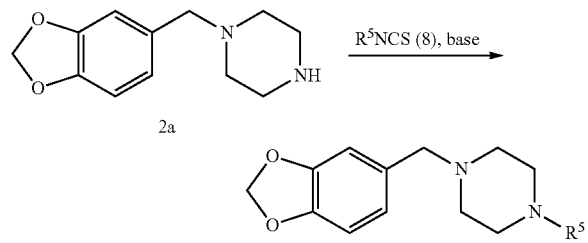

2b R$^5$=C(=S)NH(n-propyl)
2c R$^5$=C(=S)NH(benzyl)
2d R$^5$=C(=S)NH(allyl)
2e R$^5$=C(=S)NH(methyl)
2f R$^5$=C(=S)NH(phenyl)

Synthetic Examples 2b-2f

General Procedure for the Synthesis of Compounds 2b-2f

To a solution of 1-piperonylpiperazine 2a (157 mg, 0.71 mmol) in dichloromethane (5 mL), was added the appropriate isothiocyanate of formula R$^5$NCS, e.g. allyl isothiocyanate (69 μL, 0.71 mmol) and triethylamine. The reaction mixture was stirred overnight at rt. The reaction mixture was poured into water, extracted with dichloromethane and the organic layers were dried with anhydrous sodium sulfate. The residue after removal of solvent was purified by silica gel column chromatography with ethyl acetate:hexane (2:1) and afforded compounds 2b-2f.

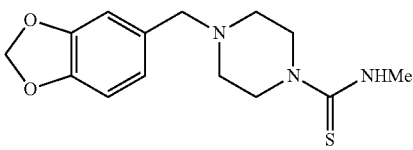 [SMILES: CNC(=S)N1CCN(Cc2ccc3c(c2)OCO3)CC1]

4-((Benzo[d][1,3]dioxol-6-yl)methyl)-N-methylpiperazine-1-carbothioamide 2e $^1$H NMR (500 MHz, CDCl$_3$): δ 6.83 (s, 1H), 6.75-6.70 (m, 2H), 5.93 (s, 2H), 5.67 (bs, 1H), 3.79 (t, J=5.0 Hz, 1H), 3.42 (s, 2H), 3.14 (d, J=10.5 Hz, 3H), 2.45 (t, J=5.0 Hz, 4H). $^{13}$C NMR (125 MHz, CDCl$_3$): δ182.9, 147.6, 146.7, 131.3, 122.1, 109.2, 107.8, 100.8, 62.3, 52.2, 47.3, 32.8 ppm.

BIOLOGICAL EXAMPLES

Example 1

Studies on Developing Novel Small-Molecule Compounds to Induce Readthrough of Nonsense Mutations in ATM Gene The following describes ways in which the compounds described herein were tested to measure readthrough activity and cytotoxicity, 1. HTS Identified Two Novel Small Molecular RTCs.

Two novel small molecular RTCs, GJ071 and GJ072 were identified using the PTT-ELISA assay described below as well as in Du et al., J Exp Med. 2009 and WO2012021707. Both compounds have structures different from any known reported RTCs (structure shown in FIG. 1a). Their readthrough activity on TGA mutation was confirmed using cell-free PTT-ELISA assay (Assay A, additional details below) based on a plasmid containing ATM fragment with a TGA mutations (FIG. 1b) and latterly confirmed in A-T cells with nonsense mutations (see below).

2. RTCs Induced Readthrough of Different ATM PTCs in A-T Cells.

To confirm GJ071 and GJ072 for their cellular readthrough activity on ATM gene, we selected three A-T LCL cell lines derived from patients containing different homozygous nonsense mutations: AT153LA (8977C>T, TGA A), AT229LA cells (TAG A), and AT185LA (3673C>T, TAA G). A-T cells were treated with each RTC for 4 days and then collected for ATM kinase activity analysis which was deficient in A-T cells due to ATM mutations. The RTC treatments partially restored ATM kinase in tested A-T cells on all three PTCs (TGA, TAG and TAA), as demonstrated by ATMs1981 auto-phosphorylation (Assay B, additional details below) and ATM nuclei foci formation after radiation (IRIF) (Assay C, additional details below, or downstream substrate SMC1 phosphorylation (Assay B) (FIG. 2 and FIG. 3). As shown in FIG. 2, both GJ071 (FIG. 2A) and GJ072 (FIG. 2B) induced ATM kinase on TGA and TAG PTCs, restoring ATMs1981 auto-phosphorylation or SMC1 phosphorylation as measured by FACS analysis. Notably, as indicated in FIG. 3, GJ071 and GJ072 were also active in A-T cells with homozygous TAA mutation, a PTC that was previously reported to be more difficult to readthrough compared to TGA and TAG.

Since a hallmark of A-T is the hypersensitivity of A-T cells to ionizing radiation, we further assessed whether these RTCs can abrogate A-T cells radio-sensitivity (Assay D, additional details below). AT242LA cells with heterozygous TGA and TAG mutations were treated with each compound for 4 days and followed by colony survival assay (CSA). As shown FIG. 4, both wildtype cells and untreated A-T cells fell into the expected survival fraction (SF) range respectively: a "normal" range of >36% SF and a "radiosensitive" range of <21% SF, which was previously established in our laboratory and is used for clinical A-T diagnosis (Sun et al, 2002). Both GJ071 and GJ072 (at 30 and 50 µM) abrogated AT242LA cellular radio-sensitivity, from "radiosensitive" range (9%) to "intermediate" range (21-36%). All together, the data from multiple A-T cells further confirmed the readthrough activity of GJ071 and GJ072 in ATM gene for three PTCs.

3. Structure Activity Relationship (SAR) Studies Used to Derive Active Analogs for GJ072.

To establish SAR and improve the design of novel readthrough compounds, we synthesized and tested analogs for both GJ071 and GJ072. For GJ071, none of the six analogs we made for GJ071 showed significant activity in A-T cells (data not shown). However, 8 of 12 GJ072 analogs we generated (structures shown in FIG. 5) were able to induce ATM kinase activity in A-T cells carrying different homozygous nonsense mutations. The activity of these analogs (GJ103, GJ104, GJ105, GJ106, GJ109, GJ111, GJ112 and GJ113) in TGA-containing A-T cells was demonstrated by restored FCATMs1981 levels using FACS analysis (FIG. 6). This was also confirmed for some of the analogs by an alternative ATMs1981 IRIF assay FIG. 31). Like GJ072, these GJ072 analogs also showed to be active in A-T cells containing TAG or TAA stop codons. The readthrough activity (Assay B or C) of the 8 analogs on a TAG stop codon in AT229LA cells is shown in FIG. 7. Their readthrough activity on TAA stop codon in AT185LA cells was shown by FCATMs1981 assay in FIG. 8 and some were confirmed by IRIF assay in FIG. 28. Furthermore, we were able to develop a water soluble salt form (GJ103-salt) on one GJ072 analog, GJ103, which also showed readthrough activity in A-T cells.

Interestingly, we identified two additional hits from the primary HTS, RTC204 and RTC219. The structures and activity of RTC204 and RTC219 in A-T cells are shown in FIG. 29.

4. Comparison of GJ071 and GJ072 with Other Known RTCs

GJ071 and GJ072 were compared with three known RTCs. To assess these new RTCs as to their efficacy, we next compared GJ071 and GJ072 with three known RTCs RTC13 and RTC14, and PTC124. RTC13 and RTC14 had been tested and confirmed their activity in multiple genes including ATM and dystrophin. Early animal experiments on RTC13 also showed its in vivo activity in mdx mice. PTC124 has been shown its potential in several gene-disease models. We also include GJ103, an analog of GJ072, since it has been formulated to a water soluble form for future in vivo evaluation. As shown in FIG. 9, GJ072 and its analogs GJ103 showed similar activity to RTC13, and was arguably better than PTC124 when tested in A-T cells (AT153LA) with a TGA stop codon. Notably, GJ071, GJ072 and some of analogs of GJ072 (GJ103, GJ104, GJ105, and GJ106) did not show obvious cytotoxicity in A-T cells up to 300 µM (FIG. 33 and FIG. 30) (Assay E, additional details below), which appeared to be better tolerated than RTC13 and 14; however, both RTC13 and 14 were cytotoxic in A-T cells over 100 µM (previously published data, Du et al, 2009). This indicates that the new RTCs reported here may have more potential for further development.

Discussion

In this study, we identified and characterized the readthrough activity of two new groups of small molecular RTCs, GJ071 and GJ072, and their analogs. With the other two previously reported RTCs, RTC13 and 14 (Du et al., 2009), totally four "parent" RTCs (original "hits") were identified from our HTS. As compared to previously studied compounds such as RTC13, RTC14 and PTC124, GJ071 and GJ072 demonstrated similar or marginally better activity in A-T cells tested (FIG. 8). Notably, GJ071 and GJ072 and some of active analogs of GJ072 (such as GJ103 and GJ105) did not show obvious cytotoxicity in cells even at very high concentrations (up to 300 µM) after four day treatment (FIG. 33). Therefore, these new RTCs appeared to be better tolerated than RTC13 and RTC14. Moreover, like RTC13 and RTC14, GJ071 and GJ072 read through all three premature stop codons. This is critical for translational potential because all three types of nonsense mutations occur in A-T patients as well as patients with other genetic diseases.

We successfully generated 8 active analogs for GJ072 (FIGS. 6-8, 31, and 32), all of which had low cLogP values, suggestive of good absorption or permeation potential in vivo. In addition, the GJ103 salt form proved to be water soluble making it easier to work with in vivo experiments. Together with other lead compounds, we identified RTC204 and RTC219, which share a similar structural feature with GJ072 and its analogs, suggesting that this structural feature may be responsible for their readthrough activity. Further SAR studies may improve drug suitability.

So far, the underlying mechanisms how these newly identified RTCs work still remains to be determined. Since all of the known PTC readthrough compounds function by interfering with ribosome, for example, PTC124 binds to the large 60S ribosomal subunit (Rowe and Clancy 2009), the potential ribosomal interaction of these RTCs should be investigated in future. Furthermore, the influence of nonsense-mediated decay (NMD) may significantly affect RTC-induced PTC-readthrough because mRNA transcripts carrying nonsense mutations are degraded by this pathway (Wilkinson and Shyu, 2002; Holbrook et al., 2004) Inhibition of NMD may stabilize mutant mRNA transcripts and increase RTC-induced readthrough output (Linde et al., 2007). These mutations may also be missed if sequencing for mutations is performed on cDNA derived from patient cells without first inhibiting NMD.

Other issues related to readthrough approaches in A-T patients that need to be further studied include the potential risk of triggering inappropriate 'retroactive' apoptosis after restoring ATM protein in A-T cells (Lee et al., 2000), and the requirement that ATM induction occurs in cerebella cells, i.e. the small molecule RTC's ability to cross the blood brain barrier (BBB) and target the brain and especially cerebellar Purkinje cells, as this is the primary site of pathology in A-T patients (Gatti and Vinters, 1985; Vinters et al., 1985). These compounds may induce readthrough of normal stop codons, thus introducing aberrantly extended proteins. Although this possibility has been investigated carefully by many investigators, none have observed evidence of reading through final stop codons, perhaps because their consensus motifs are read "in context" of surrounding signals, as well as a single three-nucleotide stop codon. Lastly, it remains possible that by substituting a "false" amino acid for a stop codon, the resulting missense-bearing ATM might lead to a dominant negative effect. Thus, in addition to these potential pitfalls, a successful small molecule RTC drug will need to have acceptable PK and drug properties (good solubility, half-life, tissue distribution, clearance, and minimal off-target toxicity).

Assays

Assay A: PTT-ELISA and HTS

The HTS was based on a cell-free PTT-ELISA system which was developed previously (Du, et al, 2009). Briefly, a plasmid containing ATM gene region 5 with a TGA C mutations (5623C>T) was used for in vitro transcription and translation reaction using TNT® T7 PCR Quick Master Mix (Promega). The readthrough full-length protein was detected by Sandwich ELISA using antibodies against c-myc and V5. About 36,000 compounds were screened to discover novel RTCs. Each compound was screened at a final concentration of 10 μM in the assay mixture. Screening was performed on a fully integrated CORE System (Beckman Coulter-SAGIAN, IN).

Assay B: Flow Cytometry Analysis of ATM-Ser1981 and SMC1-Ser966 Phosphorylation.

FC-SMC1 assay was performed as previously described (Nahas et al., 2009; Du et al, 2009). FC-ATM-Ser1981 assay was modified from Honda's assay (Honda et al., 2009). In brief, cells were resuspended in PBS and radiated for 10Gy. After one hour, the cells were fixed and permeablized using the FIX & PERM cell permeablization kit (Invitrogen). The cells were then incubated with 1 μl of ATM-Ser1981 antibody (Cell signaling, MA) for 2 hours, at room temperature. Cells were then washed and stained with 100 μL PBS with Alexo488-anti-monsue IgG (Invitrogen) for 45 minutes. After that, cells were washed and resuspended PBS with 0.2% paraformaldehyde and analyzed using FACScan (BD Biosciences, CA).

Assay C: Immunofluorescence of ATM-Ser1981 IRIF.

Immunostaining of ATM-Ser1981 nuclear foci was done as previously described (Du et al., 2007; Du et al, 2009). Briefly, cells were irradiated with 2 Gy after four-day RTC treatment and incubated at 37° C. for 30 min. The cells were dropped onto coverslips, fixed with 4% paraformaldehyde and permeabilizated. The coverslips were then blocked for 1 h using PBS with 10% FBS and incubated with mouse anti-ATM pSer1981 1 h at RT (1:500; Rockland Immunochemicals, PA). Cells were washed and blocked again for 1 h and then stained with FITC-conjugated anti-mouse IgG (1:150; Jackson ImmunoResearch, PA) and mounted onto slides.

Assay D: Colony Survival Assay (CSA).

CSA was performed as described before (Sun et al., 2002). A-T cells were treated and then plated in duplicate in 96-well plates at 100, and 200 cells per well, respectively. One of the duplicate plates was exposed to 1.0 Gy radiation, whereas the other one was left un-irradiated. The cells were incubated for 10-13 days and then stained with MTT. The presence of a colony of 32 cells (i.e., 5 cell divisions) was scored as a positive well, and survival fractions (% SF) were calculated as described (Huo et al., 1994).

Assay E: Cytotoxicity by XTT Assay.

Cytotoxicity was measured by Cell Proliferation Kit II (Roche Applied Science). This assay is based on the cleavage of the tetrazolium salt XTT in the presence of an electron-coupling reagent, producing a soluble formazan salt. This conversion only occurs in viable cells. Briefly, cells (WT LCLs and A-T LCLs) were seeded into a flat-bottom 96-well microtiter plate, including control wells containing complete growth medium alone as blank absorbance readings. After RTC treatment (at concentrations ranging from 1-300 μM for 3 days), activated-XTT Solution was added into each well and return to cell culture incubator for 12-14 hours. The absorbance was measured at 480 nM with relevant 630 nM to assess non-specific readings. The amount of the formazan salt detected directly correlates to the number of metabolically active cells in the culture.

REFERENCES

Auld D S, Thorne N, Maguire W F, Inglese J. Mechanism of PTC124 activity in cell-based luciferase assays of nonsense codon suppression. Proc Natl Acad Sci USA. 2009; 106(9):3585-90. PMCID: PMC2638738

Auld D S, Lovell S, Thorne N, Lea W A, Maloney D J, Shen M, Rai G, Battaile K P, Thomas C J, Simeonov A, Hanzlik R P, Inglese J. Molecular basis for the high-affinity binding and stabilization of firefly luciferase by PTC124. Proc Natl Acad Sci USA. 2010; 107(11):4878-83. PMCID: PMC2841876

Bedwell D M, Kaenjak A, Benos D J, Bebok Z, Bubien J K, Hong J, Tousson A, Clancy J P, Sorscher E J. Suppression of a CFTR premature stop mutation in a bronchial epithelial cell line. Nat Med. 1997; 3(11):1280-4.

Clancy J P, Bebök Z, Ruiz F, King C, Jones J, Walker L, Greer H, Hong J, Wing L, Macaluso M, Lyrene R, Sorscher E J, Bedwell D M. Evidence that systemic gentamicin suppresses premature stop mutations in patients with cystic fibrosis. Am J Respir Crit Care Med. 2001; 163(7):1683-92.

Du L, Damoiseaux R, Nahas S, Gao K, Hu H, Pollard J M, Goldstine J, Jung M E, Henning S M, Bertoni C, Gatti R A. Nonaminoglycoside compounds induce readthrough of nonsense mutations. J Exp Med. 2009; 206(10):2285-97. PMCID: PMC2757881

Du L, Kayali R, Bertoni C, Fike F, Hu H, Iversen P L, Gatti R A. A Arginine-rich cell-penetrating peptide dramatically enhances AMO-mediated ATM aberrant splicing correction and enables delivery to brain and cerebellum. Hum Mol Genet., 2011; 20(16): 3151-60.

Du M, Liu X, Welch E M, Hirawat S, Peltz S W, Bedwell D M. PTC124 is an orally bioavailable compound that promotes suppression of the human CFTR-G542X nonsense allele in a CF mouse model. Proc Natl Acad Sci USA. 2008; 105(6):2064-9. PMCID: PMC2538881

Du, M., Keeling, K. M., Fan, L., Liu, X., Bedwell, D. M. Poly-L-aspartic Acid Enhances and Prolongs Gentamicin-mediated Suppression of the CFTR-G542X Mutation in a Cystic Fibrosis Mouse Model. J. Biol. Chem. 2009; 284: 6885-6892

Gatti R A, Vinters H V. Cerebellar pathology in ataxia-telangiectasia: the significance of basket cells. Kroc Found Ser. 1985; 19:225-32.

Gilad S, Bar-Shira A, Harnik R, Shkedy D, Ziv Y, Khosravi R, Brown K, Vanagaite L, Xu G, Frydman M, Lavin M F, Hill D, Tagle D A, Shiloh Y. Ataxia-telangiectasia: founder effect among north African Jews. Hum Mol Genet. 1996; 5(12):2033-7.

Guan M X, Fischel-Ghodsian N, Attardi G. A biochemical basis for the inherited susceptibility to aminoglycoside ototoxicity. Hum Mol Genet. 2000; 9(12):1787-93. Guglieri M, Bushby K. Molecular treatments in Duchenne muscular dystrophy. Curr Opin Pharmacol. 2010; 10(3): 331-7.

Hirawat S, Welch E M, Elfring G L, Northcutt V J, Paushkin S, Hwang S, Leonard E M, Almstead N G, Ju W, Peltz S W, Miller L L. Safety, tolerability, and pharmacokinetics of PTC124, a nonaminoglycoside nonsense mutation suppressor, following single- and multiple-dose administration to healthy male and female adult volunteers. J Clin Pharmacol. 2007; 47(4):430-44.

Holbrook J A, Neu-Yilik G, Hentze M W, Kulozik A E. Nonsense-mediated decay approaches the clinic. Nat Genet. 2004; 36(8):801-8. Honda M, Takagi M, Chessa L, Morio T, Mizuatni S. Rapid diagnosis of ataxia-telangiectasia by flow cytometric monitoring of DNA damage-dependent ATM phosphorylation. Leukemia. 2009; 23:409-414.

Howard M, Frizzell R A, Bedwell D M. Aminoglycoside antibiotics restore CFTR function by overcoming premature stop mutations. Nat Med. 1996; 2(4):467-9.

Howard M T, Shirts B H, Petros L M, Flanigan K M, Gesteland R F, Atkins J F. Sequence specificity of aminoglycoside-induced stop condon readthrough: potential implications for treatment of Duchenne muscular dystrophy. Ann Neurol. 2000; 48(2):164-9.

Huo Y K, Wang Z, Hong J, Chessa L, McBride W H, Perlman S L and Gatti R A. Radiosensitivity of Ataxia-Telangiectasia, X-Linked Agammaglobulinemia, and Related Syndromes Using a Modified Colony Survival Assay. Cancer Research 1994, 54, 2544-2547.

Jung M E, Ku J M, Du L, Hu H, Gatti R A. Synthesis and evaluation of compounds that induce readthrough of premature termination codons. Bioorg Med Chem Lett. 2011; 21(19):5842-8.

Kayali R., Ku J M, Khitrov G., Jung M E, Prikhodko O., Bertoni C. Read-through compound 13 restores dystrophin expression and improves muscle function in the mdx mouse model for Duchenne muscular dystrophy. Hum. Mol. Genet. 2012, 21:4007-4020.

Keeling K M, and Bedwell D M. Pharmacological suppression of premature stop mutations that cause genetic diseases. Current Pharmacogenomics. 2005; 3:259-269.

Keeling K M, Brooks D A, Hopwood J J, Li P, Thompson J N, Bedwell D M. Gentamicin-mediated suppression of Hurler syndrome stop mutations restores a low level of alpha-L-iduronidase activity and reduces lysosomal glycosaminoglycan accumulation. Hum Mol Genet. 2001; 10(3):291-9.

Kerem E. Pharmacologic therapy for stop mutations: how much CFTR activity is enough? Curr Opin Pulm Med. 2004; 10(6):547-52.

Lai C H, Chun H H, Nahas S A, Mitui M, Gamo K M, Du L, Gatti R A. Correction of ATM gene function by aminoglycoside-induced read-through of premature termination codons. Proc Natl Acad Sci USA. 2004; 101 (44):15676-81. PMCID: PMC524838

Lee S, Chen T T, Barber C L, Jordan M C, Murdock J, Desai S, Ferrara N, Nagy A, Roos K P, Iruela-Arispe M L. Autocrine VEGF signaling is required for vascular homeostasis. Cell. 2007 Aug. 24; 130(4):691-703.

Lee Y, McKinnon P J. ATM dependent apoptosis in the nervous system. Apoptosis. 2000; 5(6):523-9.

Linde L, Boelz S, Nissim-Rafinia M, Oren Y S, Wilschanski M, Yaacov Y, Virgilis D, Neu-Yilik G, Kulozik A E, Kerem E, Kerem B. Nonsense-mediated mRNA decay affects nonsense transcript levels and governs response of cystic fibrosis patients to gentamicin. J Clin Invest. 2007; 117(3):683-92.

Loufrani L, Dubroca C, You D, Li Z, Levy B, Paulin D, Henrion D. Absence of dystrophin in mice reduces NO-dependent vascular function and vascular density: total recovery after a treatment with the aminoglycoside gentamicin. Arterioscler Thromb Vasc Biol. 2004; 24(4):671-6. PMCID: PMC2233851

Mendell J T, Dietz H C. When the message goes awry: disease-producing mutations that influence mRNA content and performance. Cell. 2001 Nov. 16; 107(4):411-4.

Mingeot-Leclercq M P, Tulkens P M. Aminoglycosides: nephrotoxicity. Antimicrob Agents Chemother. 1999; 43(5):1003-12. PMCID: PMC89104

Nahas S A, Butch A W, Du L, Gatti R A. Rapid flow cytometry-based structural maintenance of chromosomes 1 (SMC1) phosphorylation assay for identification of ataxia-telangiectasia homozygotes and heterozygotes. Clin Chem. 2009; 55(3):463-72. PMCID: PMC2980758

Peltz S W, Welch E M, Jacobson A, Trotta C R, Naryshkin N, Sweeney H L, Bedwell D M. Nonsense suppression activity of PTC124 (ataluren). Proc Natl Acad Sci USA. 2009; 106(25):E64; PMCID: PMC2700894

Politano L, Nigro G, Nigro V, Piluso G, Papparella S, Paciello O, Comi L I. Gentamicin administration in Duchenne patients with premature stop codon. Preliminary results. Acta Myol. 2003; 22(1):15-21.

Ramalho A S, Beck S, Meyer M, Penque D, Cutting G R, Amaral M D. Five percent of normal cystic fibrosis transmembrane conductance regulator mRNA ameliorates the severity of pulmonary disease in cystic fibrosis. Am J Respir Cell Mol Biol. 2002; 27(5):619-27.

Rowe S M, Clancy J P. Pharmaceuticals targeting nonsense mutations in genetic diseases: progress in development. BioDrugs. 2009; 23(3):165-74

Sossi V, Giuli A, Vitali T, Tiziano F, Mirabella M, Antonelli A, Neri G, Brahe C. Premature termination mutations in exon 3 of the SMN1 gene are associated with exon skipping and a relatively mild SMA phenotype. Eur J Hum Genet. 2001; 9(2):113-20.

Sun X, Becker-Catania S G, Chun H H, Hwang M J, Huo Y, Wang Z, Mitui M, Sanal O, Chessa L, Crandall B, Gatti R A. Early diagnosis of ataxia-telangiectasia using radiosensitivity testing. J Pediatr. 2002; 140(6):724-31.

Vinters H V, Gatti R A, Rakic P. Sequence of cellular events in cerebellar ontogeny relevant to expression of neuronal abnormalities in ataxia-telangiectasia. Kroc Found Ser. 1985; 19:233-55.

Welch E M, Barton E R, Zhuo J, Tomizawa Y, Friesen W J, Trifillis P, Paushkin S, Patel M, Trotta C R, Hwang S, Wilde R G, Karp G, Takasugi J, Chen G, Jones S, Ren H, Moon Y C, Corson D, Turpoff A A, Campbell J A, Conn M M, Khan A, Almstead N G, Hedrick J, Mollin A, Risher N, Weetall M, Yeh S, Branstrom A A, Colacino J M, Babiak J, Ju W D, Hirawat S, Northcutt V J, Miller L L, Spatrick P, He F, Kawana M, Feng H, Jacobson A, Peltz S W, Sweeney H L. PTC124 targets genetic disorders caused by nonsense mutations. Nature. 2007; 447(7140): 87-91.

Wilkinson, M. F. and A. B. Shyu. RNA surveillance by nuclear scanning'? Nat. Cell Biol. 2002, 4:E144-E147.

Wilschanski M, Famini C, Blau H, Rivlin J, Augarten A, Avital A, Kerem B, Kerem E. A pilot study of the effect of gentamicin on nasal potential difference measurements in cystic fibrosis patients carrying stop mutations. Am J Respir Crit Care Med. 2000; 161(3 Pt 1):860-5.

Zilberberg A, Lahav L, Rosin-Arbesfeld R. Restoration of APC gene function in colorectal cancer cells by aminoglycoside- and macrolide-induced read-through of premature termination codons. Gut. 2010; 59(4):496-507.

Zingman L V, Park S, Olson T M, Alekseev A E, Terzic A. Aminoglycoside-induced translational read-through in disease: overcoming nonsense mutations by pharmacogenetic therapy. Clin Pharmacol Ther. 2007; 81(1):99-103.

While particular embodiments have been shown and described, it will be obvious to those skilled in the art that changes and modifications can be made without departing from the subject matter disclosed in its broader aspects.

Therefore, the appended claims are to encompass within their scope all such changes and modifications as fall within the true spirit and scope of the subject matter disclosed.

All publications including patents, patent applications and published patent applications cited herein are hereby incorporated by reference for all purposes.

We claim:

1. A compound of formula Ia:

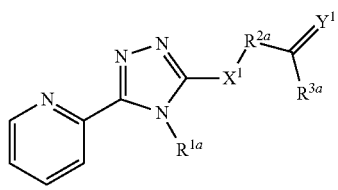

where
$R^{1a}$ is 2-hydroxylphenyl, 2-alkoxyphenyl, 3-hydroxylphenyl, or 3-alkoxyphenyl;
$X^1$ is S, O, NH, or $N(C_{1-3}$-alkyl);
$R^{2a}$ is $(CH_2)_m$;
m is 1, 2, or 3;
$Y^1$ is O, S, or NH;
$R^{3a}$ is hydroxy or $-NR^7R^{7a}$;
$R^7$ is hydrogen or $C_{1-3}$-alkyl;
$R^{7a}$ is hydroxyalkyl; phenyl substituted with 1, 2, or 3 $R^8$ groups; phenyl substituted with two independently selected halo;
each $R^8$ is independently hydroxy or haloalkyl; and
each $R^9$, when present, is independently hydroxy, alkoxy, halo, haloalkyl, or $C_{1-6}$-alkyl; and
provided that 1) when $X^1$ is S, $R^{2a}$ is $-CH_2-$, $Y^1$ is O, and $R^{3a}$ is $-NR^7R^{7a}$ and $R^7$ is hydrogen, then $R^{7a}$ is not 2-methoxyphenyl; and 2) when $R^{1a}$ is 2-methoxyphenyl, $X^1$ is S, $R^{2a}$ is $-CH_2-$, $Y^1$ is O, and $R^{3a}$ is $-NR^7R^{7a}$ and $R^7$ is hydrogen, then $R^{7a}$ is not 4-methoxyphenyl; or
a pharmaceutically acceptable salt thereof.

2. The compound of claim 1, where $X^1$ is S; or a pharmaceutically acceptable salt thereof.

3. The compound of claim 1, where $Y^1$ is O; or a pharmaceutically acceptable salt thereof.

4. The compound of claim 1, where $R^{2a}$ is $-(CH_2)_m-$ and m is 1; or a pharmaceutically acceptable salt thereof.

5. The compound of claim 1, where $R^{1a}$ is 3-alkoxyphenyl; or a pharmaceutically acceptable salt thereof.

6. The compound of claim 1, where $R^{7a}$ is hydroxyalkyl; or a pharmaceutically acceptable salt thereof.

7. The compound of claim 1, where $R^{7a}$ is phenyl substituted with two independently selected halo; or $R^{7a}$ is phenyl substituted with 1 or 2 $R^8$ groups; or a pharmaceutically acceptable salt thereof.

8. The compound of claim 1, where $R^{7a}$ is phenyl substituted with two independently selected halo; or $R^{7a}$ is phenyl substituted with one hydroxy or haloalkyl; or a pharmaceutically acceptable salt thereof.

9. The compound of claim 1, selected from 2-((4-(3-methoxyphenyl)-5-(pyridin-2-yl)-4H-1,2,4-triazol-3-yl)thio)acetic acid; sodium 2-((4-(3-methoxyphenyl)-5-(pyridin-2-yl)-4H-1,2,4-triazol-3-yl)thio)acetate; N-(4-hydroxyphenyl)-2-((4-(3-methoxyphenyl)-5-(pyridin-2-yl)-4H-1,2,4-triazol-3-yl)thio)acetamide; N-(2,6-difluorophenyl)-2-((4-(3-methoxyphenyl)-5-(pyridin-2-yl)-4H-1,2,4-triazol-3-yl)thio)acetamide; 2-((4-(3-methoxyphenyl)-5-(pyridin-2-yl)-4H-1,2,4-triazol-3-yl)thio)-N-(4-(trifluoromethyl)phenyl)acetamide; N-(1,3-dihydroxy-2-(hydroxymethyl)propan-2-yl)-2-((4-(3-methoxyphenyl)-5-(pyridin-2-yl)-4H-1,2,4-triazol-3-yl)thio)acetamide; 2-((4-(3-methoxyphenyl)-5-(pyridin-2-yl)-4H-1,2,4-triazol-3-yl)thio)-N-phenylacetamide; or a pharmaceutically acceptable salt thereof.

10. A compound having the following formula:

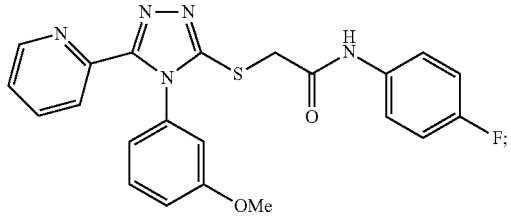 [SMILES: COc1cccc(-n2c(SCC(=O)Nc3ccc(F)cc3)nnc2-c2ccccn2)c1]

or a pharmaceutically acceptable salt thereof.

* * * * *